(12) United States Patent
Kartalov et al.

(10) Patent No.: US 10,889,863 B2
(45) Date of Patent: *Jan. 12, 2021

(54) FRET-BASED ANALYTES DETECTION AND RELATED METHODS AND SYSTEMS

(71) Applicant: CALIFORNIA INSTITUTE OF TECHNOLOGY, Pasadena, CA (US)

(72) Inventors: Emil P. Kartalov, Pasadena, CA (US); Aditya Rajagopal, Irvine, CA (US); Axel Scherer, Barnard, VT (US); Mark D. Goldberg, Alta Loma, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 138 days.

This patent is subject to a terminal disclaimer.

(21) Appl. No.: 16/102,583

(22) Filed: Aug. 13, 2018

(65) Prior Publication Data

US 2019/0127799 A1 May 2, 2019

Related U.S. Application Data

(63) Continuation of application No. 14/633,094, filed on Feb. 26, 2015, now Pat. No. 10,077,475, which is a continuation-in-part of application No. 14/162,725, filed on Jan. 23, 2014, now abandoned.

(60) Provisional application No. 61/944,856, filed on Feb. 26, 2014, provisional application No. 61/756,343, filed on Jan. 24, 2013.

(51) Int. Cl.
  *C12Q 1/68* (2018.01)
  *C12Q 1/70* (2006.01)
  *C12Q 1/6883* (2018.01)
  *C12Q 1/6851* (2018.01)

(52) U.S. Cl.
  CPC ............. *C12Q 1/6883* (2013.01); *C12Q 1/68* (2013.01); *C12Q 1/6851* (2013.01); *C12Q 1/701* (2013.01); *C12Q 1/703* (2013.01); *C12Q 2600/156* (2013.01); *Y10T 436/143333* (2015.01)

(58) Field of Classification Search
  CPC ................ C12Q 1/6883; C12Q 1/6851; C12Q 2561/113; C12Q 2565/101
  See application file for complete search history.

(56) References Cited

U.S. PATENT DOCUMENTS

| | | | |
|---|---|---|---|
| 10,077,475 B2 * | 9/2018 | Kartalov | C12Q 1/68 |
| 2010/0068711 A1 * | 3/2010 | Umansky | C12Q 1/6886 435/6.16 |
| 2010/0203537 A1 * | 8/2010 | Miller | C12Q 1/6818 435/6.15 |

* cited by examiner

*Primary Examiner* — David C Thomas
(74) *Attorney, Agent, or Firm* — Sheppard Mullin Richter & Hampton LLP

(57) ABSTRACT

FRET-based analytes detection and related methods and systems are described where a pair of FRET labeled primers and/or oligonucleotides are used that are specific for target sequences located at a distance up to four time the Förster distance of the FRET chromophores presented on the FRET labeled primers and/or oligonucleotides one with respect to the other in one or more polynucleotide analyte; in particular the pair of FRET labeled primers and/or oligonucleotides is combined with a sample and subjected to one or more polynucleotide amplification reactions before measuring FRET signals from at least one FRET chromophore.

38 Claims, 22 Drawing Sheets

Specification includes a Sequence Listing.

$\kappa^2 = (\cos\theta_T - 3\cos\theta_D \cos\theta_A)^2$
$= (\cos\theta_D \sin\theta_A \cos\phi - 2\cos\theta_D \sin\theta_A)^2$

SEQUENCE LISTING

```
<160> NUMBER OF SEQ ID NOS: 20

<210> SEQ ID NO 1
<211> LENGTH: 90
<212> TYPE: DNA
<213> ORGANISM: artificial sequence
<220> FEATURE:
<223> OTHER INFORMATION: synthetic polynucleotide

<400> SEQUENCE: 1
atgactgaat ataaacttgt ggtagttgga gctggtggcg taggcaagag tgccttgacg        60
atacagctaa ttcagaatca ttttgtggac                                        90

<210> SEQ ID NO 2
<211> LENGTH: 90
<212> TYPE: DNA
<213> ORGANISM: artificial sequence
<220> FEATURE:
<223> OTHER INFORMATION: synthetic polynucleotide

<400> SEQUENCE: 2
atgactgaat ataaacttgt ggtagttgga gctgatggcg taggcaagag tgccttgacg        60
atacagctaa ttcagaatca ttttgtggac                                        90

<210> SEQ ID NO 3
<211> LENGTH: 90
<212> TYPE: DNA
<213> ORGANISM: artificial sequence
<220> FEATURE:
<223> OTHER INFORMATION: synthetic polynucleotide

<400> SEQUENCE: 3
atgactgaat ataaacttgt ggtagttgga gctgttggcg taggcaagag tgccttgacg        60
atacagctaa ttcagaatca ttttgtggac                                        90

<210> SEQ ID NO 4
<211> LENGTH: 90
<212> TYPE: DNA
<213> ORGANISM: artificial sequence
<220> FEATURE:
<223> OTHER INFORMATION: synthetic polynucleotide

<400> SEQUENCE: 4
atgactgaat ataaacttgt ggtagttgga gctgctggcg taggcaagag tgccttgacg        60
atacagctaa ttcagaatca ttttgtggac                                        90

<210> SEQ ID NO 5
<211> LENGTH: 90
<212> TYPE: DNA
<213> ORGANISM: artificial sequence
<220> FEATURE:
<223> OTHER INFORMATION: synthetic polynucleotide
```

<400> SEQUENCE: 5
atgactgaat ataaacttgt ggtagttgga gctgctgacg taggcaagag tgccttgacg    60
atacagctaa ttcagaatca ttttgtggac    90

<210> SEQ ID NO 6
<211> LENGTH: 90
<212> TYPE: DNA
<213> ORGANISM: artificial sequence
<220> FEATURE:
<223> OTHER INFORMATION: synthetic polynucleotide

<400> SEQUENCE: 6
atgactgaat ataaacttgt ggtagttgga gctactggcg taggcaagag tgccttgacg    60
atacagctaa ttcagaatca ttttgtggac    90

<210> SEQ ID NO 7
<211> LENGTH: 90
<212> TYPE: DNA
<213> ORGANISM: artificial sequence
<220> FEATURE:
<223> OTHER INFORMATION: synthetic polynucleotide

<400> SEQUENCE: 7
atgactgaat ataaacttgt ggtagttgga gcttctggcg taggcaagag tgccttgacg    60
atacagctaa ttcagaatca ttttgtggac    90

<210> SEQ ID NO 8
<211> LENGTH: 29
<212> TYPE: DNA
<213> ORGANISM: artificial sequence
<220> FEATURE:
<223> OTHER INFORMATION: synthetic polynucleotide

<400> SEQUENCE: 8
gaatataaac ttgtggtagt tggagctga    29

<210> SEQ ID NO 9
<211> LENGTH: 19
<212> TYPE: DNA
<213> ORGANISM: artificial sequence
<220> FEATURE:
<223> OTHER INFORMATION: synthetic polynucleotide

<400> SEQUENCE: 9
gcactcttgc ctacgccat    19

<210> SEQ ID NO 10
<211> LENGTH: 29
<212> TYPE: DNA
<213> ORGANISM: artificial sequence
<220> FEATURE:
<223> OTHER INFORMATION: synthetic polynucleotide

<400> SEQUENCE: 10
gaatataaac ttgtggtagt tggagctgt    29

<210> SEQ ID NO 11
<211> LENGTH: 19
<212> TYPE: DNA
<213> ORGANISM: artificial sequence
<220> FEATURE:
<223> OTHER INFORMATION: synthetic polynucleotide

```
<400> SEQUENCE: 11
gcactcttgc ctacgccaa                                                    19

<210> SEQ ID NO 12
<211> LENGTH: 29
<212> TYPE: DNA
<213> ORGANISM: artificial sequence
<220> FEATURE:
<223> OTHER INFORMATION: synthetic polynucleotide

<400> SEQUENCE: 12
gaatataaac ttgtggtagt tggagctgc                                         29

<210> SEQ ID NO 13
<211> LENGTH: 19
<212> TYPE: DNA
<213> ORGANISM: artificial sequence
<220> FEATURE:
<223> OTHER INFORMATION: synthetic polynucleotide

<400> SEQUENCE: 13
gcactcttgc ctacgccag                                                    19

<210> SEQ ID NO 14
<211> LENGTH: 32
<212> TYPE: DNA
<213> ORGANISM: artificial sequence
<220> FEATURE:
<223> OTHER INFORMATION: synthetic polynucleotide

<400> SEQUENCE: 14
gaatataaac ttgtggtagt tggagctggt ga                                     32

<210> SEQ ID NO 15
<211> LENGTH: 21
<212> TYPE: DNA
<213> ORGANISM: artificial sequence
<220> FEATURE:
<223> OTHER INFORMATION: synthetic polynucleotide

<400> SEQUENCE: 15
tcaaggcact cttgcctacg t                                                 21

<210> SEQ ID NO 16
<211> LENGTH: 28
<212> TYPE: DNA
<213> ORGANISM: artificial sequence
<220> FEATURE:
<223> OTHER INFORMATION: synthetic polynucleotide

<400> SEQUENCE: 16
gaatataaac ttgtggtagt tggagcta                                          28

<210> SEQ ID NO 17
<211> LENGTH: 19
<212> TYPE: DNA
<213> ORGANISM: artificial sequence
<220> FEATURE:
<223> OTHER INFORMATION: synthetic polynucleotide

<400> SEQUENCE: 17
cactcttgcc tacgccact                                                    19
```

```
<210> SEQ ID NO 18
<211> LENGTH: 28
<212> TYPE: DNA
<213> ORGANISM: artificial sequence
<220> FEATURE:
<223> OTHER INFORMATION: synthetic polynucleotide

<400> SEQUENCE: 18
gaatataaac ttgtggtagt tggagctt                                          28

<210> SEQ ID NO 19
<211> LENGTH: 19
<212> TYPE: DNA
<213> ORGANISM: artificial sequence
<220> FEATURE:
<223> OTHER INFORMATION: synthetic polynucleotide

<400> SEQUENCE: 19
cactcttgcc tacgccaca                                                    19

<210> SEQ ID NO 20
<211> LENGTH: 21
<212> TYPE: DNA
<213> ORGANISM: artificial sequence
<220> FEATURE:
<223> OTHER INFORMATION: synthetic polynucleotide

<400> SEQUENCE: 20
gtccacaaaa tgaatctgaa t                                                 21
```

FRET-BASED ANALYTES DETECTION AND RELATED METHODS AND SYSTEMS

CROSS REFERENCE TO RELATED APPLICATIONS

This application is a continuation of application Ser. No. 14/633,094, filed on Feb. 26, 2015, which claims priority to provisional application Ser. No. 61/944,856 entitled "FRETplex PCR assays" filed on Feb. 26, 2014. Application Ser. No. 14/633,094 is a continuation-in-part of and claims priority to U.S. application Ser. No. 14/162,725 entitled "Chromophore based characterization and Detection methods" filed on Jan. 23, 2014, which in turn claims priority of U.S. provisional application 61/756,343, filed Jan. 24, 2013, the disclosures of which are incorporated herein by reference in their entirety.

FIELD

The present disclosure relates to analyte detection and in particular to a FRET based analytes detection and/or characterization and related methods and systems.

BACKGROUND

Nucleic acid analyte identification is a critical procedure in a variety of biomedical applications, such as in research and clinical diagnostic environments. Identification of an analyte is primarily done by sequencing or by amplification-based detection. For example, in the latter scheme, the polymerase chain reaction is often used to increase the quantity of the nucleic acid analyte present.

Then, the nucleic acid analytes are discriminated using one of several additional techniques including fluorescence intensity measurement (e.g., fluorescent probes or intercalating dyes), length discrimination (e.g., using gel electrophoresis or melt curve analysis), or chromatography (e.g., haptin-based nucleic acid capture). Thus, current amplification based detection technology indirectly detects analytes and requires a secondary technique (such as gel electrophoresis or mass spectroscopy) for analyte detection. Amplification-based techniques that directly detect analytes would improve efficiency, time and cost.

SUMMARY

Disclosed herein are methods, compositions, and kits for detecting analytes, particularly polynucleotides and/or polypeptides. The methods generally involve using oligonucleotides (e.g., primers, probes) attached to FRET chromophores in amplification or polymerization reactions in order to detect a polynucleotide analyte through detection of at least one FRET signal and in particular of at least one FRET donor and/or FRET acceptor signals from FRET chromophores used in the methods, compositions and kits of the disclosure in FRET donor-acceptor chromophores pairs.

In some embodiments, provided herein are methods of detecting at least one polynucleotide analyte in a sample, comprising: (a) combining the sample with a first primer and a first oligonucleotide, wherein a first FRET chromophore is attached to the first primer, a second FRET chromophore is attached to the first oligonucleotide, the first primer and the first oligonucleotide are specific for a first polynucleotide analyte and the first FRET chromophore is different from the second FRET chromophore; (b) optionally measuring at least a first FRET signal and in particular a first donor signal generated by a FRET donor of the first and second FRET chromophores; (c) performing at least one polymerization reaction with the first primer using the first polynucleotide analyte as a template; and (d) measuring at least a second FRET signal and in particular a second acceptor signal generated by a FRET acceptor of the first and second FRET chromophores; wherein the first and second signals are used to detect the first polynucleotide analyte. In the method, the first FRET chromophore and the second FRET chromophore are capable to provide an energy transfer from one to another when located at a Förster distance one with respect to the another, thus forming a FRET donor-acceptor chromophores pair. In the method the first primer and first oligonucleotide specifically bind to target sequences located in the polynucleotide analyte so that upon specific binding of the first primer with the target sequence specific for the first primer, and upon specific binding of the first oligonucleotide with the target sequence specific for the first oligonucleotide, the first FRET chromophore and the second FRET chromophore are located within a distance up to four times the Förster distance one with respect to the other, preferably within three times the Förster distance one with respect to the other, more preferably within two times the Förster distance one with respect to the other, even more preferably within or at the Förster distance one with respect to the other In the method measuring a signal from the second FRET chromophore attached to the first oligonucleotide is performed following binding of the first oligonucleotide with the first polynucleotide analyte before and/or after (c) performing at least one polymerization reaction.

In some cases, the first FRET chromophore is attached to the 5' end of the first primer. In some cases, the first FRET chromophore is an inorganic or organic dye, a fluorophore or another chromophore. In some cases, the second FRET chromophore is attached to the 5' end of the first oligonucleotide. In some cases, the second chromophore is an inorganic or organic dye. In some cases, the first FRET chromophore and/or the second FRET chromophore is a fluorophore. In some cases, the fluorophore is 6-F AM (Fluorescein), 6-F AM (NETS Ester), Fluorescein dT, HEX, JOE (NETS Ester), MAX, TET, ROX, TAMRA, TARMA (NETS Ester), TEX615, ATTO 488, ATTO 532, ATTO 550, ATTO 565, ATTO Rho 1 Ol, ATTO 590, ATTO 633, ATTO 647N, Cy3, Cy5, TYE 563, TYE 665 or TYE 705.

In some cases, the first oligonucleotide is a second primer and (c) performing at least one polymerization reaction is performed by performing at least one polymerization reaction with the first primer and with the second primer using the first polynucleotide analyte as a template. In some of those cases the second primer forms a primer pair with the first primer, and performing at least one polymerization reaction with the first primer using the first polynucleotide analyte as a template is performed using the first primer and the second primer as forward and reverse primer of the primer pair.

In some cases methods of detecting a polynucleotide analyte with at least one primer pair are described, in which a first primer is a forward primer and a second primer is a reverse primer. In some of those embodiments the method comprises at least: (a) combining the sample with the at least one primer pair formed by the forward primer attaching a first FRET chromophore and the reverse primer attaching a second FRET chromophore (c) performing at least one polynucleotide amplification reaction with the forward primer and the reverse primer of the at least one primer pair; and (d) measuring at least one FRET signal, and in particular an acceptor signal, generated by the first FRET chromophore and/or second FRET chromophores to detect the at least one polynucleotide analyte in the sample following the performing. In the method, the first FRET chromophore and the second FRET chromophore are capable of providing an energy transfer from one to another when located at a Förster distance one with respect to the another, thus forming a FRET donor-acceptor chromophores pair. In the method the first primer and second primer specifically bind to target sequences located in the polynucleotide analyte so that upon specific binding of the first primer with the target sequence specific for the first primer, and upon specific binding of the second primer with the target sequence specific for the first oligonucleotide, the first FRET chromophore and the second FRET chromophore are located within a distance up to four times the Förster distance one with respect to the other, preferably within three times the Förster distance one with respect to the other, more preferably within two times the Förster distance one with respect to the other, even more preferably within or at the Förster distance one with respect to the other In some cases, the method can comprise (b) measuring at least one FRET signal, and in particular a donor signal, generated by the first FRET chromophore and/or second FRET chromophores before the performing; and detecting the at least one polynucleotide analyte by the FRET signal and in particular the acceptor signal measured following the performing in combination with the FRET signal and in particular the donor signal measured before the performing.

In some cases the measuring (b) of methods herein described can be performed by measuring the first donor signal generated by the FRET donor of the first and second FRET chromophore and a first acceptor signal generated by the acceptor of the first and second FRET chromophores. In some of those embodiments the measuring (d) can be performed by measuring the second acceptor signal generated by the FRET acceptor of the first and second FRET chromophore and a second donor signal generated by the donor of the first and second FRET chromophores. In some of those cases, the methods described herein can further comprise comparing the first donor signal and the second donor signal generated by the FRET donor of the first and second FRET chromophores and/or the first acceptor signal and the second acceptor signal generated by the FRET acceptor of the first and second FRET chromophores, wherein a change in the first and second donor signals and/or a change in the first and second acceptor signals indicates the presence of the first polynucleotide analyte. In some cases, the change is an increase in intensity of the second acceptor signal compared to the first acceptor first signal. In some cases, the increase in fluorescent intensity of the second signal is at least about a 30% in signal (or at least about 10%, 20%, 30%, 35%, 40%, 45%, 50%, 55%, 60%, or 75%). In some cases, the decrease in fluorescent intensity is a decrease of the second donor signal compared to the first donor signal, and can be at least about a 30% in signal (or at least about 10%, 20%, 30%, 35%, 40%, 45%, 50%, 55%, 60%, or 75%).

In some cases, the second acceptor and/or donor signals are measured after a second polymerization reaction. In some cases performing at least one polymerization reaction comprises performing a plurality of polymerase chain reactions, one or more polymerase chain reaction possibly followed by measuring an acceptor and/or donor signal from the first and second FRET. In some of those cases, the method can further comprises comparing the donor and/or acceptor signals generated before and after the one or more polymerase chain reactions.

In some cases, the polymerization reaction is a polymerase chain reaction process or an isothermal process. In some cases, the polymerase chain reaction process is an end-point polymerase chain reaction process, a real-time polymerase chain reaction process, a digital polymerase chain reaction process, a droplet digital polymerase chain reaction process, or a quantitative polymerase chain reaction process. In some cases, the first primer is a forward primer and the second primer is a reverse primer. In some cases, the first primer is a reverse primer and the second primer is a forward primer. The first and second FRET chromophores interact through an electron-transfer process as will be understood by a skilled person. In some cases, the first polynucleotide analyte is from about 10 to about 500 nucleotides in length. In some cases, the concentration of the first polynucleotide analyte is from about 10 µM to about 10 aM. In some cases, the first polynucleotide analyte is a DNA polynucleotide analyte. In some cases, the first polynucleotide analyte is an RNA polynucleotide analyte.

In some cases, the first polynucleotide analyte comprises a variation of the polynucleotide sequence or of a portion thereof which can be a genetic variation. In some cases, the genetic variation comprises a substitution, an addition, a deletion or a translocation. In some cases, the genetic variation comprises a single-nucleotide polymorphism (SNP). In some cases, the at least one polynucleotide analyte is from a source selected from a human, a non-human mammal, a plant, a bacteria, a fungus, an archaea, a parasite, or a virus. In some cases, the virus is a human immunodeficiency virus, an influenza type A virus, an influenza type B virus, a respiratory syncytial virus type A (RsvA), a respiratory syncytial virus type B virus (RsvB), a human rhinovirus (Hrv), a human metapneumovirus (Hmpv) or a human parainfluenza virus type 3 (PN-3). In some cases, the sample is a forensic sample, a clinical sample, a food sample, an environmental sample, a pharmaceutical sample, or a sample from a consumer product.

Also disclosed herein are methods of detecting a polynucleotide analyte and in particular at least one variation, e.g. a genetic variation, in a polynucleotide analyte comprising: (a) combining a first polynucleotide analyte with a first primer and a second primer, wherein a first FRET chromophore is attached to the first primer, a second FRET chromophore is attached to the second primer, at least one of the first and the second primers are specific for a first genetic variation in the first polynucleotide analyte and the first FRET chromophore is different from the second FRET chromophore; (b) measuring a first donor signal generated by a FRET donor of the first and second FRET chromophores and/or a first acceptor signal generated by a FRET acceptor of the first and second FRET chromophore; (c) performing at least one polymerization reaction with the first primer and the second primer using the first analyte as a template; and (d) measuring a second acceptor signal generated by a FRET acceptor of the first and second FRET chromophores and/or a second donor signal generated by the FRET donor of the first and second FRET chromophore; wherein the first and second signals are used to detect the first genetic variation in the first analyte. In methods herein described, the first FRET chromophore and the second FRET chromophore are capable of providing an energy transfer from one to another when located at a Förster distance one with respect to the another, thus forming a FRET donor-acceptor chromophores pair. In the method the first primer and second primer specifically bind to target sequences located in the polynucleotide analyte in a region possibly including the first genetic variation such that upon specific binding of the first primer with the target sequence specific for the first primer and upon specific binding of the second primer with the target sequence specific for the second primer the first FRET chromophore and the second FRET chromophore are located within a distance up to four times the Förster distance one with respect to the other, preferably within three times the Förster distance one with respect to the other, more preferably within two times the Förster distance one with respect to the other, even more preferably within or at the Förster distance one with respect to the other.

In some cases, the first and second donor signals are a fluorescence emission signal generated by the FRET donor of the first and second chromophores and the first and second acceptor signal are another fluorescence emission signal generated by the FRET acceptor of the first and second chromophores. In some cases the first primer and the second primer form a primer pair. In some preferred cases, the first primer and the second primer are both specific for the first genetic variation in the first analyte. In other cases, one of the first and second primers is specific for the first genetic variation in the first analyte and the other primer is a common primer that is specific for the wild-type of the first analyte. In some cases the first primer is specific for the first genetic variation in the first analyte and the second primer is specific for a second genetic variation in the first analyte.

In some cases, the methods described herein further comprise comparing the first and second donor and/or acceptor signals, wherein a change in the donor and/or acceptor signals indicates the presence of the genetic variation in the first analyte.

In some cases, the analyte is a polynucleotide analyte. In some cases, the genetic variation comprises a substitution, an addition, a deletion or a translocation. In some cases, the genetic variation comprises a single-nucleotide polymorphism (SNP). In some cases, the first primer comprises a sequence encoding the SNP or the first primer binds to a region of the analyte encoding the SNP. In some cases, the second primer comprises a sequence not encoding the SNP or the second primer comprises a sequence complementary to a region of the analyte not encoding the SNP. In some cases, the first primer encodes a region of the analyte less than 500 base pairs apart from a region of the analyte encoded by the second primer. In some cases, the change in signal is distinct for at least two of the mismatched base pairs selected from the group consisting of UU, UT, UG, UC, UA, AA, TI, GG, CC, AG, AC, TG and TC. In some cases, the change in signal from a mismatched base pair is distinct from a change in signal from a complementary base pair.

In some cases, step (a) of the methods described herein further comprises combining the first analyte with a third primer and a fourth primer, wherein a third FRET chromophore is attached to the third primer, a fourth FRET chromophore is attached to the fourth primer, the third and the fourth primers are specific for a second genetic variation in the first analyte and the third FRET chromophore is different from the forth FRET chromophore; step (b) further comprises measuring a third donor signal generated by a FRET donor of the third and fourth FRET chromophores and/or a third acceptor signal generated by a FRET acceptor of the third and fourth FRET chromophore; step (d) further comprises measuring a fourth acceptor signal generated by a FRET acceptor of the third and fourth FRET chromophores and/or a fourth donor signal generated by a FRET donor of the third and fourth FRET chromophore; and the method further comprises comparing the third and fourth donor and/or acceptor signals; wherein a change in the third and fourth donor and/or acceptor signals indicates the presence of the second single genetic variation in the first analyte. In those cases the third and fourth FRET chromophore are capable of providing an energy transfer from one to another when located at a Förster distance one with respect to the another thus forming a FRET donor-acceptor chromophores pair. In the method the third primer and fourth primer specifically bind to target sequences in a region possibly including the second genetic variation the target sequences located in the polynucleotide analyte so that upon specific binding of the third primer with the target sequence specific for the third primer and specific binding of the fourth primer with the target sequence specific for the fourth primer the third FRET chromophore and the fourth FRET chromophore are located within a distance up to four times the Förster distance one with respect to the other.

In some cases, step (a) of the methods above further comprises combining a second polynucleotide analyte with a third primer and a fourth primer, wherein a third FRET chromophore is attached to the third primer, a fourth FRET chromophore is attached to the fourth primer comprises, the third and the fourth primers are specific for a second genetic variation in the second analyte and the third chromophore is different from the fourth chromophore; step (b) further comprises measuring a third donor signal generated by a FRET donor of the third and fourth FRET chromophores and/or a third acceptor signal generated by a FRET acceptor of the third and fourth FRET chromophore; step (d) further comprises measuring a fourth acceptor signal generated by a FRET acceptor of the third and fourth FRET chromophores and/or a fourth donor signal generated by a FRET donor of the third and fourth FRET chromophore; and the method further comprises comparing the third and fourth donor and/or acceptor signals; wherein a change in the third and fourth donor and/or acceptor signals indicates the presence of the second single genetic variation in the second analyte. In the method the third FRET chromophore and the fourth FRET chromophore capable of providing an energy transfer from one to another when located at a Förster distance one with respect to the another, thus forming a FRET donor-acceptor chromophores pair. In the method the third primer and fourth primer specifically bind to target sequences located in the second polynucleotide analyte in a region possibly including the second genetic variation so that upon specific binding of the third primer with the target sequence specific for the third primer and specific binding of the fourth primer with the target sequence specific for the fourth primer the third FRET chromophore and the fourth FRET chromophore are located within a distance up to four times the Förster distance one with respect to the other.

In some cases, step (a) of the methods above further comprises combining a second polynucleotide analyte with a third primer and a fourth primer, wherein the first FRET chromophore is attached to the third primer, the second FRET chromophore is attached to the fourth primer, and the third and the fourth primers are specific for a second genetic variation in the second analyte. In the method the first FRET chromophore and the second FRET chromophore capable of providing an energy transfer from one to another when located at a Förster distance one with respect to the another, thus forming a FRET donor-acceptor chromophores pair. In the method the third primer and fourth primer specifically bind to target sequences located in the second polynucleotide analyte in a region possibly including the genetic variation so that upon specific binding of the third primer with the target sequence specific for the third primer and specific binding of the fourth primer with the target sequence specific for the fourth primer, the third FRET chromophore and the fourth FRET chromophore are located within a distance up to four times the Förster distance one with respect to the other. In some cases, the polymerization reaction is a PCR process or an isothermal reaction. In some cases, the PCR process is an end-point PCR process, a digital PCR process, a real-time PCR process, a droplet digital PCR process, or a quantitative PCR process. In some cases, the polymerization reaction is a quantitative PCR process. In some cases, the detecting comprises a quantitative PCR method. In some cases, the measuring comprises a quantitative PCR method and a second method. In some cases, the second method is a digital PCR process. In some cases, at least one SNP is detected in a gene. In some cases, at least one SNP is associated with a disease. In some cases, the disease is a genetic disorder, an autoimmune disease, a neurological disease, a cardiovascular disease, or a cancer.

Also disclosed herein are methods of detecting a plurality of analytes, comprising: (a) combining the plurality of analytes with a plurality of primer pairs, wherein each primer pair is specific to a single analyte and each primer of the primer pair is attached to a FRET chromophore of a plurality of FRET chromophore pairs each FRET chromophore pair comprising a FRET donor and a FRET acceptor; (b) measuring a first set of donor signals generated by FRET donors of the plurality of FRET chromophores pairs attached to the plurality of primer pairs and/or a first set of acceptor signals generated by FRET acceptors of the FRET chromophores plurality of FRET chromophores pairs attached to the plurality of primer pairs; (c) performing at least one polymerization reaction with the plurality of primer pairs using the plurality of analytes as templates; and (d) measuring a second set of acceptor signals generated by the FRET acceptors of the plurality of FRET chromophores pairs attached to the plurality of primer pairs and/or a second set of donor signals generated by the FRET donors of the plurality of FRET chromophores pairs attached to the plurality of primer pairs; wherein the first and second set of donor and/or signals are used to detect each analyte of the plurality of analytes. In some cases, the method described herein further comprises: (e) repeating step (c) and (d) at least once; and (f) generating a set of signature profiles; wherein the presence of each analyte of the plurality of analytes is detected by comparing the set of signature profiles to a control set of signature profiles. In the method the FRET chromophores attached to a primer pair are capable of providing an energy transfer from one to another when located at a Förster distance one with respect to the another, thus forming a FRET chromophores pair. In the method the forward primer and reverse primer of each primer pair specifically bind to target sequences located in the respective polynucleotide analyte so that upon specific binding of the forward primer with the target sequence specific for the forward primer and upon specific binding of the reverse primer with the target sequence specific for the reverse primer the FRET chromophore attached to the forward primer and the FRET chromophore attached to the reverse forward primer are located within a distance up to four times the respective Förster distance one with respect to the other.

In some cases FRET chromophores of different primer pairs are also selected to provide an energy transfer from one to another when located at a Förster distance one with respect to the another, thus forming a plurality of FRET chromophore pairs attached to a same or different primer pairs. In some preferred cases, the first primer and the second primer are both specific for the detection of the particular analyte. In some cases, the signature profile for each analyte of the plurality of analytes is a graph having the x-axis represented by the number of PCR cycles and the y-axis represented by the emission intensity generated by FRET acceptor of at least one FRET chromophore pair attached to the primer pair that is specific for that particular analyte. In other cases, only one primer of the primer pair is specific for the detection of a particular analyte and the other primer is a common primer that is not specific for the detection of the particular analyte.

Also disclosed herein are methods of generating a signature curve profile for a polynucleotide analyte, comprising: (a) contacting the polynucleotide analyte with a first primer and a second primer, wherein a first FRET chromophore is attached to the first primer and a second FRET chromophore is attached to the second primer, the first primer and the second primer are specific for the polynucleotide analyte and the first FRET chromophore is different from the second FRET chromophore; (b) measuring a first donor signal generated by a FRET donor of the first and second FRET chromophores at a first temperature and/or a first acceptor signal generated by a FRET acceptor of the first and second FRET chromophores; (c) performing at least one polymerization reaction with the first primer and the second primer using the polynucleotide analyte as a template; (d) measuring a second acceptor signal generated by a FRET acceptor of the first and second FRET chromophores at the first temperature and/or a second donor signal generated by the FRET donor of the first and second FRET chromophores; and (e) repeating step (c) and (d) at least once; wherein the signals create the signature curve profile of the polynucleotide analyte. In some cases, the method disclosed herein further comprises: (f) changing the temperature; (g) measuring a third donor and/or acceptor signal generated by a FRET donor and/or a FRET acceptor of the first and second FRET chromophores at a second temperature; and (h) repeating steps f and g at least once; wherein the signals create the signature curve profile of the polynucleotide analyte. In the method the first FRET chromophore and the second FRET chromophore are selected in order to provide an energy transfer from one to another when located at a Förster distance one with respect to the another, thus forming a FRET donor-acceptor chromophores pair. In the method the first primer and second primer specifically bind to target sequences located in the polynucleotide analyte so that upon specific binding of the first primer with the target sequence specific for the first primer and upon specific binding of the second primer with the target sequence specific for the second primer the first FRET chromophore and the second FRET chromophore are located within a distance up to four times the Förster distance one with respect to the other.

In some cases, the signature curve is a length curve, a morphology curve, a melt curve, or a SNP curve. In some cases, the polymerization reaction is a polymerase chain reaction process. In some cases, the polymerase chain reaction process is an end-point polymerase chain reaction process, a real-time polymerase chain reaction process, a digital polymerase chain reaction process or a quantitative polymerase chain reaction process. In some cases, the first FRET chromophore is an inorganic or organic dye, or a fluorophore. In some cases, the first FRET chromophore is a fluorophore. In some cases, the fluorophore is 6-F AM (Fluorescein), 6-F AM (NETS Ester), Fluorescein dT, HEX, JOE (NHS Ester), MAX, TET, ROX, TAMRA, TARMA (NHS Ester), TEX 615, ATTO 488, ATIO 532, ATIO 550, ATTO 565, ATTO Rho101, ATTO 590, ATIO 633, ATTO 647N, TYE 563, Cy3, Cy5, Alexa Fluor family, TYE 665 or TYE 705. In some cases, the second FRET chromophore is an inorganic or organic dye, or a fluorophore. In some cases, the polynucleotide analyte is a DNA polynucleotide analyte. In some cases, the polynucleotide analyte is an RNA polynucleotide analyte. In some cases, the polynucleotide analyte is from a source selected from the group consisting of a human, a non-human mammal, a plant, a bacteria, an archaea, a fungus, a parasite, and a virus. In some cases, the virus is a human immunodeficiency vims, an influenza type A virus, an influenza type B virus, a respiratory syncytial virus type A (RsvA), a respiratory syncytial virus type B virus (RsvB), a human rhinovirus (Hrv), a human metapneumovirus (Hmpv) or a human parainfluenza virus type 3 (PTV-3).

Also disclosed herein are methods of detecting a polynucleotide analyte comprising: (a) combining the polynucleotide analyte with at least two FRET chromophores, wherein the at least two FRET chromophores are each attached to a separate polynucleotide that is complementary to a region within the polynucleotide analyte; (b) performing at least one polymerization reaction to incorporate the at least two FRET chromophores into products of the polymerization reaction; and (c) detecting a fluorescent intensity from the at least two FRET chromophores at a first timepoint and a second timepoint, wherein the second timepoint is later than the first timepoint and wherein a change (particularly an increase for acceptor FRET chromophores and a decrease for a donor FRET chromophore) in fluorescent intensity at the second timepoint relative to the first timepoint is indicative of the presence of the polynucleotide analyte. In the method the at least two FRET chromophores are selected to provide an energy transfer from one to another when located at a Förster distance one with respect to the another, thus forming at least one FRET chromophore pair. In some cases, the polymerization reaction is a polymerase chain reaction. In some cases, the first timepoint is after step (a) and the second timepoint is after step (b). In some cases, the products of the at least one polymerization reaction each comprise a first polynucleotide strand and a second polynucleotide strand, wherein the first polynucleotide strand and the second polynucleotide strand are complementary. In some cases, the at least two FRET chromophores are different. In some cases, the at least two FRET chromophores comprise a fluorophore. In some cases, the fluorophore is incorporated into the first polynucleotide strand and a second fluorophore or chromophore is incorporated into the second polynucleotide strand. In some cases, the fluorophore is incorporated at the 5' end of first polynucleotide strand and the second fluorophore or other chromophore is incorporated at the 5' end of the second polynucleotide strand.

Also disclosed herein are compositions and kits, particularly for detecting polynucleotide or polypeptide analytes. In some cases, the kits comprise oligonucleotides (e.g., primers, probes, etc.) attached to a FRET chromophore (e.g., fluorophore). In the kit the FRET chromophores are selected to provide at least one FRET pair each pair formed by a FRET donor chromophore and a FRET acceptor chromophore providing an energy transfer from one to another when located at a Förster distance one with respect to the another. In some cases, the kit comprises: (a) a first primer or probe attached to a first FRET chromophore; and (b) a second primer or probe attached to a second FRET chromophore wherein the first FRET chromophore and the second FRET chromophore are selected from to form a FRET donor-acceptor chromophore pair. In the kits the first primer and second primer specifically bind to target sequences located in one or more polynucleotide analytes so that upon specific binding of the first primer with the target sequence specific for the first primer and upon specific binding of the second primer with the target sequence specific for the second primer the first FRET chromophore and the second FRET chromophore are located within a distance up to four times the Förster distance one with respect to the other, preferably within three times the Förster distance one with respect to the other, more preferably within two times the Förster distance one with respect to the other, even more preferably within or at the Förster distance one with respect to the other In some cases, the kit comprises: (a) a first primer or probe attached to one first FRET chromophore, wherein the first FRET chromophore is a fluorophore; and (b) a second primer or probe attached to one second FRET chromophore, wherein the first FRET chromophore is different from the second FRET chromophore and wherein the first FRET chromophore and the second FRET chromophore are selected from to form a FRET chromophore pair formed by a FRET donor and a FRET acceptor. In some cases, the second FRET chromophore is another fluorophore.

In some cases the first primer and second primer are forward and reverse primers of a primer pair specific for, and therefore target, one or more polynucleotide analyte or a portion thereof. In particular, in some of those cases, at least one of the first and second primer, preferably both first and second primer are specific for a first genetic variation in at least one polynucleotide analyte. In some of those embodiments, the first primer and second primer specifically bind to target sequences located in the polynucleotide analyte in a region possibly including the first genetic variation such that upon specific binding of the first primer with the target sequence specific for the first primer and upon specific binding of the second primer with the target sequence specific for the second primer the first FRET chromophore and the second FRET chromophore are located within a distance up to four times the Förster distance one with respect to the other.

In some cases the kit further comprises (c) a third primer or probe attached to a third FRET chromophore, and (d) a fourth primer or probe attached to a fourth FRET chromophore, wherein the third FRET chromophore and the third FRET chromophore are selected from to form a FRET chromophore pair formed by a FRET donor and a FRET acceptor. In some cases the third and the fourth primers are specific for one or more polynucleotide analyte or a portion thereof different from the one or more polynucleotide analyte or a portion thereof targeted by the first primer and second primer. In particular in some cases the third and fourth primer are specific for at least one polynucleotide that is different from the at least one polynucleotide analyte targeted by the first and second primers. In some cases, the third and fourth primer are specific for a second genetic variation different from the first genetic variation. In some cases, the second genetic variation can be in the same at least one polynucleotide analyte targeted by the first primer and the second primer. In some cases the second genetic variation can be in a different at least one polynucleotide analyte targeted by the first primer and the second primer.

In some cases, the kit comprises: a plurality of primer pairs each primer pair of the plurality of primer pairs comprising a plurality of primer pairs attaching a plurality of FRET chromophores wherein each primer pair is formed by a forward primer and a reverse primer each attaching a FRET chromophore. In each primer pair the FRET chromophore attached to the forward primer and the FRET chromophore attached to the reverse primer are selected to provide an energy transfer from one to another when located at a Förster distance one with respect to the another thus forming a FRET donor-acceptor chromophore pair. In each primer pair the forward primer has a sequence specific for a target polynucleotide specific for the forward primer within the at least one polynucleotide analyte the reverse primer has a sequence specific for a target polynucleotide specific for the reverse primer within the at least one polynucleotide analyte, the target polynucleotide specific for the forward primer and the target polynucleotide specific for the reverse primer are located within the at least only polynucleotide analyte so that upon specific binding of the forward primer with the target polynucleotide specific for the forward primer and specific binding of the reverser primer with the target polynucleotide specific for the reverse primer, the FRET chromophore attached to the forward primer and the FRET chromophore attached to the reverse primer are located within a distance up to four times the Förster distance one with respect to the other.

In some cases, at least one of the FRET chromophores attached to the forward and reverse primers of a primer pairs is a fluorophore. In some cases, a primer pair of the plurality of primer pairs is specific for a same or different one or more polynucleotide analytes targeted by another primer pair of the plurality of primer pairs. In some cases a primer pair of the plurality of primer pairs is specific for a different genetic variation targeted by another primer pair of the plurality of primer pairs. In some of those cases the genetic variations targeted by primer pairs of the plurality of primers are in a same polynucleotide analytes. In some cases the genetic variation targeted by primer pairs of the plurality of primer pairs are in different polynucleotide analyte.

In some cases, the fluorophore is 6-F AM (Fluorescein), 6-F AM (NHS Ester), Fluorescein dT, HEX, JOE (NETS Ester), MAX, TET, ROX, TAMRA, TARMA (NHS Ester), TEX 615, ATTO 488, ATTO 532, ATTO 550, ATTO 565, ATTO Rho101, ATTO 590, ATTO 633, ATTO 647N, TYE 563, Cy3, Cy5, Alexa Fluor family, TYE 665 or TYE 705. In some cases, a forward primer comprises an oligonucleotide sequence that is specific to a genetic variation. In some of those cases, a corresponding reverse primer comprises an oligonucleotide sequence that is specific to the same genetic variation targeted by the first primer. In some cases, the kit comprises at least three primers, wherein each primer is attached to a different FRET chromophore. In some cases, the kit comprises a set of primers wherein each primer is attached to a FRET donor and acceptor chromophore, respectively. In some cases, the kit does not contain a probe of any kind.

The details of one or more embodiments of the disclosure are set forth in the accompanying drawings and the description below. Other features, objects, and advantages will be apparent from the description and drawings, and from the claims

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

10 uL of 100 uM wild type in one experiment and 10 uL of 1000 uM wild type in the other experiment.

Figure 17:
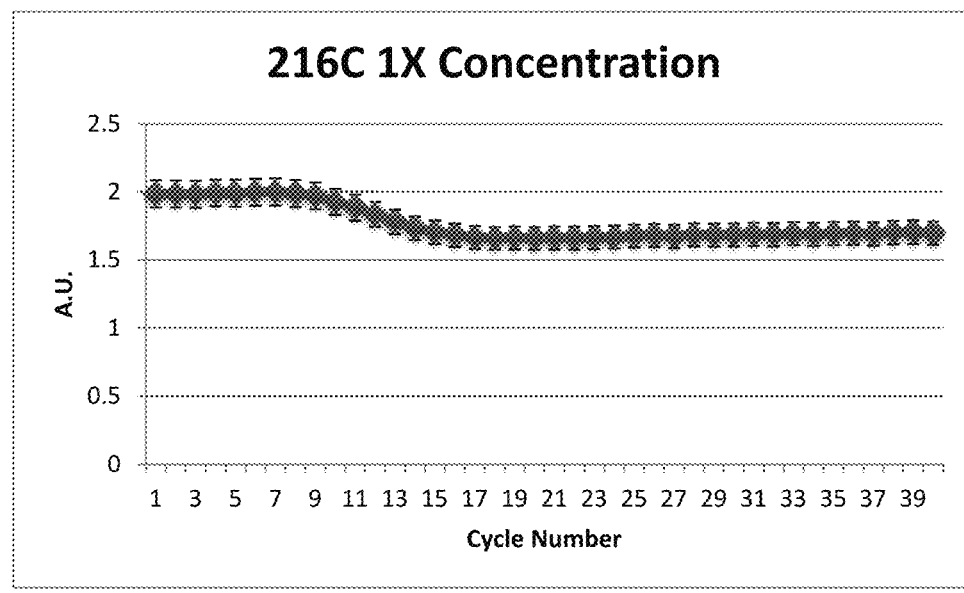

FIG. 17 shows a chart reporting detection of 216C mutant sequence from KRAS gene using quenchiplexing with qPCR. The multiplexed assay contains 0.5 uL of 10 uM forward and reverse primer concentration, 20 uL of Taq 5× mastermix and 10 uL of 10 uM mutant 216C. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ. The amplification phase starts at cycle 8 and the saturation phase at cycle 18.

Figure 18:
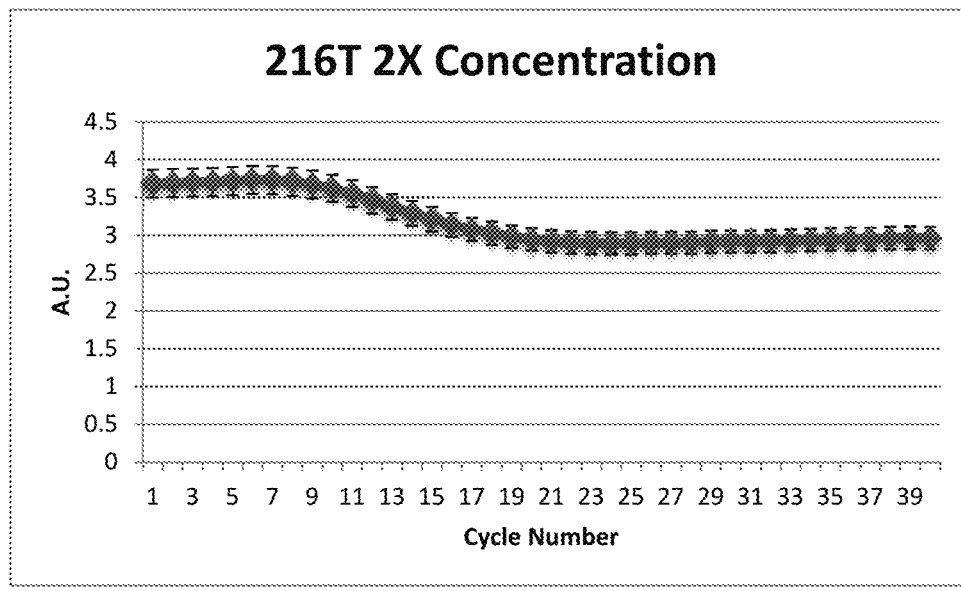

FIG. 18 shows a chart reporting detection of 216T mutant sequence from KRAS gene using quenchiplexing with qPCR. The multiplexed assay contains 1 uL of 10 uM forward and reverse primer concentration, 20 uL of Taq 5× mastermix and 10 uL of 10 uM mutant 216T. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ. The amplification phase starts at cycle 8 and the saturation phase at cycle 20

Figure 19:
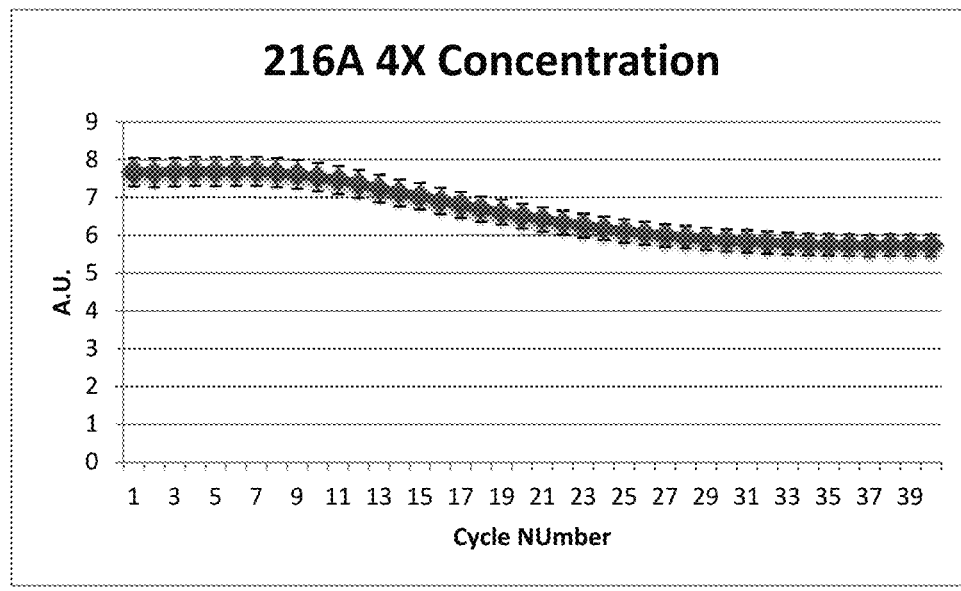

FIG. 19 shows a chart reporting detection of 216A mutant sequence from KRAS gene using quenchiplexing with qPCR. The multiplexed assay contains 2 uL of 10 uM forward and reverse primer concentration, 20 uL of Taq 5× mastermix and 10 uL of 10 uM mutant 216A. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ. The amplification phase starts at cycle 8 and the saturation phase at cycle 32.

Figure 20:
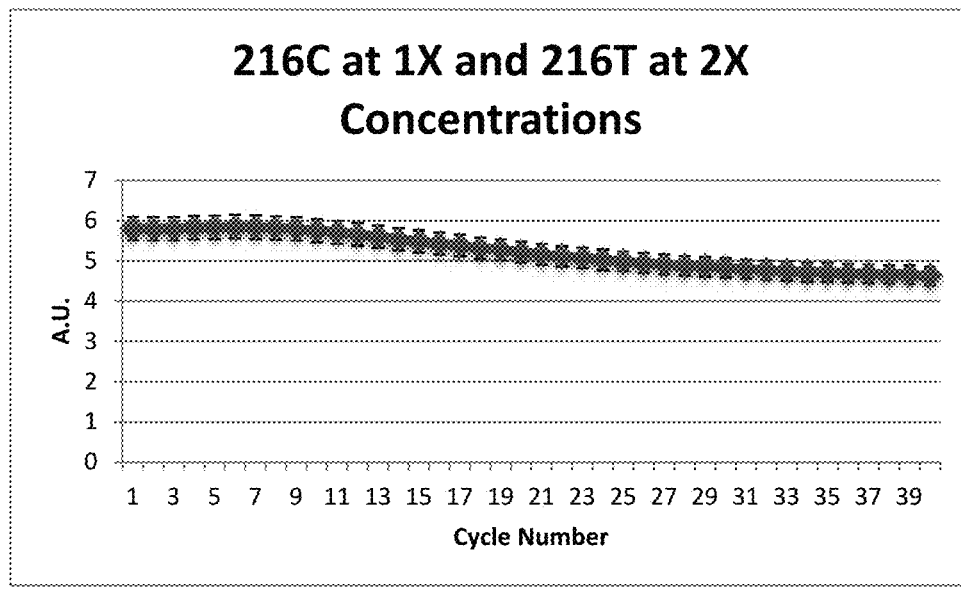

FIG. 20 shows a chart reporting detection of 216C and 216T mutant sequence from K-RAS gene using quenchiplexing with qPCR. The multiplexed assay contains 0.5 uL of 10 uM forward and reverse primer concentration for 216C, 1 uL of 10 uM forward and reverse primer concentration for 216T, 20 uL of Taq 5× mastermix, 10 uL of 10 uM mutant 216C and 10 uL of 10 uM 216T. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ. The amplification phase starts at cycle 9 and the saturation phase at cycle 35.

Figure 21:
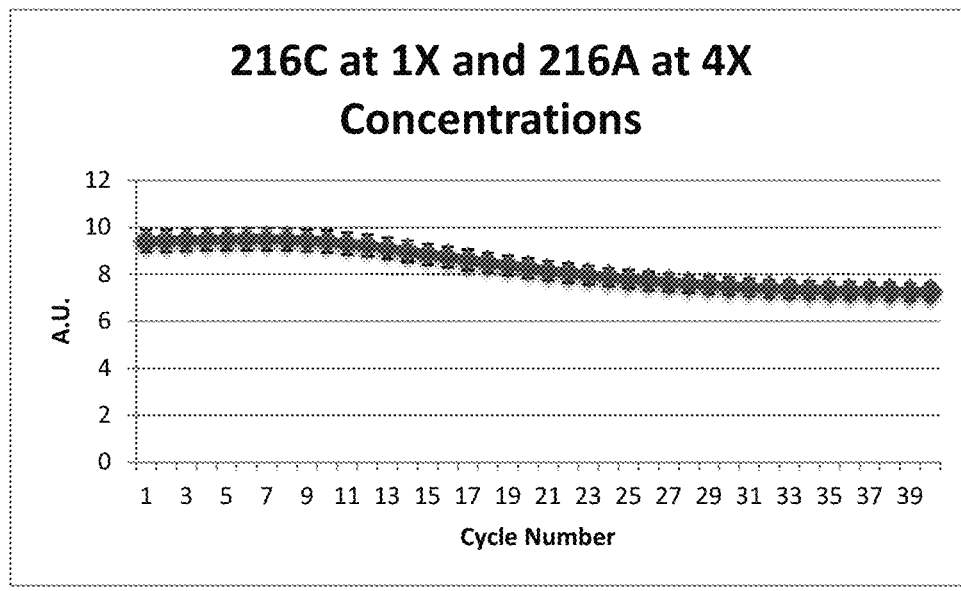

FIG. 21 shows a chart reporting detection of 216C and 216A mutant sequence from K-RAS gene using quenchiplexing with qPCR. The multiplexed assay contains 0.5 uL of 10 uM forward and reverse primer concentration for 216A, 2 uL of 10 uM forward and reverse primer concentration for 216T, 20 uL of Taq 5× mastermix, 10 uL of 10 uM mutant 216C and 10 uL of 10 uM 216A. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ. The amplification phase starts at cycle 11 and the saturation phase at cycle 36.

Figure 22:
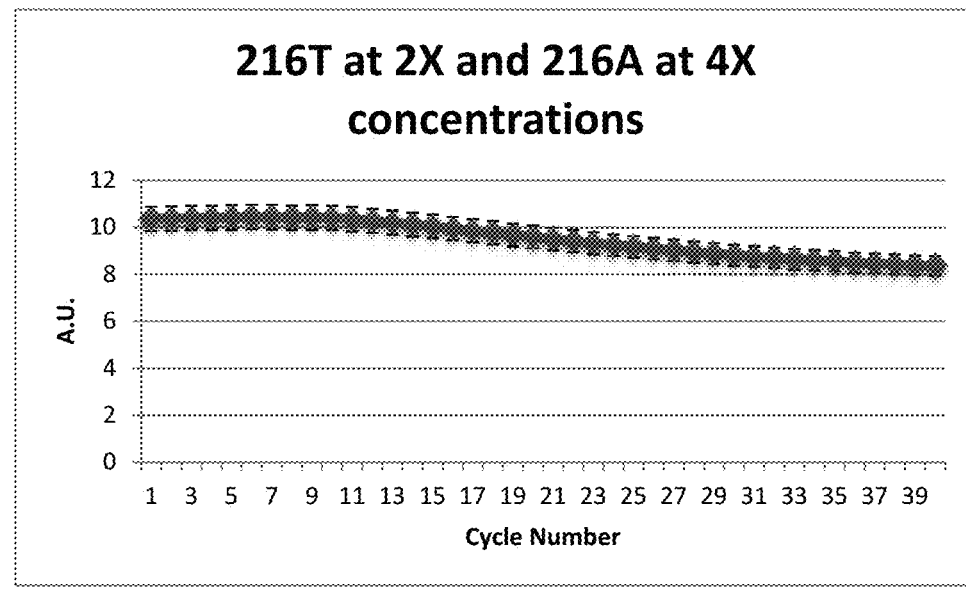

FIG. 22 shows a chart reporting detection of 216T and 216A mutant sequence from K-RAS gene using quenchiplexing with qPCR. The multiplexed assay contains 1 uL of 10 uM forward and reverse primer concentration for 216T, 2 uL of 10 uM forward and reverse primer concentration for 216A, 20 uL of Taq 5× mastermix and 10 uL of 10 uM mutant 216T and 10 uL of 10 uM 216A. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ. The amplification phase starts at cycle 11 and the saturation phase at cycle 38.

Figure 23:
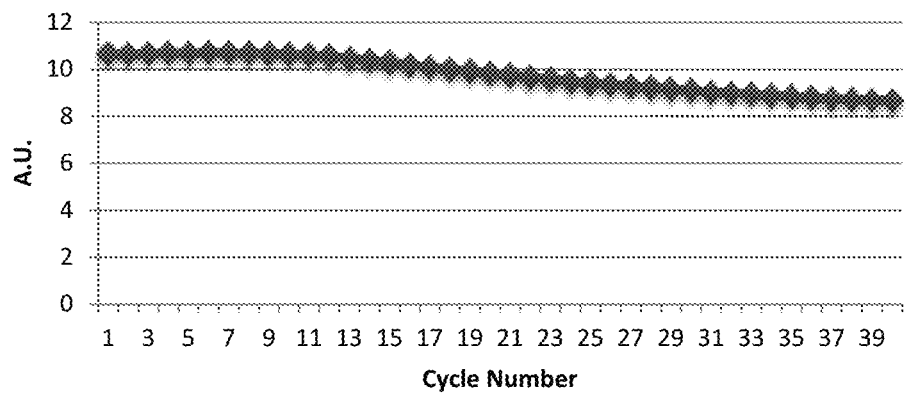

FIG. 23 shows a chart reporting detection of 216C, 216T and 216A mutant sequence from KRAS gene using quenchiplexing with qPCR. The multiplexed assay contains 0.5 uL of 10 uM forward and reverse primer concentration for 216C, 1 uL of 10 uM forward and reverse primer concentration for 216T, 2 uL of 10 uM forward and reverse primer concentration for 216A, 20 uL of Taq 5× mastermix, and 10 uL of 10 uM for each mutant 216C, 216T and 216A. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ. The amplification phase starts at cycle 11 and the saturation phase at cycle 36.

DETAILED DESCRIPTION

Figure 1:
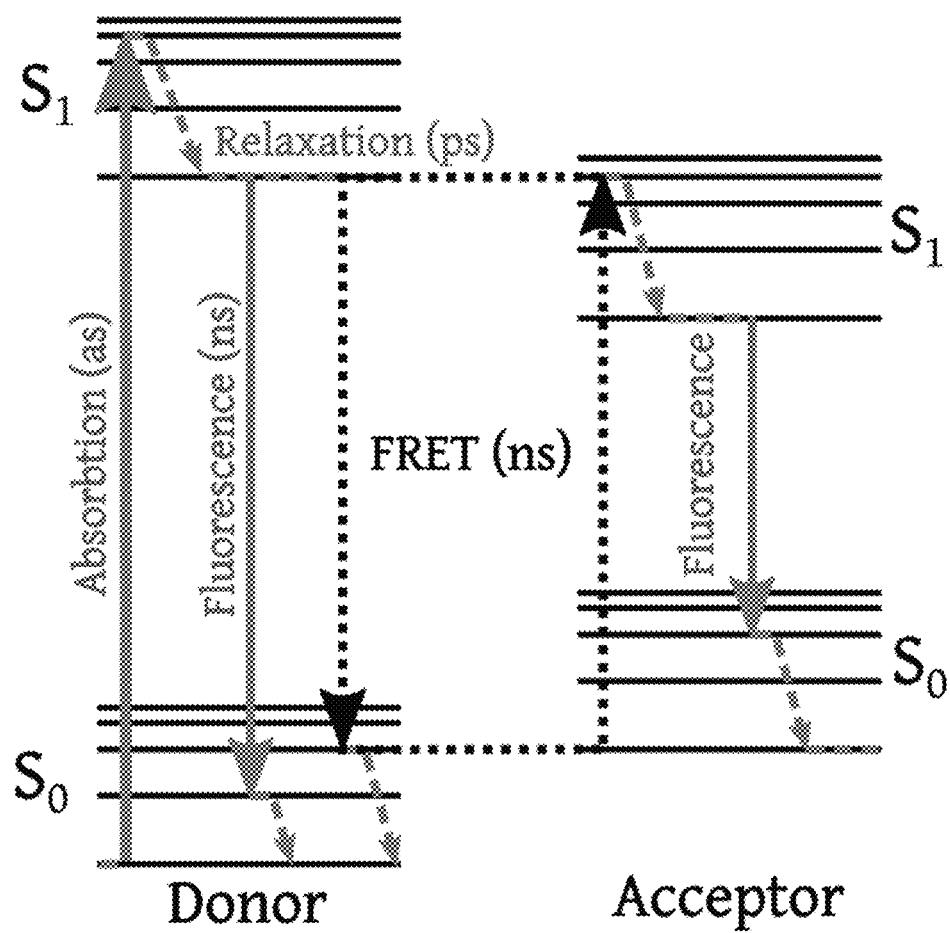
FIG. 1 shows a Jablonski diagram showing Förster resonance energy transfer with typical timescales indicated.

Provided herein are methods, systems, compositions, and kits for the detection of one or more analytes using oligonucleotides (e.g., primers and/or probes) specific for an analyte attaching FRET chromophores. For example, the incorporation of FRET chromophores into an amplification product (e.g., through the use of forward and reverse primers that are attached to different chromophores as illustrated, e.g., in FIG. 1) provides a number of advantages.

For example, methods described herein can provide for the direct detection of one or more analytes in a single reaction. In addition, the direct incorporation of FRET chromophores into the amplification product (e.g., the analyte) allows for more accurate quantification of the analyte and for the real-time monitoring of the progression of an amplification reaction.

Methods described herein are particularly suitable for detecting genetic variations, such as single nucleotide polymorphisms (SNPs) or other qualitative information of an analyte. In some cases, a single base-pair mismatch between a FRET chromophore-labeled primer and the analyte can be detected upon amplification of the analyte. For example, a change in signal may occur if there is a disruption in a contiguous double-stranded DNA sequence upon amplification of the analyte when a SNP is present. A single base pair misalignment (e.g. internal misalignment (such as a SNP) or terminal overhangs) results in significant decrease in signal compared to the signal generated upon amplification of the analyte without a base pair misalignment due to a disruption in electron transport between chromophores incorporated into an analyte containing a base pair misalignment.

Also described herein are methods which allow detection of analytes present in low concentrations. In some cases, the sensitivity of the methods described herein can detect analytes at concentrations of about 10 uM to about 1 aM. In some cases, the methods provided herein can be combined with a digital amplification process (e.g. droplet digital PCR), to further enhance the detection. In some cases, the methods provided herein can be used to detect analytes that are present at a trace concentration in a sample (e.g. a rare SNP).

Further described herein are methods to detect of multiple analytes in a single reaction or experiment, without the need to resort to additional experiments. Thereby, the disclosed methods can reduce or eliminate the associated cost of additional reagents or materials and increase time and efficiency.

The methods and system herein described by using FRET attached to at least one primer in target amplification allows use of a mutation-specific oligonucleotide reducing thus detection that can lead to false positives by mispriming or unrelated hydrolysis. In particular, when both the first and second primers are specific to a genetic variation, a second FRET signal, and in particular a second FRET acceptor signal, is generated only if both primers amplify, which leads to higher specificity compared to traditional allele-specific assays. The methods also avoid the false signal from the excitation light scattering off vessels or samples. In some embodiments herein described the positive identification of a mutation can be simultaneously monitored as an increase in one FRET signal, such as the fluorescence emission signal generated by a FRET acceptor chromophore, and a decrease in another FRET signal, such as the fluorescence emission signal generated by a FRET donor chromophore, thereby increasing reliability and eliminating certain sources of false positives. Additionally, the currently described FRET-based methods and systems are also inherently compatible with commercially available blockers to the wild type, which can be incorporated to work to full effect without adversely affecting the detection and characterization of analytes using FRET-chromophore labeled primers.

I. Certain Terminology

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The term "about," as used herein, generally refers to a range that is 15% greater than or less than a stated numerical value within the context of the particular usage. For example, "about 10" would include a range from 8.5 to 11.5.

The term "primer", as used herein, generally refers to a short linear oligonucleotide that hybridizes to a target nucleic acid sequence (e.g., a DNA template to be amplified) to prime a nucleic acid synthesis reaction. The primer can be an RNA oligonucleotide, a DNA oligonucleotide, or a chimeric sequence. The primer may contain natural, synthetic, or nucleotide analogues (e.g., those that increase $T_m$). Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 3 nucleotides long to about 40 nucleotides long. The "primers" used in the methods of amplification of a target nucleic acid described herein will be of a length appropriate for a particular set of experimental conditions. The determination of primer length is well within the routine capabilities of those of skill in the art.

The terms "polynucleotide," "oligonucleotide," or "nucleic acid," as used herein, are used herein to refer to biological molecules comprising a plurality of nucleotides. Exemplary polynucleotides include deoxyribonucleic acids, ribonucleic acids, and synthetic analogues thereof, including peptide nucleic acids. Polynucleotides can typically be provided in single-stranded form or double-stranded form (herein also duplex form, or duplex).

Additional terminology will be defined in connection with the description of various embodiments of the methods, systems, compositions and kit herein described.

II. Methods of Detection

Described herein are methods for detecting at least one polynucleotide analyte in a sample.

The term "sample" as used herein indicates a limited quantity of something that is indicative of a larger quantity of that something, including but not limited to fluids from a biological environment, specimen, cultures, tissues, synthetic compounds or portions thereof.

The terms "detect" or "detection" as used herein indicates the determination of the existence, presence, absence or features of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal, or to describes distinctive nature, features, or characteristics of the target or signal. Quantitative detection is also referred to as "characterization". A detection is "qualitative" when it refers, relates to, or involves identification of a quality or kind of the target or signal in terms of relative abundance to another target or signal, or the presence or absence of a particular feature, which is not quantified.

In particular, in methods and systems herein described and related compositions and kits, detection and/or characterization of analytes and in particular polynucleotide analytes is performed using FRET-based signal detection.

The term "FRET" refers to Förster Resonance Energy Transfer, a mechanism that describes energy transfer between two light sensitive molecules, such as a donor chromophore and an acceptor chromophore. A donor chromophore initially in its electronic excited state may transfer energy to an acceptor chromophore through non-radiative dipole-dipole coupling. The efficiency of this energy transfer is inversely proportional to the distance between the donor and acceptor, allowing FRET sensitive to small change in distance between the donor and the acceptor chromophores.

The term "FRET donor chromophore", "donor chromophore" or "donor" refers to a chromophore or dye molecule that initially absorbs the energy. The term "FRET acceptor chromophore", "acceptor chromophore" or "acceptor" refers to a chromophore or dye molecule to which the energy is subsequently transferred. The transfer of energy leads to a reduction in the donor's fluorescence intensity and an increase in the acceptor's emission intensity. A pair of chromophores that interact in such a manner that FRET occurs is referred to as a FRET donor-acceptor chromophore pair. Examples of FRET donor and FRET acceptor chromophore include Indocarbocyanine (Cy3)-Indodicarbocyanine (Cy5), Green Fluorescent Protein (GFP)-Yellow Fluorescent Protein (YFP), Yellow Fluorescent Protein (YFP)-Red Fluorescent Protein (RFP) and additional FRET donors and acceptor pairs identifiable by a skilled person.

In embodiments herein described oligonucleotides are labeled with FRET chromophore and are combined with the sample for a time and under conditions to allow hybridization of the FRET labeled oligonucleotides with target sequences located within at least one polynucleotide analyte, in which the hybridization is performed in combinations designed so that emission of a signal by the FRET chromophores or change in such signal provides detection related to at least one analyte polynucleotide based on the following equation:

$$E = \frac{k_{ET}}{k_f + k_{ET} + \Sigma k_i} \quad (1)$$

where
E is the efficiency of energy transfer
$k_{ET}$ is the rate of FRET
$k_f$ is the rate of radiative relaxation (fluorescence)
$k_i$ are the non-radiative relaxation rates (e.g., internal conversion, intersystem crossing, external conversion and additional rates identifiable by a skilled person).
In particular, the FRET efficiency (E) is the quantum yield of the energy transfer transition, i.e. the fraction of energy transfer event occurring per donor excitation event.

Within a point dipole-dipole approximation, the FRET efficiency can be related to the donor-acceptor distance via $$E = \frac{1}{1 + (r/R_0)^6} \quad (2)$$

where r is the separation distance between the donor and the acceptor (FIG. 1) and $R_0$ is the characteristic distance (the Förster distance or Förster radius) at which the energy transfer efficiency is 50%. The FRET efficiency E depends on the donor-to-acceptor separation distance r with an inverse 6th power law due to the dipole-dipole coupling mechanism.

To enhance the FRET efficiency, the donor group should have good abilities to absorb photons and emit photons. That means the donor group should have a high extinction coefficient and a high quantum yield. The overlap of emission spectrum of the donor and absorption spectrum of the acceptor means that the energy lost from excited donor to ground state could excite the acceptor group. The energy matching is called the resonance phenomenon. Thus, the more overlap of spectra, the better a donor can transfer energy to the acceptor. The overlap integral, $J(\lambda)$, between the donor and the acceptor stands for the overlap of spectra, as shown in FIG. 2.

Figure 2:
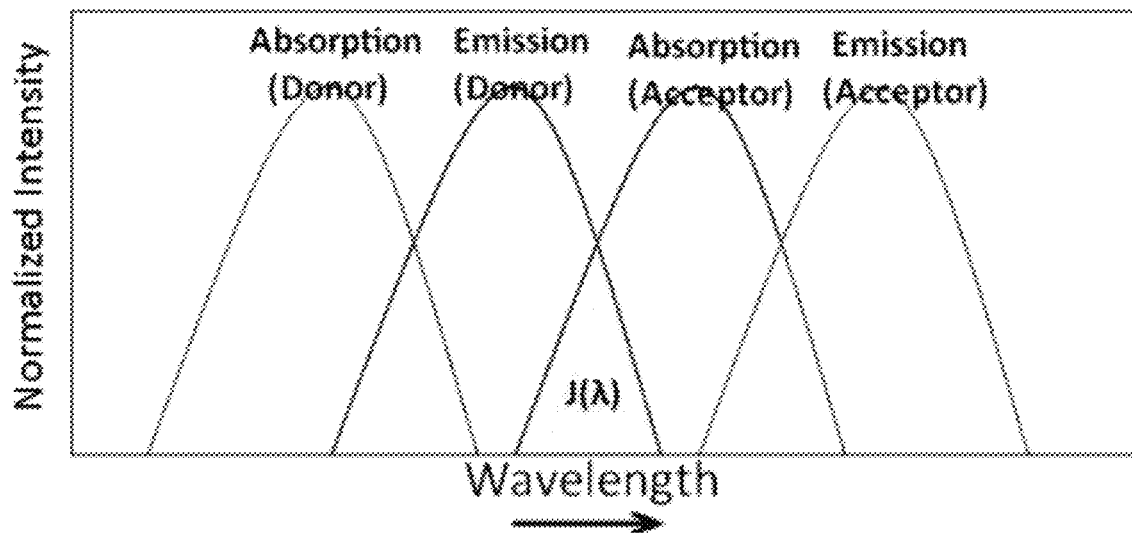
FIG. 2 shows a diagram illustrating spectra of various FRET donor and acceptors where the normalized intensity is plotted versus the wavelength lambda.

In the illustration of FIG. 2, the overlap integral is given by $$J = \int F_D(\lambda)\epsilon_A(\lambda)\lambda^4 d\lambda \quad (3)$$

where $F_D(\lambda)$ is the normalized emission spectrum of the donor. $\epsilon_A$ standards for the molar absorption coefficient of the acceptor. $\lambda$ is the wavelength.

Figure 3:
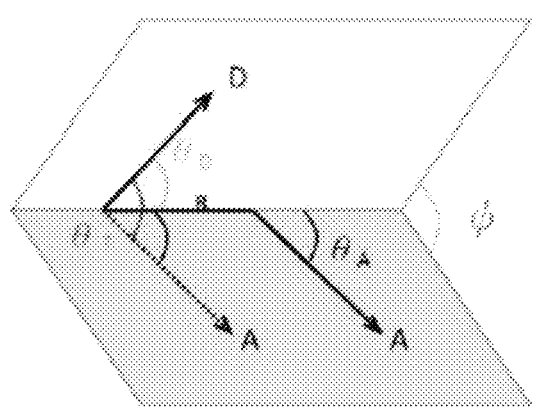
FIG. 3 shows a schematic diagram of the directions of transitions dipoles in energy transfer between FRET donor and FRET acceptor chromophores.

The resonance energy transfer mechanism is also affected by the orientations of the emission transition dipole of the donor and the absorption dipole of the acceptor. The orientation parameter $\kappa^2$ gives the quantitative value of interaction between two dipole moments. $\kappa^2$ can theoretically be values from 0 (when dipoles are perpendicular to each other) to 4 (when dipoles are collinear). $\kappa^2$ is equal to 1 when these two transition dipoles are parallel. The orientation of transition dipoles is shown in FIG. 3. For a freely rotational donor and acceptor group, the average $\kappa^2$ is treated 2/3.

In FRET based detection, a long Förster distance $R_0$ can cause a high FRET efficiency as will be understood by a skilled person. Based on Förster's analysis, $R_0$ is described by the following equation $$R_0^6 = \frac{9 \, Q_0 \, (\ln 10)\kappa^2 \, J}{128 \, \pi^5 \, n^4 \, N_A} \quad (4)$$

where $Q_0$ is the fluorescence quantum yield of the donor in the absence of the acceptor, $\kappa^2$ is the dipole orientation factor, n is the refractive index of the medium, $N_A$ is Avogadro's number, and J is the spectral overlap integral.

Accordingly, in methods and systems herein described and related compositions and kits, FRET chromophore are typically selected in FRET donor-acceptor chromophore pair in which a first FRET chromophore and a second corresponding FRET chromophore are capable of providing an energy transfer from one to another at 50% efficiency when located at a Förster distances one with respect to the another so that one of the first FRET chromophore and second FRET chromophore is the FRET donor of the FRET donor-acceptor chromophore pair and the other of the first FRET chromophore and second FRET chromophore is the FRET acceptor of the FRET donor-acceptor chromophore pair. FRET donor and acceptor chromophore within a same FRET donor-acceptor chromophore pair are herein also indicated as corresponding FRET donor chromophore (or FRET donor) and FRET acceptor chromophore (or FRET acceptor).

Exemplary corresponding FRET donor and acceptors of a FRET donor-acceptor chromophore pair and related Förster distances of is reported in Table 1 below.

TABLE 1

| FRET Donor | Corresponding FRET Acceptor | Förster distance ($R_0$, nm) |
|---|---|---|
| Naphthalene | Dansyl | 2.2 |
| LY | TNP-ATP | 3.5 |
| Dansyl | ODR | 4.3 |
| LY | EM | 5.3 |
| FITC | EM | 6.0 |
| BPE | CY5 | 7.2 |
| Cy3 | Cy5 | 5.6 |

TABLE 1-continued

| FRET Donor | Corresponding FRET Acceptor | Förster distance ($R_0$, nm) |
|---|---|---|
| Fluorescein | TMR | 5.5 |
| Fluorescein | QSY 7 and QSY 9 dyes | 6.1 |
| ATTO488 | ATTO633 | 5.3 |
| ATTO532 | ATTO550 | 6.8 |

Abbreviation:
BPE, B-phycoerythrin;
CY5, carboxymethylindocyanine;
Dansyl, just dansyl group;
EM, eosin maleimide;
FITC, fluorscein-5-isothiocyanate;
LY, Lucifer yellow;
ODR, octadecylrhodamine;
TNP-ATP, trinitrophenyl-ATP.
TMR: Tetramethylrhodamine ATTO488* ATTO532*; ATTO550*; ATTO633*
*related ATTO-TEC webpage at the time of filing In particular, the Förster distance indicated in Table 1 for the exemplary FRET donor-acceptor chromophore pairs of Table 1 is one of the distances were the energy transference from the FRET donor to the FRET acceptor. Occurs. In particular, energy transfer can occur between corresponding FRET donor and acceptor at distances greater than the Förster distance and in particular at a distance up to four times the Förster distance for a particular FRET donor-acceptor chromophore pair, preferably three times the Förster distance, more preferably two times the Förster distance and most preferably at the Förster distance or within the Förster distance.

Accordingly additional distances where energy transfer from the FRET donor to the FRET acceptor of FRET donor-acceptor chromophore pairs of Table 1 or other FRET donor-acceptor chromophore pairs can be identified by a skilled person and include distances up to about 28 nm, preferably equal to or lower than about 20 nm, more preferably equal or lower than about 15 nm and most preferably between about 5 nm and about 15 nm or lower than about 5 nm depending on the FRET donor-acceptor chromophore pair as will be understood by a skilled person.

Additional, corresponding FRET donors and acceptors forming additional FRET donor-acceptor chromophore pairs are identifiable by a skilled person.

In some embodiments, detection methods provided herein may use an amplification technique (e.g., polymerase chain reaction (PCR)) to incorporate FRET chromophores directly onto the product (e.g., an amplicon) based on a template polynucleotide. In some of those embodiments at least one primer used for the amplification, is a FRET labeled oligonucleotide herein described.

In particular, in some embodiments, the method comprises: combining the sample with the at least one pair of primers comprising a forward primer attaching a first FRET chromophore and the reverse primer attaching a second FRET chromophore. In the method, the first FRET chromophore and the second FRET chromophore are selected to be corresponding FRET donor and acceptor chromophores thus forming a FRET donor-acceptor chromophores pair. The method further comprises performing at least one polynucleotide amplification reaction with the forward primer and the reverse primer of the at least one pair of primers. The method also comprises detecting a FRET signal from the sample generated the first FRET chromophore and the second FRET chromophore following the performing. In the method the first primer and second primer specifically bind to target sequences located in the polynucleotide analyte so that upon specific binding of the first primer with the target sequence specific for the first primer, and upon specific binding of the second primer with the target sequence specific for the first oligonucleotide, the first FRET chromophore and the second FRET chromophore are located within four times the Förster distance one with respect to the other, preferably within three times the Förster distance one with respect to the other, more preferably within two times the Förster distance one with respect to the other, even more preferably within or at the Förster distance one with respect to the other.

In particular, in some cases the location of the target sequences can be selected to provide a distance between corresponding FRET donor acceptor chromophore following binding equal to their Förster distance ±0.25 nm to 0.5 nm, or 0.5 nm to 1 nm or 1 nm to 2 nm, depending on the specific FRET donor acceptor chromophore pair as will be understood by a skilled person. In some cases the distance between corresponding FRET donor acceptor chromophore following binding of the related primer pair on respective target sequence is up 30 nm, or equal to or lower than 20 nm, equal or lower than 15 nm, or 10 nm or 5 nm or lower than 5 nm depending on the FRET donor-acceptor chromophore pair and the experimental design.

The conversion between chromophore distance and corresponding base pairs on the target sequences can be performed based on information concerning persistence length of single stranded and double stranded polynucleotide identifiable by a skilled person. For example for DNA this value may be directly measured using an atomic force microscope to directly image DNA molecules of various lengths, or by other techniques such as molecular combing, optical tweezers and additional techniques identifiable by a skilled person. In an aqueous solution, the average persistence length of double strand DNA is 46-50 nm or 140-150 base pairs (the diameter of DNA is 2 nm), although can vary significantly. In comparison, single stranded DNA is known to have persistence length of about 4 nm (see Tinland et al. *Macromolecules*, 1997, 30 (19), pp 5763-5765).

Figure 4:
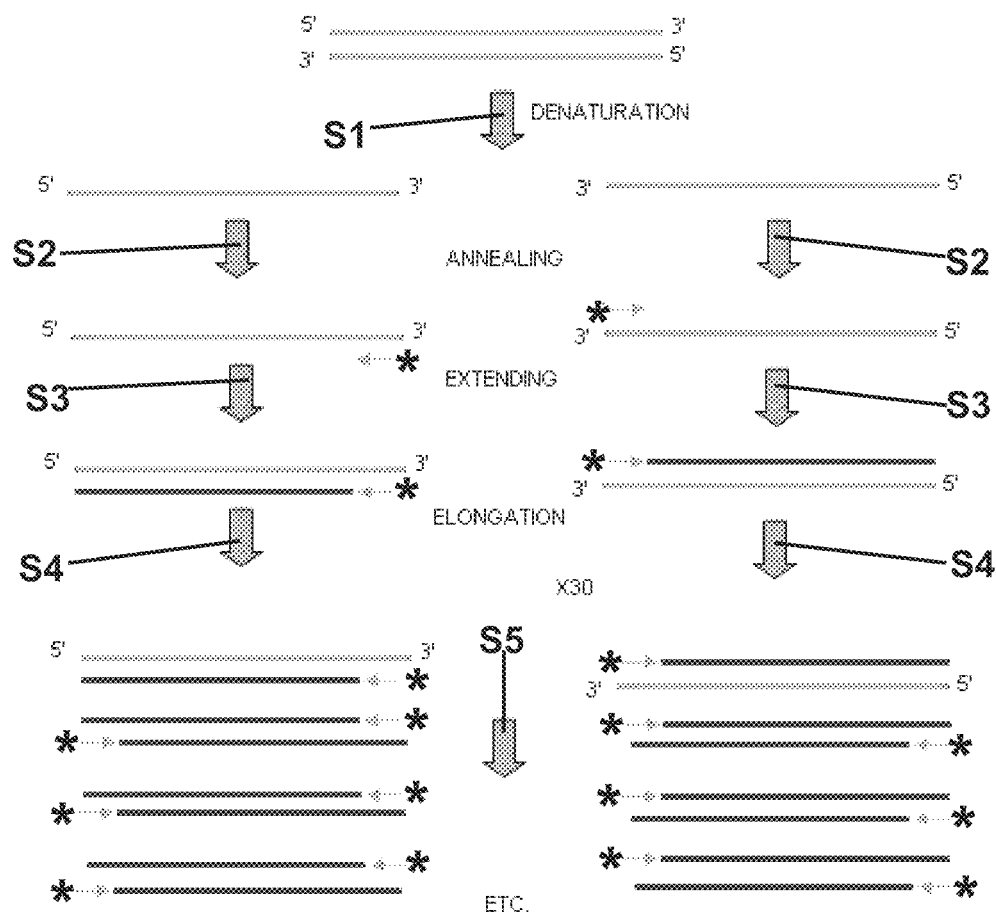
FIG. 4 shows a schematic representation exemplifying amplification of a nucleic acid analyte using FRET labeled-primers (e.g. a FRET donor-attached forward primer and a FRET acceptor-attached to reverse primer). S1 illustrate the denaturation of a double-stranded polynucleotide analyte. S2 illustrate the annealing of the FRET-labeled-primers (indicated in the figure by arrows) to opposite strands of the analyte. S3 and S4 illustrate the elongation process in which polymerase extends the primers during a PCR reaction until providing a complete double stranded polynucleotide. S5 illustrates the formation of a double-stranded PCR product containing both a donor and a receptor which leads to the generation of a fluorescence signal following repeated cycles.

An exemplary illustration of such detection method is shown in FIG. 4, in which a pair of primers, each labeled with either a FRET-donor chromophore or an FRET-acceptor chromophore at its 5' end respectively, is used to detect an analyte by amplification. During the initial amplification cycle, a duplex DNA separates, allowing primers to bind to specific regions of the individual template strands. A polymerase (e.g. Taq polymerase) can be used to extend the primers along the template strand (FIG. 4.S3). A change in signal can be observed after the initial cycle (FIG. 4.S4) in particular when a number of a same template is present in the sample. The intensity of the signal increases as the PCR progresses and the quantity of the amplicons formed following the elongation increases (FIG. 4. S5). This change in signal indicates the presence of the amplified product defined by the primers (e.g. the analyte).

In particular, in some cases exemplified in FIG. 4, primers used in embodiments herein described are formed by a forward primer and a reverse primer used in combination to form a pair of primers or primers pair. The term "forward primer" is a primer that is complementary and anneals to the 5' end of the 5'->3' strand of a double-stranded polynucleotide analyte. The term "reverse primer" is a primer that is complementary and anneals to the 5' end of the complementary 3'->5' strand of the double-stranded polynucleotide analyte.

The term "complementary" as used herein indicates a property of single stranded polynucleotides in which the sequence of the constituent monomers on one strand chemically matches the sequence on another other strand to form a double stranded polynucleotide. Accordingly two polynucleotides having chemically matching sequences are herein also indicated as "self-complementary".

A "single-stranded polynucleotide" refers to an individual string of monomers linked together through an alternating sugar phosphate backbone. In particular, the sugar of one nucleotide is bond to the phosphate of the next adjacent nucleotide by a phosphodiester bond. Depending on the sequence of the nucleotides, a single-stranded polynucleotide can have various secondary structures, such as the stem-loop or hairpin structure, through intramolecular self-base-paring. A hairpin loop or stem loop structure occurs when two regions of the same strand, usually complementary in nucleotide sequence when read in opposite directions, basepairs to form a double helix that ends in an unpaired loop. The resulting lollipop-shaped structure is a key building block of many RNA secondary structures. The term "small hairpin RNA" or "short hairpin RNA" or "shRNA" as used herein indicate a sequence of RNA that makes a tight hairpin turn and can be used to silence gene expression via RNAi.

A "double-stranded polynucleotide" refers to two single-stranded polynucleotides bound to each other through complementarily binding. The duplex typically has a helical structure, such as double-stranded DNA (dsDNA) molecule, is maintained largely by non-covalent bonding of base pairs between the strands, and by base stacking interactions.

Chemical matching between complementary single strand polynucleotides indicates that the base pairs between the monomers of a single strand polynucleotide can be non-covalently connected via two or three hydrogen bonds with corresponding monomers in the complementary single strand polynucleotide. In particular, in this application, when two polynucleotide strands, sequences or segments are noted to be complementary, this indicates that they have a sufficient number of complementary bases to form a thermodynamically stable double-stranded duplex. Double stranded of complementary single stranded polynucleotides include dsDNA, dsRNA, DNA: RNA duplexes as well as intramolecular base paring duplexes formed by complementary sequences of a single polynucleotide strand (e.g. hairpin loop) complementarily binding one with another.

The term "complementarily bind", "complementary bind", as used herein with respect to nucleic acids indicates the two nucleotides on opposite polynucleotide strands or sequences that are connected via hydrogen bonds to form a "base pair", a "complementary base pair". For example, in the canonical Watson-Crick DNA base pairing, adenine (A) forms a base pair with thymine (T) and guanine (G) forms a base pair with cytosine (C). In RNA base paring, adenine (A) forms a base pair with uracil (U) and guanine (G) forms a base pair with cytosine (C). Accordingly, the term "base pairing" as used herein indicates formation of hydrogen bonds between base pairs on opposite complementary polynucleotide strands or sequences following the Watson-Crick base pairing rule as will be applied by a skilled person to provide duplex polynucleotides. Accordingly, when two polynucleotide strands, sequences or segments are noted to be binding to each other through complementarily binding or complementarily bind to each other, this indicate that a sufficient number of bases pairs forms between the two strands, sequences or segments to form a thermodynamically stable double-stranded duplex, although the duplex can contain mismatches, bulges and/or wobble base pairs as will be understood by a skilled person.

The term "thermodynamic stability" as used herein indicates a lowest energy state of a chemical system. Thermodynamic stability can be used in connection with description of two chemical entities (e.g. two molecules or portions thereof) to compare the relative energies of the chemical entities. For example, when a chemical entity is a polynucleotide, thermodynamic stability can be used in absolute terms to indicate a conformation that is at a lowest energy state, or in relative terms to describe conformations of the polynucleotide or portions thereof to identify the prevailing conformation as a result of the prevailing conformation being in a lower energy state. Thermodynamic stability can be detected using methods and techniques identifiable by a skilled person. For example, for polynucleotides thermodynamic stability can be determined based on measurement of melting temperature $T_m$, among other methods, wherein a higher $T_m$ can be associated with a more thermodynamically stable chemical entity as will be understood by a skilled person. Contributors to thermodynamic stability can comprise chemical compositions, base compositions, neighboring chemical compositions, and geometry of the chemical entity.

In particular, in embodiments herein described the forward primer and a reverse primer used in combination in methods herein described are designed to specifically bind target sequences within the at least one polynucleotide analyte.

The wording "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions etc. The term "specific" as used herein with reference to a molecular component of a complex, refers to the unique association of that component to the specific complex which the component is part of. The term "specific" as used herein with reference to a sequence of a polynucleotide refers to the unique association of the sequence with a single polynucleotide which is the complementary sequence. By "stable complex" is meant a complex that is detectable and does not require any arbitrary level of stability, although greater stability is generally preferred.

In embodiments herein described oligonucleotides and in particular primers of primer pairs are designed to attach a donor and acceptor of a FRET donor-acceptor chromophore pair, and to specifically bind to target sequences within one or more target polynucleotide analyte selected so that when the primers specifically bind to the corresponding target sequence, the primers present the FRET donor and acceptor at a distance up to four times the Förster distance for that FRET donor-acceptor chromophore pair.

As used herein, the term "corresponding" in connection with molecules refers to the binding a molecule to another molecule. The term "corresponding" used in connection with sequences refers to the complementarity of a sequence with respect to another and the related ability to complementarily bind. Thus, polynucleotides that complementarily bind one to the other are indicated as corresponding. Also the sequences of polynucleotides complementary one to the other are indicated as corresponding sequences and can be provided in corresponding polynucleotides. The term "corresponding" in connection with FRET chromophores indicates FRET donor and acceptor chromophore capable of providing an energy transfer from the FRET donor to the FRET acceptor when located at Förster distance one with respect to the other.

The term "present" as used herein with reference to a compound or functional group indicates attachment performed to maintain the chemical reactivity of the compound or functional group as attached. Accordingly, a functional group presented on a ligand, is able to perform under the appropriate conditions the one or more chemical reactions that chemically characterize the functional group.

Accordingly, following selection of target sequences in one or more polynucleotide analytes to have a distance up to four times the Förster distance upon binding of primers in accordance with an experimental design, the primers (and/or other oligonucleotides) are built to specifically bind to the target sequences with a similar thermodynamic stability (e.g. with a Tm within 5° C., preferably between lower than 5° C., more preferably within 1-2° C. and most preferably within 0.5 and 1° C.).

In particular, in some cases, a primer and/or other oligonucleotides herein described are specific for at least one polynucleotide analyte and/or a variation thereof. In those cases, the primer and/or other oligonucleotides are complementary and specifically bind a corresponding recognition sequence in single stranded target polynucleotides within the at least one polynucleotide analyte.

A "recognition sequence" is a sequence that is configured to set apart or identify a polynucleotide or sequence thereof from others in a sample. Therefore a recognition sequence for a polynucleotide or for a variation thereof indicates a sequence that provides a characteristic mark, an identifier capable to mark the polynucleotide as unique and set the item apart from others, in a particular sample.

In particular, the primer and/or other oligonucleotide typically comprises a recognition region complementary and capable of specifically binding the recognition sequence on the corresponding single strand target polynucleotide. The recognition region in cases herein described is preferably located on the 3' end of the primer or other oligonucleotide, in particular when the FRET chromophore is located at the 5' end of the primer or other oligonucleotide The terms "5' end" and "3' end" of a polynucleotide indicate the two ends of the polynucleotide encompassing the terminal residues of the polynucleotides and are distinguished based on the nature of the free group on each extremity. The 5'-end designates a portion of the polynucleotide strand that has the fifth carbon in the sugar-ring of the deoxyribose or ribose at its terminus (5' terminus). The 3'-end of a strand designates a portion of the polynucleotide strand terminating at the hydroxyl group of the third carbon in the sugar-ring of the nucleotide or nucleoside at its terminus (3' terminus). The 5' end and 3' end and in particular the 5' terminus and 3' terminus in various cases can be modified chemically or biologically e.g. by the addition of functional groups or other compounds as will be understood by the skilled person. In some cases the 5' end encompasses a portion from the 5' terminus to a residue approximately in the middle of the primer or oligonucleotide (e.g. approximately 10 bases in a primer of 20 bases) In some cases the 3' end encompasses a portion from the 3' terminus to a residue approximately in the middle of the primer or oligonucleotide (e.g. approximately 12 bases in a primer of 25 bases).

In embodiments where at least one primer pair is used to detect at least one polynucleotide analyte or a variation thereof (e.g. a genetic variation) in each primer pair used each of the forward primer and the reverse primer of the primer pair typically comprises a recognition region complementary and capable of specifically binding a corresponding recognition sequence on the corresponding single strand target polynucleotide to which each of the forward primer and the reverse primer specifically binds.

In preferred cases the recognition region is located within the 3' end of the forward primer and/or the reverse primer.

In particular, in embodiments where investigation of a variation of polynucleotide analyte sequences is desired and in particular a genetic variation such as a SNP or deletion or insertion is desired, the target sequence is selected in a region of the target polynucleotide including a recognition sequence for the variation, and the primer can be selected and designed to specifically bind to the recognition sequence, preferably through a recognition region in the terminal portion at the 3' end of the primer (or of other oligonucleotide).

In several cases primers can be 20-35 base pair depending on the sequences of the target the sequence of the primer and the experimental conditions as will be understood by a skilled person.

In embodiments herein describe each of the primers (or other oligonucleotides) are labeled with the FRET chromophore based on the specific target sequence and Förster distance for the related FRET donor-acceptor chromophore in a configuration that allow presentation of the FRET chromophore following binding of the primer (or other oligonucleotide) to the target sequence in an orientation allowing energy transfer with the corresponding FRET label of the FRET donor-acceptor chromophore pair. In some cases, each primer attaches a plurality of FRET label of a same type (e.g. a plurality of donors or a plurality of acceptor) can be used on a same primer or oligonucleotide.

The term "attach" or "attached" as used herein, refers to connecting or uniting by a bond, link, force or tie in order to keep two or more components together, which encompasses either direct or indirect attachment where, for example, a first molecule is directly bound to a second molecule or material, or one or more intermediate molecules are disposed between the first molecule and the second molecule or material. In some embodiments, the primer (or other oligonucleotide) attaches the FRET chromophore by direct covalent attachment. In some cases, the primer (or other oligonucleotide) indirectly through binding with other molecule (e.g. aptamers or other synthetic recognition molecules)

In several embodiments, the FRET chromophore is attached within the 5' end of the primer or other oligonucleotide. In particular, the FRET chromophore can be attached within approximately 10 bases from the 5' terminus of the primer or other oligonucleotide, possibly within 5 bases from the 5' terminus of the primer or other oligonucleotide. Preferably the FRET chromophore can be attached at the 5' terminus of the primer.

In methods herein described amplification is then performed and measuring a signal can be performed before and/or after each step according to the experimental design. Typically, measuring is performed at least following annealing of at least one amplification cycle by measuring at least an acceptor signal from a FRET acceptor chromophore alone or in combination with measuring of a FRET donor signal from the corresponding FRET donor. In some cases the measuring following annealing of the primers can also be preceded by an optional measuring of the donor and/or acceptor of the FRET donor-acceptor chromophore before the amplification cycle. In some cases measuring before amplification cycle is performed by measuring a donor signal of the FRET donor-acceptor chromophore pair (or other primer/oligonucleotide pairing herein described) and possibly an acceptor signal of the FRET donor-acceptor chromophore pair. In some cases, several amplification cycles can be performed and the measuring of the FRET signal can be performed before and/or after annealing of one or more amplification cycles.

In embodiments where a specific binding of the primer pairs (or binding of other oligonucleotide) occurs, a successful binding of the primers to the corresponding target sequences and in particular to the recognition sequences of through specific binding of corresponding recognition region, is detectable by a change in signals detected before and after at least one cycle of amplification possibly after each of a plurality of amplification cycles, and/or in by a change in signals detected after each amplification cycle.

In some cases, the change in signal is an increase in signal (e.g., an increased fluorescence emission intensity of the FRET acceptor chromophore of a FRET donor-acceptor chromophore pair when a donor chromophore and an acceptor chromophore are incorporated into the amplified product). In some case, the change in signal is a decrease in signal (e.g., a decreased fluorescence emission intensity of the FRET donor chromophore of a FRET donor-acceptor chromophore pair when a donor chromophore and an acceptor chromophore are incorporated into the amplified product). In some cases, the increase in one signal indicates a presence of the product or analyte. In some cases, the decrease in another signal indicates a presence of the product or analyte. In some cases, the lack of a change in signal (e.g., no significant change in fluorescence intensity) indicates the absence of the product or analyte. For example, in the cases when the Cy3-Cy5 pair is used as a FRET donor-acceptor chromophore pair, in which Cy3 is attached to a first primer as a FRET donor chromophore, Cy5 is attached to a second primer as a FRET acceptor chromophore, and the first primer and second primer constitute a primer pair. Before the primers bind to a template strand, Cy3 emits yellow light and Cy5 produces low emission signal in red. After the primers bind and are subsequently extended along the template strand, FRET occurs between Cy3 and Cy5, resulting in a decrease in the yellow emission by Cy3 accompanied by an increase in the red emission by Cy5. The change in fluorescence emission signal can be measured at the optimal excitation and emission wavelength of the donor Cy3 and the acceptor Cy5, respectively.

In some cases, the change in signal can be defined by a percentage change. In some cases, the change in signal can be about 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900%, 1000% or more. In some cases, the change in signal can be greater than 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900% or 1000%. In some cases, the change in signal can be less than 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900% or 1000%. In some cases, the change in signal can be about 50%. In some cases, the change in signal indicates the presence of the product. In some cases, the increase in one FRET signal indicates the presence of the product. In some cases, the decrease in another FRET signal indicates the presence of the product.

In some cases one or more primers attaching FRET chromophores can be used together with oligonucleotides attaching a FRET chromophore used as probes where the FRET chromophore are selected to form upon binding a FRET donor-acceptor FRET chromophore pair. The term "probe" or "hybridization probe", as used herein, generally refers to a fragment of linear oligonucleotide of variable length that is used in samples containing DNA, RNA or any synthetic molecule that resembles DNA or RNA to detect the presence of target nucleotide sequences that are complementary to the sequence in the probe.

In particular in some cases at least one primer attaching a first FRET chromophore and/or at least one probe attaching a second FRET chromophore of a FRET chromophore pair can be used in combinations where the detection is performed following presence, absence or change of a signal from a FRET chromophore. In some cases, at least one primer-attaching a FRET chromophore is used with a probe or a plurality of probes attaching a FRET chromophore. In some cases, a plurality of primers attaching FRET chromophores is used with a plurality of probes attaching FRET chromophores. In some cases, a plurality of primers attaching FRET chromophores is used with a single probe attaching a FRET chromophore. In some cases, a primer pair attaching FRET chromophores is used to detect an analyte. In some cases, a primer pair attaching a FRET donor-acceptor chromophore pair is used to detect multiple analytes. In some cases, a plurality of primer pairs attaching a each attaching a FRET donor acceptor chromophore pair are used to detect an analyte. In some cases, a primer and a probe is used to detect an analyte. In some cases, a primer attaching a FRET chromophore (e.g. a donor) and a probe attaching a corresponding FRET chromophores (e.g. the acceptor of a same FRET donor-acceptor chromophore pair of the donor attached to the primer) is used to detect multiple analytes. In some cases, a combination of primers attaching FRET chromophores and probes attaching FRET chromophores is used to detect an analyte. In some cases, a combination of primers attaching FRET chromophores and probes attaching FRET chromophores is used to detect multiple analytes with each target identified by a separate pair of primer-probe. In some cases, a probe attaching FRET chromophores is used to detect an analyte presenting another FRET label forming a FRET donor-acceptor chromophore pair.

In embodiments where detection of a polynucleotide analyte and in particular of a genetic variation in the polynucleotide analyte is desired the target sequences for the primer pair or primer-probe pair specific for the genetic variation are complementary for at least a portion of the recognition sequence for the genetic variation (e.g. in their 3' ends for at least 1 bp). (see Examples 3 and 4).

In preferred embodiments, at least a portion of the recognition sequence on the single strand target polynucleotide specific for a forward primer of a primer pair is complementary to a corresponding portion of the recognition sequence of the single strand target polynucleotide specific for the reverse primer on the same polynucleotide analyte. In those embodiments, the recognition sequence of the single strand target polynucleotide specific for a forward primer and the recognition sequence of the single strand target polynucleotide specific for a reverse primer are at least partially self-complementary. In those embodiments, the forward and reverse primer of the primer pair are complementary to corresponding recognition sequences and are therefore at least in part self-complementary.

In some embodiments, the recognition sequence of the single strand target polynucleotide specific for the forward primer, and the corresponding portion of the recognition sequence of the sequence of the single strand target polynucleotide specific for the reverse prime are self-complementary for a sequence equal to or less than 20 bases and each of the recognition regions of the forward primer and reverse primer is within 20 bases from the respective 3' terminus. In particular, in some cases the recognition sequences can be for a genetic variation selected from a substitution, an addition, a deletion or a translocation.

In some embodiments, the recognition sequence on the single strand target polynucleotide specific for the forward primer, and the corresponding portion of the recognition sequence on the single strand target polynucleotide specific for the reverse prime are self-complementary for a sequence of 1 base. In some cases, each of the recognition regions of the forward primer and reverse primer are possibly within 1 to 3 bases from the respective 3' terminus. In particular, in some cases the recognition sequences can be for a genetic variation selected from a substitution, an addition, a deletion or a translocation and in particular a single-nucleotide polymorphism (SNP).

In some cases of genetic variation, one or more bases are inserted into a target sequence, resulting in a shift in the reading frame. In such cases, FRET-chromophore-labeled primers can be designed to include a recognition region at the 3' end specific for the inserted bases for detecting the presence or absence of such insertion. Such FRET-based qPCR applications can be used for inherited mutation detection, such as insertions in p53 family genes. Each of the recognition region of the forward primer and reverse primer is preferably located at the respective 3' terminus.

In embodiments where detection of a plurality of analytes is performed possibly comprising a genetic variation a plurality of FRET labeled primer pairs each attaching a FRET donor-acceptor chromophore pair can be used with each pair specific for one polynucleotide analyte and/or a single variation within one or more polynucleotide analyte.

In those embodiments, a plurality of primer and/or probe pairs can be used to perform the detection, each pair attaching corresponding FRET donor-acceptor chromophores.

In some cases, a FRET-chromophore-labeled probe is used to detect multiple analytes presenting one or more FRET labels. In some cases, multiple FRET-chromophore-labeled probes are used to detect an analyte. In some cases, a single FRET donor/acceptor chromophore pair is used to detect an analyte. In some cases, a single FRET donor/acceptor chromophore pair is used to detect multiple analytes. In some cases, multiple FRET donor/acceptor chromophore pairs are used to detect an analyte. In some cases, the signal is not limited to a signal generated by a FRET donor/acceptor chromophore pair. In some cases, the signal can be generated by different chromophores.

In some cases, a plurality of FRET-chromophore-labeled primers is used in the detection methods. In some cases, a FRET-chromophore-labeled primer is used with a FRET-chromophore-labeled probe or a plurality of FRET-chromophore-labeled probes. In some cases, a FRET-chromophore-labeled primer is used without any type of probe. In some cases, a plurality of FRET-chromophore-labeled primers are used with a plurality of FRET-chromophore-labeled probes. In some cases, a plurality of FRET-labeled primers are used with a single FRET-chromophore-labeled probe. In some cases, a plurality of FRET-chromophore-labeled primers are used without any type of probe.

In some embodiments, a plurality of primer and/or probe pairs attaching a same FRET donor acceptor chromophore pair are used in methods herein described wherein the primers are added at different concentrations and the signal measured after annealing of at least one, preferably multiple amplification cycles (e.g. an acceptor signal measured alone or in combination with a donor signal) can be used to form signature profile for the at least one polynucleotide and/or at least one variation thereof.

In some embodiments, a plurality of primer and/or probe pairs each attaching a different FRET donor acceptor chromophore pair are used in methods herein described wherein a same or different concentration of each primer pair is used and the signal measured after annealing of at least one, preferably multiple amplification cycles (e.g. an acceptor signal measured alone or in combination with a donor signal) can be used to form signature profile for the at least one polynucleotide and/or at least one variation thereof as will be understood by a skilled person.

In some embodiments, the measured FRET signals before and/or after annealing in each cycle can be traced to form a profile (e.g. a real-time curve) that can be used for detection (e.g. quantitative measurement) of the target polynucleotide analyte or portion thereof, and in particular a variation and in particular a genetic variation thereof.

In some cases, a signature profile is used to detect the presence of a SNP in a sample containing a plurality of polynucleotide analytes. In some cases, the signature profile for each SNP of the plurality of analytes is a curve having the x-axis represented by the number of PCR cycles and the y-axis represented by the emission intensity generated by the FRET acceptor of at least one FRET chromophore pair attached to the primer pair that is specific for that particular SNP. The signature profile can be obtained for each single nucleotide mismatch and/or combinations thereof.

In particular in embodiments where different concentration of primer pairs of a plurality of primers are used, the concentration can be selected so that a certain concentration identifies one primer pair or a combination thereof.

Additional profiles and related applications are described in the Examples section and can be identified by a skilled person upon reading of the present disclosure.

In some cases, the method is used with a second method. In some cases, the second method is an amplification method. In some cases, the amplification method is an isothermal reaction method or a polymerase chain reaction method. In some cases, the polymerase chain reaction is a multiplex-PCR, a quantitative PCR (qPCR), an end point PCR or a digital PCR (e.g. droplet digital PCR). In some cases, the polymerase chain reaction is a droplet digital PCR. In some cases, the second method is a droplet digital PCR method. In some cases, the method is used in combination with a second and a third method. In some cases, the third method is an amplification method, an electrophoresis (e.g. gel electrophoresis, capillary electrophoresis), a mass spectroscopy method, a chromatography method or an assay (e.g. in vitro cell based assay).

A. Detection of Analytes from Intensity-Length Relationship

Described herein is a method of detecting the presence of one or more analytes in a sample. Methods provided herein involve, e.g., the measurement of the change in signal intensity when at least two chromophores interact with each other. For example, in the case of a FRET donor and FRET acceptor chromophore interaction, the closer the donor is from the acceptor, the brighter the fluorescence signature of a particular nucleic acid analyte will typically be. So long that the analyte lengths are small, the persistence length of the nucleic acid analyte typically determines the intensity of fluorescence. For example, for a given donor-acceptor pair, the intensity of the fluorescence can be correlated with the persistence length. Further, the intensity of fluorescence often indicative of an energy transfer between the donor and the acceptor. The efficiency of this energy transfer is described by the following equation:

$$E = \frac{1}{1 + (r/R_0)^6} \quad (2)$$

where r is the distance between the donor and the acceptor (FIG. 1) and $R_0$ is the characteristic distance (the Förster distance or Förster radius), with a 50% transfer efficiency which is a constant related to each donor/acceptor pair that can be calculated from certain parameters of the absorption and emission spectra of each chromophore. (See Biophysical Chemistry, D. Freifelder, ed., W.H. Freeman and Company, San Francisco (1976) at page 426-28). Further, $R_0$ is described by the following equation:

$$R_0^6 = \frac{9\ Q_0\ (\ln 10)\kappa^2\ J}{128\ \pi^5\ n^4\ N_A} \quad (4)$$

where $Q_0$ is the fluorescence quantum yield of the donor in the absence of the acceptor, $\kappa^2$ is the dipole orientation factor, n is the refractive index of the medium, $N_A$ is Avogadro's number, and J is the spectral overlap integral.

Therefore positioning of FRET labels within a distance up to four times the Förster distance will result in transfer of energy and emission of a signal by the FRET acceptor. Therefore, the changes in fluorescence intensity typically vary with the length of the synthesized strand. In some cases, an increase in fluorescence intensity is accompanied by the decrease with the length of the synthesized strand. Utilizing this relationship, the presence of an analyte can be detected based on the intensity correlated with its length. For example, a set of fluorescence intensity ladders reminiscent of molecular weight ladders based on DNA length can be established as a control. In a sample, multiple pairs of primers labeled with the same donor/acceptor pair are amplified. Upon completion of the amplification process, the observed intensities can be correlated with the controls, thereby detecting a particular analyte. In some cases, the presence or absence of a particular analyte can be monitored throughout the amplification process, by taking measurements during each amplification cycle and comparing with the control ladder. In some cases, the ladder comprises a plurality of signals. In some cases, the plurality of signals generates multiple curves. In some cases, the ladder is represented by a plurality of curves. In some cases, the ladder comprises multiple sets of initial and end points. In some cases, each step of the ladder comprises a plurality of signals. In some cases, the plurality of signals generates a curve. In some cases, each step of the ladder is represented by a curve. In some cases, each step of the ladder comprises a set of initial and end points. In some cases, the curve represents a signature profile of an analyte based on its length. In some cases, the set of initial and end points represents a signature profile of an analyte based on its length. In some cases, each step of the ladder generates a signature profile of an analyte based on its length. In some cases, the ladder comprises multiple steps or multiple signature profiles of analytes. In some cases, the ladder comprises a single step or a single signature profile of an analyte. In some cases, the ladder comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500 or more steps. In some cases, the ladder comprises more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500 steps. In some cases, the ladder comprises less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450 or 500 steps. In some cases, multiple analytes are detected by a single FRET donor/acceptor pair. In some cases, a single analyte is detected by a single FRET donor/acceptor pair. In some cases, the signal is not limited to a signal generated by a donor and acceptor pair. In some cases, the signal can be generated by different donor/acceptor chromophores.

B. Detection of Genetic Variations

Disclosed herein is a method of determining the presence or absence of a genetic variation, e.g., based on the change in signal intensity due, e.g., to a disruption in the electron transport mechanism described herein. Genetic variations include deletion and insertion of one or more nucleotides, translocations different nucleotide occurrences (e.g. single point mutations such as SNPs or a base-pair substitution), or variations in the number of multiple nucleotide repetitions. For example, to detect the presence of a single deletion or alteration (e.g. a SNP) in a template (e.g. an analyte), a first FRET labeled primer is designed to hybridize to a region encoding the deletion. A second primer comprises a sequence complementary to the region of the analyte about less than 500 bp away from the first primer. Upon amplification, a change in signal is observed. However, since a kink is present in the product template, an inefficient electron transport results in a decrease in the change of signal, e.g., when compared to the change in signal observed for an analyte without the genetic variation.

In some cases, the genetic variation detected is a different nucleotide occurrence in the analyte. In some cases, the different nucleotide occurrence is a single-nucleotide polymorphism (SNP). A SNP is a DNA sequence variation that occurs when a single nucleotide (e.g. A, T, C or G) in the genome is altered. In some cases, this alteration leads to either a presence of disease or is associated with (or a marker for) the presence of a disease or diseases. For example, a single nucleotide mutation from GAG to GTG in the β-globin gene that encodes haemoglobin results in development of sickle-cell anaemia.

In general, each individual has many SNPs that create a unique human DNA pattern. In some cases, a SNP is a common SNP or a rare SNP. In some cases, a SNP is a common SNP. In some cases, a common SNP has a minor allele frequency of about 1%, 2%, 3%, 4%, 5%, 6%, 7%, 8%, 9%, 10%, 11%, 12%, 13%, 14%, 15%, 16%, 17%, 18%, 19%, 20% or more. In some cases, a common SNP has a minor allele frequency of greater than 1%, 2%, 3%, 4%, 5%, 6%, 7%, 8%, 9%, 10%, 11%, 12%, 13%, 14%, 15%, 16%, 17%, 18%, 19% or 20%. In some cases, a common SNP has a minor allele frequency of less than 1%, 2%, 3%, 4%, 5%, 6%, 7%, 8%, 9%, 10%, 11%, 12%, 13%, 14%, 15%, 16%, 17%, 18%, 19% or 20%. In some cases, a SNP is a rare SNP. In some cases, a rare SNP has a minor allele frequency of about 1%, 2%, 3%, 4%, 5%, 6%, 7%, 8%, 9%, 10%, 11%, 12%, 13%, 14%, 15%, 16%, 17%, 18%, 19%, 20% or more. In some cases, a rare SNP has a minor allele frequency of greater than 1%, 2%, 3%, 4%, 5%, 6%, 7%, 8%, 9%, 10%, 11%, 12%, 13%, 14%, 15%, 16%, 17%, 18%, 19% or 20%. In some cases, a rare SNP has a minor allele frequency of less than 1%, 2%, 3%, 4%, 5%, 6%, 7%, 8%, 9%, 10%, 11%, 12%, 13%, 14%, 15%, 16%, 17%, 18%, 19% or 20%.

In some cases, provided herein is a method to detect the presence of a SNP in particular by a FRET labeled primer pairs in which the forward and reverse primers comprise a 1 base recognition region specific for the SNP and located at the 3' end, preferably within 3 bases from the 3' terminus, more preferably at the 3' terminus. In some cases, the method described herein is used to detect the presence of a common SNP. In some cases, the method described herein is used to detect the presence of a rare SNP. In some cases, the method described herein is used to detect the presence of a combination of common and rare SNPs.

In some cases, the method described herein is used to detect the presence of SNP in a sample. In some cases, the method described herein is used to detect multiple SNPs in a sample. In those embodiments a plurality of FRET-chromophore-labeled primer pairs can be used, each having the forward and reverse primers comprising a 1 base recognition region specific for the SNP and located at the 3' end, preferably within 3 bases from the 3' terminus, more preferably at the 3' terminus. In those embodiments the plurality of FRET labeled primers pair can attach a same or different FRET donor-acceptor chromophore pair and can be used at a same or different volumes and/or concentrations as will be understood by a skilled person upon reading of the present disclosure. In some cases, the method described herein is used to detect multiple common SNPs in a sample. In some cases, the method described herein is used to detect multiple rare SNPs in a sample. In some cases, the method described herein is used to detect a combination of common and rare SNPs in a sample. In some cases, the method described herein is used to detect a single SNP in a sample. In some cases, the method described herein is used to detect a single common SNP in a sample. In some cases, the method described herein is used to detect a single rare SNP in a sample.

In some cases, the presence of SNPs correlates directly with the development of a disease. In some cases, the presence of SNPs increases the chances of developing a disease. In some cases, the disease comprises a genetic disorder, an autoimmune disease, a neurological disease, a cardiovascular disease and cancer.

In some cases, provided herein is a method to detect the presence of a genetic variation involving more than 1 base pair by a FRET-chromophore-labeled primer pairs in which the forward and reverse primers comprise a up to 20 base recognition region specific for the variation and located at the 3' end, preferably including particular deletions, insertions of a single or multiple bases, substitution or any type of base modifications, possibly resulting in a shift of the reading frame. In some of these cases the genetic variation can be associated to cancers such as cancers associated with insertions in p53 gene.

C. Monitoring an Amplification Reaction

Disclosed herein is a method for detecting a change in signal generated by a set of chromophores for monitoring a reaction. In some cases, the method described herein can be used to monitor the progress of a PCR reaction. For example, at cycle 1, a set of fluorescence signals are measured, one measurement at the denaturing step and one measurement at the annealing step. During cycle 2, a second set of fluorescence signals are measured at the denaturing and annealing steps. A change in fluorescence between the signals taken at the two annealing step indicate an occurrence of a PCR reaction, while the signals taken during the denaturing steps are used as a control. In some cases, the change in signal from the two annealing steps is an increase in one signal. In some cases, the change is a decrease in another signal. In some cases, the change in signal is defined by a percentage. In some cases, the change in signal can be about 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900%, 1000% or more. In some cases, the change in signal can be greater than 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900% or 1000%. In some cases, the change in signal can be less than 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900% or 1000%. In some cases, the signals taken at the two annealing step remain constant. In some cases, the constant signal indicates the PCR reaction is functioning properly. In some cases, the signals taken at the two annealing steps indicate a change in signal. In some cases, this change in signal indicates the PCR reaction has failed. In some cases, the signals from the annealing steps serve as a control for each amplification cycle. In some cases, multiple reactions are monitored. In some cases, multiple reactions from a single sample are monitored. In some cases, multiple reactions from multiple samples are monitored. In some cases, a single reaction is monitored. In some cases, a single reaction from a single sample is monitored.

D. Detection of Morphological Change

Disclosed herein is a method for detecting or monitoring a morphological change in an analyte based on changes in signals. In some cases, an analyte is a protein, a polynucleotide, a lipid, a carbohydrate or an antibody. In some cases, an analyte is a polynucleotide. In some cases, the polynucleotide is a DNA or an RNA. In some cases, DNA and RNA can adopt different conformations such as a hairpin, tetraloop or pseudoknot. For example, to detect the different morphological state of a DNA containing a hairpin, a donor/acceptor pair can be conjugated to the respective stem of the hairpin. Since the FRET donor is in close proximity to the FRET acceptor, a signal can be observed. As the temperature increases, the DNA hairpin unwinds and a fluorescence signal may be decreased. In some cases, multiple signals are measured as the DNA unwinds. In some cases, only an initial and an end-point signals are measured as the DNA unwinds. In some cases, the multiple signals can generate a curve. In some cases, the multiple signals are used to generate a signature profile of a DNA containing a hairpin. In some cases, the signature profile is a curve. In some cases, an initial and an end-point signals are used to generate a signature profile. In some cases, the signature profile obtained from the DNA denaturation study is used as a control to detect the presence of a hairpin in a target DNA. In some cases, the method described herein is used to monitor the stability of a DNA or RNA conformation after introduction of addition, deletion, substitution or base modifications (e.g. unnatural bases) within the DNA or RNA. In some cases, the stability is affected by external factors. In some cases, the external factors include pH, organic or inorganic agents (e.g. salt, intercalating dye) or additional analytes. In some cases, the additional analyte is a DNA, RNA, protein or an antibody. In some cases, the method described herein is used to monitor the stability of a DNA or RNA conformation after introduction of the external factors.

In some cases, the method described herein is used to monitor a morphological change of a protein. For example, a protein residing in a native state can be a folded protein, a partially folded protein or a disordered protein. Folding or unfolding occurs due to the presence of binding partners, organic or inorganic agents, pH, and temperature. For a folded protein, an increase in temperature induces the protein to undergo an unfolding state. By labeling proteins with a plurality of donors and/or acceptors, a change in fluorescence signal can be measured with each iterative temperature increase and can be compared to the signals taken at its native state. In some cases, multiple signals are measured as the protein unfolds. In some cases, only an initial and an end-point signals are measured as the protein unfolds. In some cases, multiple signals can generate a curve. In some cases, multiple signals are used to generate a signature profile of the protein. In some cases, the signature profile is a curve. In some cases, an initial and an end-point signals are used to generate a signature profile. In some cases, the signature profile obtained from the protein unfolding study is used as a control to detect the morphology of proteins containing similar folds. In some cases, the method described herein is used to monitor the stability of a protein. In some cases, unfolding of the protein can be induced upon addition of an external factor. In some cases, the external factors include pH, organic or inorganic agents (e.g. salt, intercalating dye) or additional analytes. In some cases, the additional analyte is a DNA, RNA, protein or an antibody.

In some cases, the method described herein is used to monitor the morphology of an polynucleotide analyte-polynucleotide analyte interaction such as a protein-protein, protein-antibody or protein-polynucleotide (e.g. protein-DNA or protein-RNA) interactions. For example, during a protein-DNA interaction, a protein can adopt a different conformation upon binding of the DNA. In some cases, the change in signal associated with binding can be used to compare with the protein at its bound or unbound state. In some cases, multiple signals are measured as the protein-DNA complex forms. In some cases, only an initial and an end-point signals are measured as the complex forms. In some cases, the multiple signals can generate a curve. In some cases, the multiple signals are used to generate a signature profile of the protein. In some cases, the signature profile is a curve. In some cases, an initial and an end-point signals are used to generate a signature profile. In some cases, the signature profile obtained from the protein-DNA study is used as a control to detect the formation of protein complex with additional DNAs. In some cases, the methods described herein can monitor the stability of the protein complex with addition of another external factor. In some cases, the methods described herein can be used to monitor the morphological change of an analyte with multiple binding partners.

III. Multiplex Detection

Disclosed herein are examples of determining the presence of a plurality of analytes using a plurality of FRET donor/acceptor chromophores to detect polynucleotide analytes or other analytes associated thereto. For example, a multiplex detection method can combines the use of color, multiplicity of signal intensity, and/or mathematical strategies to circumvent degeneracy and ensure an infinite number of unique codes that can be unambiguously decoded in any combination of occurrences. For example, in detecting a sample containing four analytes, each analyte can be assigned a donor (blue, cyan, yellow and red florescent protein) and a green fluorescent protein as an acceptor attached to analyte-specific oligonucleotides (e.g., a forward PCR primer and a reverse PCR primer). Upon amplification, the presence or absence of an analyte is determined based on the presence or absence of a signal in that particular color.

In some cases, multiple color codes are generated using a plurality of chromophores. In some cases, multiple color codes are generated using a plurality of FRET donors and acceptors. In some cases, multiple color codes are generated using combinations of FRET donor/acceptor chromophore pairs. In some cases, multiple FRET chromophore pairs are assigned to multiple analytes. In some cases, a single FRET chromophore pair is assigned to multiple analytes. In some cases, a single FRET chromophore pair is assigned to one analyte.

In some cases, one color code or FRET chromophore pair is assigned to one analyte. In some cases, one color code or FRET chromophore pair is assigned to multiple analytes (e.g., to discriminate multiple analytes of varying lengths in a single detection reaction). In some cases, one color code or chromophore pair is assigned to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, 10,000 or 100,000 analytes. In some cases, multiple color codes or chromophore pairs are assigned to one or more analytes. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, or 1000 color codes or chromophore pairs are assigned to one or more analyte. In some cases, at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, 10,000 or 100,000 color codes or chromophore pairs are assigned to one analyte.

In some cases, one color is assigned as a control. In some cases, the control is a positive control or a negative control. In some cases, a particular signal multiplicity in a particular color is assigned as indicating a positive control. In some cases, multiple colors and/or signal multiplicities are assigned as positive controls.

A. Multiplex Detection for Genetic Variation

In some cases, the methods disclosed herein can be used to detect the presence of multiple genetic variations (e.g., SNPs). In some cases, an analyte contains a plurality of genetic variations. In some cases, an analyte contains one genetic variation. In some cases, one color is assigned to one genetic variation. In some cases, a sample contains a plurality of genetic variations, wherein a color code or FRET chromophore pair is assigned to each genetic variation. In some cases, a sample contains one genetic variation. In some cases, multiple genetic variations are tested for in the same sample, and each is assigned a different multiplicity of signal (FRET signal intensity) of a same FRET chromophore pair or a same color code, for purposes of unambiguous identification. In some cases, multiple genetic mutations are tested for in the same sample, and each is assigned with a different color-and-multiplicity combination, for the same purposes of unambiguous identification. In some cases, multiple genetic mutations are tested for in the same sample, and each is assigned with a same multiplicity and a same color code, for purposes of determining how many (if any) mutations on the panel are present in the sample without identifying them explicitly.

B. Multiplex Detection for SNP

In some cases, disclosed herein are methods of detecting of a SNP in an analyte. In some cases, an analyte contains a plurality of SNPs. In some cases, an analyte contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500 or more SNPs. In some cases, an analyte contains at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 SNPs. In some cases, an analyte contains no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 SNPs. In some cases, an analyte contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500 or more common SNPs. In some cases, an analyte contains at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 common SNPs. In some cases, an analyte contains no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 common SNPs. In some cases, an analyte contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500 or more rare SNPs. In some cases, an analyte contains at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 rare SNPs. In some cases, an analyte contains no more 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 rare SNPs.

In some cases, a sample contains a plurality of analytes. In some cases, multiple SNPs are detected from a plurality of analytes in the sample. In some cases, multiple common SNPs are detected from a plurality of analytes in the sample. In some cases, multiple rare SNPs are detected from a plurality of analytes in the sample. In some cases, multiple SNPs are detected from an analyte in the sample. In some cases, multiple common SNPs are detected from an analyte in the sample. In some cases, multiple rare SNPs are detected from an analyte in the sample. In some cases, one SNP is detected from an analyte in the sample. In some cases, one common SNP is detected from an analyte in the sample. In some cases, one rare SNP is detected from an analyte in the sample. In some cases, one SNP is detected in the sample. In some cases, one common SNP is detected in the sample. In some cases, one rare SNP is detected in the sample.

In some cases, a sample contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000 or more SNPs. In some cases, a sample contains at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000 or more SNPs. In some cases, a sample contains no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000 or more SNPs. In some cases, a sample contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000 or more common SNPs. In some cases, a sample contains at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000 or more common SNPs. In some cases, a sample contains no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000 or more common SNPs. In some cases, a sample contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000 or more rare SNPs. In some cases, a sample contains at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000 or more rare SNPs. In some cases, a sample contains no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000 or more rare SNPs.

In some cases, the method of detection utilizes an amplification method. In some cases, an amplification method comprises a polymerase chain reaction (PCR) method and an isothermal reaction method. In some cases, a PCR comprises a multiplex PCR, a real-time PCR, a quantitative PCR and a digital PCR (e.g. droplet digital PCR). In some cases, the method of detection utilizes a quantitative PCR method. In some cases, the quantitative PCR method is used in combination with a second method. In some cases, the second method is a digital PCR method. In some cases, the second method is a droplet digital PCR method.

In some cases, a signature profile is used to detect the presence of a SNP. In some cases, a signature profile is used to pinpoint the nucleotide mutation. In some cases, a signature profile is unique for each nucleotide mismatch, UU, UT, UG, UC, UA, AA, TT, GG, CC, AG, AC, TC, TC, and distinct from the wild-type. In some cases, a signature profile of a nucleotide mismatch is compared to that of a wild-type. In some cases, the signature profile of a SNP is compared to that of a wild-type. The signature profile of the wild-type can be generated separately in one or more experiments independent of the detection of the SNP. In some cases, a fluorescence signal of a SNP is compared to a fluorescence signal of a wild-type. In some cases, a change in fluorescence signal is detected between the signals of a SNP and a wild-type. In some cases, the change in signal can be calculated as a percentage. In some cases, the percentage of signal change is 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100%. In some cases, the percentage of signal change is about 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100%. In some cases, a change in signal is detected between the fluorescence signals of an AG mismatch and a wild-type. In some cases, the change in signal is calculated as a percentage. In some cases, the percentage of signal change is 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100%. In some cases, the percentage of signal change is about 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100%. In some cases, a change in signal is detected between the fluorescence signals of an AC mismatch and a wild-type. In some cases, the change in signal is calculated as a percentage. In some cases, the percentage of signal change is 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100%. In some cases, a change in signal is detected between the fluorescence signals of a TG mismatch and a wild-type. In some cases, the change in signal is calculated as a percentage. In some cases, the percentage of signal change is 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100%. In some cases, the percentage of signal change is about 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100%. In some cases, a change in signal is detected between the fluorescence signals of a TC mismatch and a wild-type. In some cases, the change in signal is calculated as a percentage. In some cases, the percentage of signal change is 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100%. In some cases, the percentage of signal change is about 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100%.

In some cases, a pair of primers is utilized to detect a SNP. In some cases, the first primer comprises a sequence encoding the SNP. In some cases, the first primer hybridizes to a region of the analyte encoding the SNP. In some cases, the second primer comprises a sequence not encoding the SNP. In some cases, the first and second primers both comprise a sequence encoding the SNP. In some cases, the second primer comprises a sequence complementary to a region of the analyte not encoding the SNP. In some cases, the first primer encodes a region on the analyte less than 500 base pairs apart from a region encoded by the second primer. In some cases, the first primer encodes a region on the analyte less than 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 195, 190, 185, 180, 175, 170, 165, 160, 155, 150, 145, 140, 135, 130, 125, 120, 115, 110, 105, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20 base pairs apart from a region encoded by the second primer. In some cases, the first primer encodes a region on the analyte no more than 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 195, 190, 185, 180, 175, 170, 165, 160, 155, 150, 145, 140, 135, 130, 125, 120, 115, 110, 105, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20 base pairs apart from a region encoded by the second primer. In some cases, the first primer encodes a region on the analyte about 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 195, 190, 185, 180, 175, 170, 165, 160, 155, 150, 145, 140, 135, 130, 125, 120, 115, 110, 105, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20 base pairs apart from a region encoded by the second primer.

In some cases, the first primer is a forward primer and the second primer is a reverse primer. In some cases, the forward primer hybridizes to a region of the analyte encoding the SNP. In some cases, the reverse primer comprises a sequence not encoding the SNP. In some cases, the reverse primer comprises a sequence complementary to a region of the analyte not encoding the SNP. In some preferred cases, both the forward primer and the reverse primer comprise a sequence encoding the SNP.

C. Supermulticolor Detection

Methods and systems and related compositions and kits herein described can also be used for simultaneous identification of multiple mutations in a sample such as a tissue sample. The identification can be performed in some cases, in a so-called FRETplexing method comprising allele-specific PCR assays using FRET-chromophore-labeled primers with supercolor multiplexing technology. The method produces fluorescence maps of the distribution of multiple mutations during PCR amplification. In several embodiments, the method provides results with specificity, sensitivity and robustness that are increased with respect to certain methods known in the art (e.g. certain methods using Taqman probes identifiable by a skilled person). In some cases, FRETplexing methods herein described allow identification of multiple genetic variations, such as multiple mutations and morphological information at reduced cost if compared to other approaches identifiable by a skilled person.

The term "supercolor multiplexing" as used herein refers to methods for multiplexed detection of a plurality of analytes in a sample described in U.S. Pat. No. 8,838,394. In the supercolor multiplexing method using one or more colors each color at different intensities of fluorescence input. Accordingly, multiple reaction are coded with one output of 1 unit per reaction in end-point measurement by calibration of starting chromophore amounts in a base-2 geometric progression, e.g. 1, 2, 4, 8, 16, 32, etc., which results in unambiguous decoding of the present analytes in any combination of occurrence. For example, for a two reaction detection with a same primer pair an output of 3 indicates that both reactions worked, as 1+2=3. In a same scenario an output of 1 indicates that the first reaction worked but not the second; an output 2 indicates that the second reaction worked but not the first. In some cases, the plurality of analytes can be detected in a single sample volume by acquiring a cumulative measurement or measurements of at least one quantifiable component of a signal.

In an exemplary embodiments in which detection of 3 SNPs is desired, in methods, and kits herein described a same FRET pair labeled with a FRET donor-acceptor chromophore pair (e.g. Cy3 on the forward primer and Cy5 on the reverse primer) can be used. As primers extend and hybridize, an end-point will be detected for the related FRET signals, which is cumulative of the FRET end-point signals for all reactions where successful binding occurred. Accordingly, a detection of an endpoint 4 will indicate that only the third SNP is present, a detection of a 5 endpoint will indicate that $1^{st}$ and $3^{rd}$ SNP are present as 5=1+4. Each signal can be used to construct a coding scheme which can then be used to obtain information concerning the presence or absence of each analyte of the plurality of analytes or to characterize features related to each of the plurality of analytes. In some cases, the each signal can be controlled by attaching fluorophores of different colors to one or more oligonucleotide primers or probes. In some cases, the each signal can be controlled by attaching fluorophores of a single color to one or more oligonucleotide primers or probes and varying intensities within that color for different oligonucleotide primers or probes. By utilizing combinations of different colors and intensities, any number of analytes can be coded. Detailed description with regard to encoding, analysis and decoding used in supercolor multiplexing methods can be referred to U.S. Pat. No. 8,838,394, which is incorporated by reference in its entirety.

In some cases, the intensities of the color for different oligonucleotide primers or probes can be controlled by varying the concentration of the primer pair. For example, for obtaining an intensity level at 1×, the concentration of a first primer pair can be selected at 2 uL of 10 uM according to Example 9; the concentration of a second primer pair can be selected at 4 uL of 10 uM (2×); the concentration of a third primer pair can be selected at 8 uL of 10 uM (4×), and so on according to the general concepts of the supercolor multiplexing methods described above. PCR experiments can be performed for a number of multiplexed assays containing one or more mutations with one or more corresponding primer pairs at the selected primer concentrations. For each multiplexed assay, a real-time PCR curve can be generated with the x-axis being the number of PCR cycles and the y-axis being the measured emission intensity of the multiplexed assay in A.U, such as the graph shown in FIG. 8 for single mutation 216T with the primer concentration at 1× (2 uL of 10 uM) according to Example 8. A Delta value from each of such PCR amplifications can be obtained by subtracting the maximum fluorescence signal recorded at the end of the PCR cycles and the minimum fluorescence signal recorded at the beginning of the PCR cycles. The delta values can then be used to chart the relatively output intensity changes that correspond to that specific mutation or mixture of various mutations. The plotted chart having an x-axis being the accumulated intensity level calculated from various combinations of the primer concentration and the y-axis being the measured emission intensity of the multiplexed assay in A.U. can then be used as a look-up table for determining the presence or absence of any particular mutation in a given sample containing a plurality of analytes and/or characterizing the sample to obtain additional information such as which mutation/mutations are present or absent in the sample.

IV. Characterization of Analytes

In some embodiments, methods of detection herein described can be used to characterize one or more analytes. In particular, in some cases characterization of at least one polynucleotide analyte can be performed using the FRET based methods and systems herein described and related kits and compositions.

The related method comprises selecting at least one polynucleotide region within the at least one polynucleotide analyte, the at least one polynucleotide region having at least one feature affecting biological or chemical characteristics of the at least one polynucleotide analyte. The method also comprises selecting at least one pair of primers attaching a FRET chromophore donor-acceptor primer pairs herein described, having a forward FRET-chromophore-labeled primer and a reverse FRET-chromophore-labeled primer specific for a first target polynucleotide and a second target polynucleotide within the at least one polynucleotide region.

The method further comprises performing at least one polynucleotide amplification reaction with the at least one pair primers to detect a variation and in particular a genetic variation in the region of interest. The method also comprises detecting a FRET signal from the sample generated the first FRET chromophore and the second FRET chromophore following the performing.

In some cases, each analyte of the at least one polynucleotide analyte is encoded by a color and intensity combination. Alternatively, each analyte of the at least one polynucleotide analyte is encoded by a single color with varying intensity. In some cases, the at least one pair of primers are labeled with an identical FRET donor-acceptor chromophore pair but with different intensity levels. The intensity levels can be varied by adjusting the relative concentrations and/or volumes of primers when comparing two constituent assays that form a multiplexed assay. Typically, the forward and reverse primer of each primer pair are at a same concentration and/or volume to ensure efficient hybridization and maximal FRET signal. For example, to code for analytes A and B using specific primers FA, RA, FB, RB, where F=forward, R=reverse, concentrations $C_{(FA)}=C_{(RA)}$ and $C_{(FB)}=C_{(RB)}$ are set up in a way so that $C_{(FA)}:C_{(FB)}=1:2$. Then if an accumulated concentration or FRET signal intensity level is 3×, both analytes A and B are present. If an accumulated concentration of FRET signal intensity level is 2×, only analyte B is present. If an accumulated concentration of FRET signal intensity level is 1×, only analyte A is present. For example, in FIG. 15 of Example 11, the relative FRET signal intensities obtained from qPCR experiments are plotted as a function of accumulated primer concentrations levels. The intensity level corresponding to the 1× primer concentration is 0.25 and the 2× primer concentration yields an intensity twice that of the 1× primer concentration, which is an intensity of 0.5. When the 1× and 2× primer concentrations are combined, a total FRET signal intensity of 0.75 is observed for the 3× concentration.

In some cases, quantitative information about the analytes can be extracted by comparing the threshold cycles of the resulting FRET signal real-time PCR curve with the threshold cycles of an included positive control, in analogy with traditional real-time qPCR. The signal multiplicity above described can be generally orthogonal information that is statistically independent of the information given by the threshold cycles. Thus in those cases both pieces of information can be extracted from the FRET signal signature profile for quantitative analysis purposes.

V. Analytes

An analyte may be any suitable polynucleotide analyte that can be analyzed using the methods and compositions of the present disclosure, where the analyte is capable of interacting with a reagent (e.g., an oligonucleotide such as a primer or probe attached to a chromophore) in order to generate a signal that can be measured. An analyte may be naturally-occurring or synthetic. An analyte may be present in a sample obtained using any methods known in the art. In some cases, a sample may be processed before analyzing it for an analyte. The methods and compositions presented in this disclosure may be used in solution phase assays, without the need for particles (such as beads) or a solid support.

In some cases, an analyte may be a polynucleotide, such as DNA, RNA, peptide nucleic acids, and any hybrid thereof, where the polynucleotide contains any combination of deoxyribo- and/or ribo-nucleotides. Polynucleotides may be single stranded or double stranded, or contain portions of both double stranded or single stranded sequence. Polynucleotides may contain any combination of nucleotides or bases, including, for example, uracil, adenine, thymine, cytosine, guanine, inosine, xanthine, hypoxanthine, isocytosine, isoguanine and any nucleotide derivative thereof. As used herein, the term "nucleotide" may include nucleotides and nucleosides, as well as nucleoside and nucleotide analogs, and modified nucleotides, including both synthetic and naturally occurring species. Polynucleotides may be any suitable polynucleotide for which one or more reagents as described herein may be produced, including but not limited to cDNA, mitochondrial DNA (mtDNA), messenger RNA (mRNA), ribosomal RNA (rRNA), transfer RNA (tRNA), nuclear RNA (nRNA), small interfering RNA (siRNA), small nuclear RNA (snRNA), small nucleolar RNA (snoRNA), small Cajal body-specific RNA (scaRNA), microRNA (miRNA), double stranded (dsRNA), ribozyme, riboswitch or viral RNA. Polynucleotides may be contained within any suitable vector, such as a plasmid, cosmid, fragment, chromosome, or genome.

Genomic DNA may be obtained from naturally occurring or genetically modified organisms or from artificially or synthetically created genomes. Analytes comprising genomic DNA may be obtained from any source and using any methods known in the art. For example, genomic DNA may be isolated with or without amplification. Amplification may include PCR amplification, multiple displacement amplification (MDA), rolling circle amplification and other amplification methods. Genomic DNA may also be obtained by cloning or recombinant methods, such as those involving plasmids and artificial chromosomes or other conventional methods (see Sambrook and Russell, *Molecular Cloning: A Laboratory Manual.*, cited supra.) Polynucleotides may be isolated using other methods known in the art, for example as disclosed in *Genome Analysis: A Laboratory Manual Series* (Vols. I-IV) or *Molecular Cloning: A Laboratory Manual*. If the isolated polynucleotide is an mRNA, it may be reverse transcribed into cDNA using conventional techniques, as described in Sambrook and Russell, *Molecular Cloning: A Laboratory Manual.*, cited supra.

In some embodiments, detection performed on one or more polynucleotide analytes can be indicative of features of another analyte associated therefore. Such other analyte may be a protein, polypeptide, lipid, carbohydrate, sugar, small molecule, or any other suitable molecule that can be detected through detection of polynucleotide analytes performed with the methods and compositions provided herein. An analyte may be an enzyme or other protein. An analyte may be a drug or metabolite (e.g. anti-cancer drug, chemotherapeutic drug, anti-viral drug, antibiotic drug, or biologic). An analyte may be any molecule, such as a co-factor, receptor, receptor ligand, hormone, cytokine, blood factor, antigen, steroid, or antibody.

An analyte may be any molecule from any pathogen, such as a virus, bacteria, parasite, fungus, or prion (e.g., PrP$^{Sc}$). Exemplary viruses include those from the families Adenoviridae, Flaviviridae, Hepadnaviridae, Herpesviridae, Orthomyxoviridae, Papovaviridae, Paramyxoviridae, Picornaviridae, Polyomavirus, Retroviridae, Rhabdoviridae, and Togaviridae. Specific examples of viruses include adenovirus, astrovirus, bocavirus, BK virus, coxsackievirus, cytomegalovirus, dengue virus, Ebola virus, enterovirus, Epstein-Barr virus, feline leukemia virus, hepatitis virus, hepatitis A virus, hepatitis B virus, hepatitis C virus, hepatitis D virus, hepatitis E virus, herpes simplex virus (HSV), HSV type 1, HSV type 2, human immunodeficiency virus (HIV), HIV type 1, HIV type 2, human papilloma virus (HPV), HPV type 1, HPV type 2, HPV type 3, HPV type 4, HPV type 6, HPV type 10, HPV type 11, HPV type 16, HPV type 18, HPV type 26, HPV type 27, HPV type 28, HPV type 29, HPV type 30, HPV type 31, HPV type 33, HPV type 34, HPV type 35, HPV type 39, HPV type 40, HPV type 41, HPV type 42, HPV type 43, HPV type 44, HPV type 45, HPV type 49, HPV type 51, HPV type 52, HPV type 54, HPV type 55, HPV type 56, HPV type 57, HPV type 58, HPV type 59, HPV type 68, HPV type 69, influenza type A virus, influenza type B virus, JC virus, Marburg virus, measles virus, metapneumovirus, mumps virus, Norwalk virus, parovirus, polio virus, rabies virus, respiratory syncytial virus including type A and type B, retrovirus, rhinovirus, rotavirus, Rubella virus, smallpox virus, vaccinia virus, West Nile virus, yellow fever virus, and human parainfluenza virus type 3.

Exemplary bacteria include those from the genuses *Bordetella, Borrelia, Brucella, Campylobacter, Chlamydia, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and *Yersinia*. Specific examples of bacteria include *Bordetella par apertussis, Bordetella pertussis, Borrelia burgdorferi, Brucella abortus, Brucella canis, Brucella melitensis, Brucella suis, Campylobacter jejuni, Chlamydia pneumoniae, Chlamydia psittaci, Chlamydia trachomatix, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella choleraesuis, Salmonella dublin, Salmonella enteritidis, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Yersinia pestis,* and *Yersinia enterocolitica.*

Exemplary parasites include those from the genuses *Acanthamoeba, Babesia, Balamuthia, Balantidium, Blasocystis, Cryptosporidium, Dientamoeba, Entamoeba, Giardia, Isospora, Leishmania, Naegleria, Pediculus, Plasmodium, Rhinosporidium, Sarcocystis, Schistosoma, Toxoplasma, Trichomonas,* and *Trypanosoma*. Specific examples of parasites include *Babesia divergens, Babesia bigemina, Babesia equi, Babesia microfti, Babesia duncani, Balamuthia mandrillaris, Balantidium coli, Dientamoeba fragilis, Entamoeba histolytica, Giardia lamblia, Isospora belli, Naegleria fowleri, Pediculus humanus, Plasmodium falciparum, Plasmodium knowlesi, Plasmodium malariae, Plasmodium ovale, Plasmodium vivax, Rhinosporidium seeberi, Sarcocystis bovihominis, Sarcocystis suihominis, Schistosoma mansoni, Toxoplasma gondii, Trichomonas vaginalis, Trypanosoma brucei,* and *Trypansoma cruzi.*

Exemplary fungi include those from the genuses *Apophysomyces, Aspergillus, Blastomyces, Candida, Cladosporium, Coddidioides, Cryptococcos, Exserohilum, Fusarium, Histoplasma, Pichia, Pneumocystis, Saccharomyces, Sporothrix, Stachybotrys,* and *Trichophyton*. Specific examples of fungi include *Aspergillus fumigatus, Aspergillus flavus, Aspergillus clavatus, Blastomyces dermatitidis, Candida albicans, Coccidioides immitis, Crytptococcus neoformans, Exserohilum rostratum, Fusarium verticillioides, Histoplasma capsulatum, Pneumocystis jirovecii, Sporothrix schenckii, Stachybotrys chartarum,* and *Trichophyton mentagrophytes.*

In some cases, an analyte may be any molecule derived from an archaea. Exemplary archaea include those from the genuses *Acidilobus, Acidococcus, Aeropyrum, Archaeoglobus, Caldisphaera, Caldococcus, Cenarchaeum, Desulfurococcus, Geogemma, Geoglubus, Haladaptatus, Halomicrobium, Hyperthermus, Ignicoccus, Ignisphaera, Methanobacterium, Natronococcus, Nitrosopumilus, Picrophilus, Pyrodictium, Pyrolobus, Staphylothermus, Stetteria, Sulfophobococcus, Thermodiscus, Thermosphaera* and *Thermoplasma*. Specific examples of archea include *A. aceticus, A. camini, A. fulgidus, A. infectus, A. lithotrophicus, A. pernix, A. profundus, A. veneficus, A. saccharovorans, A. sulfurreducens, C. dracosis, C. lagunensis, C. noboribetus, C. symbiosum, D. amylolyticus, D. fermentans, D. mobilis, D. mucosus, G. barossii, G. indica, G. pacifica, H. butylicus, N. maritimus, G. ahangari, H. paucihalophilus, H. mukohataei, H. katesii, H. zhouii, I. aggregans, I. islandicus, I. pacificus, I. hospitalis, M. aarhusense, M. alcaliphilum, M. beijingense, M. bryantii, M. congolense, M. curvum, M. espanolae, M. formicicum, M. ivanovii, M. oryzae, M. palustre, M. subterraneum, M. thermaggregans, M. uliginosum, N. amylolyticus, N. jeotgali, N. occultus, P. abyssi, P. brockii, P. occultum, P. fumarii, P. oshimae, P. torridus, S. hellenicus, S. marinus, S. hydrogenophila, S. zilligii, T. maritimus, T. aggregans, T. acidophilum,* T sp. P61, T sp. S01, T sp. S02, T sp. XT101, T sp. XT102, T sp. XT103, T sp. XT107 and *T. volcanium.*

In some cases, an analyte may be any molecule derived from a mammal. In some cases, the mammal is a human, a non-human primate, mouse, rat, rabbit, goat, dog, cat, or cow. In some embodiments, the mammal is a human. In some cases, a human is a patient.

In some cases, an analyte may be any molecule derived from a plant. In some cases, a plant is any of various photosynthetic, eukaryotic, multicellular organisms of the kingdom Plantae characteristically producing embryos, containing chloroplasts, having cellulose cell walls, and lacking the power of locomotion.

In some cases, the methods provided in this disclosure may be used to detect any one of the analytes described above, or elsewhere in the specification. In some cases the methods provided in this disclosure may be used to detect panels of the analytes described above, or elsewhere in the specification. For example, a panel may comprise an analyte selected from the group consisting of any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 500, 1000, 5000, 10000 or more analytes described above or elsewhere in the specification.

An analyte may be obtained from any suitable location, including from organisms, whole cells, cell preparations and cell-free compositions from any organism, tissue, cell, or environment. Analytes may be obtained from environmental samples, forensic samples, biopsies, aspirates, formalin fixed embedded tissues, air, agricultural samples, soil samples, petroleum samples, water samples, or dust samples. In some instances, an analyte may be obtained from bodily fluids which may include blood, urine, feces, serum, lymph, saliva, mucosal secretions, perspiration, central nervous system fluid, vaginal fluid, or semen. Analytes may also be obtained from manufactured products, such as cosmetics, foods, personal care products, and the like. Analytes may be the products of experimental manipulation including, recombinant cloning, polynucleotide amplification, polymerase chain reaction (PCR) amplification, isothermal amplification, purification methods (such as purification of genomic DNA or RNA), and synthesis reactions.

More than one type of analyte may be detected in each multiplexed assay. For example, a polynucleotide, a protein, a polypeptide, a lipid, a carbohydrate, a sugar, a small molecule, or any other suitable molecule may be detected simultaneously in the same multiplexed assay with the use of suitable reagents. Any combination of analytes may be detected at the same time.

Detection of an analyte may be useful for any suitable application, including research, clinical, diagnostic, prognostic, forensic, and monitoring applications. Exemplary applications include detection of hereditary diseases, identification of genetic fingerprints, diagnosis of infectious diseases, cloning of genes, paternity testing, criminal identification, phylogeny, anti-bioterrorism, environmental surveillance, and DNA computing. For example, an analyte may be indicative of a disease or condition. An analyte may be used to make a treatment decision, or to assess the state of a disease. The presence of an analyte may indicate an infection with a particular pathogen, or any other disease, such as cancer, autoimmune disease, cardiorespiratory disease, liver disease, digestive disease, and so on. The methods provided herein may thus be used to make a diagnosis and to make a clinical decision based on that diagnosis. For example, a result that indicates the presence of a bacterial polynucleotide in a sample taken from a subject may lead to the treatment of the subject with an antibiotic.

In some cases the methods and compositions of the present disclosure may be used to detect at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10,000, 100,000 or more analytes. In some cases the methods and compositions of the present disclosure may be used to detect about 1-10,000, 1-1000, 1-100, 1-50, 1-40, 1-30, 1-20, 1-10, or 1-5 analytes.

In some cases, this disclosure provides assays that are capable of unambiguously detecting the presence or absence of each of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10,000 or 100,000 analytes, in any combination of presence or absence, in a single sample volume. In some cases, this disclosure provides assays that are capable of unambiguously detecting the presence or absence of each of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10,000 or 100,000 analytes, in any combination of presence or absence, in a single sample volume. In some cases, this disclosure provides assays that are capable of unambiguously detecting the presence or absence of less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10,000 or 100,000 analytes, in any combination of presence or absence, in a single sample volume. In all of the above cases, in addition or in the alternative to detection of presence or absence of one or more analytes, quantitative detection of one or more analytes can also be performed as will be understood by a skilled person upon reading of the disclosure A. Distance/Length of Polynucleotide Analytes In one aspect, the methods provided herein may be used to detect polynucleotide analytes containing 1-500 base pairs (bp), referred to as the "length" of the analytes. In some cases, the methods provided herein may be used to detect polynucleotide analytes containing 10-450 bp, 15-400 bp, 20-350 bp, 25-300 bp, 30-250 bp, 35-200 bp, or 40-190 bp. In some cases, the methods may be used to detect a polynucleotide analyte containing 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190 or more base pairs. In some cases, the methods may be used to detect polynucleotide analyte containing at least 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 or 190 base pairs. In some cases, the methods may be used to detect polynucleotide analyte containing no more than 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 or 190 base pairs.

B. Sensitivity

In some cases, the methods disclosed herein may be used to detect polynucleotide analyte at concentrations of about 100 uM to about 1 fM. In some cases, the methods provided herein may be used to detect a polynucleotide analyte at concentrations of about 10 uM-20 fM, 1 uM-40 fM, 500 nM-60 fM, 100 nM-70 fM, 50 nM-80 fM, 30 nM-90 fM, 10 nM-100 fM. In some cases, the methods may be used to detect a polynucleotide analyte at a concentration of 10 nM, 9 nM, 8 nM, 7 nM, 6 nM, 5 nM, 4 nM, 3 nM, 2 nM, 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 180 pM, 160 pM, 140 pM, 120 pM, 100 pM, 95 pM, 90 pM, 85 pM, 80 pM, 75 pM, 70 pM, 65 pM, 60 pM, 55 pM, 50 pM, 45 pM, 40 pM, 35 pM, 30 pM, 25 pM, 20 pM, 18 pM, 16 pM, 14 pM, 12 pM, 10 pM, 8 pM, 6 pM, 4 pM, 2 pM, 1 pM, 900 fM, 800 fM, 700 fM, 600 fM, 500 fM, 400 fM, 300 fM, 200 fM, 100 fM, 50 fM, 10 fM, 1 fM, 100 aM, 10 aM, or 1 aM. In some cases, the methods may be used to detect a polynucleotide analyte at a concentration of at least 10 nM, 9 nM, 8 nM, 7 nM, 6 nM, 5 nM, 4 nM, 3 nM, 2 nM, 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 180 pM, 160 pM, 140 pM, 120 pM, 100 pM, 95 pM, 90 pM, 85 pM, 80 pM, 75 pM, 70 pM, 65 pM, 60 pM, 55 pM, 50 pM, 45 pM, 40 pM, 35 pM, 30 pM, 25 pM, 20 pM, 18 pM, 16 pM, 14 pM, 12 pM, 10 pM, 8 pM, 6 pM, 4 pM, 2 pM, 1 pM, 900 fM, 800 fM, 700 fM, 600 fM, 500 fM, 400 fM, 300 fM, 200 fM, 100 fM, 50 fM, 10 fM, 1 fM, 100 aM, 10 aM, or 1 aM. In some cases, the methods may be used to detect a polynucleotide analyte at a concentration of no more than 10 nM, 9 nM, 8 nM, 7 nM, 6 nM, 5 nM, 4 nM, 3 nM, 2 nM, 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 180 pM, 160 pM, 140 pM, 120 pM, 100 pM, 95 pM, 90 pM, 85 pM, 80 pM, 75 pM, 70 pM, 65 pM, 60 pM, 55 pM, 50 pM, 45 pM, 40 pM, 35 pM, 30 pM, 25 pM, 20 pM, 18 pM, 16 pM, 14 pM, 12 pM, 10 pM, 8 pM, 6 pM, 4 pM, 2 pM, 1 pM, 900 fM, 800 fM, 700 fM, 600 fM, 500 fM, 400 fM, 300 fM, 200 fM, 100 fM, 50 fM, 10 fM, 1 fM, 100 aM, 10 aM, or 1 aM.

C. Specificity

In some methods provided herein, a primer pair may be specific for one or a plurality of analytes. In some cases, a primer pair is specific to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 analytes. In some cases, a primer pair is specific to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 analytes. In some cases, a primer pair is specific to less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 analytes. In some cases, a primer pair is specific to one analyte. In some cases, a primer pair is universal to all analytes.

VI. Probes and Primers

Some of the methods provided in this disclosure utilize a reagent (e.g. an oligonucleotide such as a primer or a probe that is attached to a FRET chromophore) that can generate a signal in the presence of an analyte. Any suitable reagent may be used with the present disclosure. Generally, a reagent will have an analyte-specific component and a component that generates a signal in the presence of the analyte. In some cases, these reagents are referred to as probes and primers. In some cases, the probes are hybridization probes. In some cases, the hybridization probes are n oligonucleotide probes attached to FRET chromophores. In some cases, the probes are antibodies that detect an analyte, with a FRET chromophore label of a pair of FRET chromophore labels that emits signal upon binding of the antibody to an analyte presenting the other FRET chromophore of a same FRET pair. In some cases, the reagent is a primer. In some cases, the primer is attached to a chromophore. In some cases, the primer is attached to a donor chromophore. In some cases, the primer is attached to an acceptor chromophore.

In particular, in various embodiments at least one pair of FRET-chromophore-labeled reagents (e.g. primers), is designed so that each pair of the at least one pair has a first FRET-chromophore-labeled reagent (e.g. a forward FRET-chromophore-labeled primer) attaching a first FRET chromophore of a FRET donor-acceptor chromophore pair, and a second FRET-chromophore-labeled reagent (e.g. a reverse FRET-chromophore-labeled primer) attaching a second FRET chromophore of the FRET donor-acceptor chromophore pair, the second FRET chromophore being different from the first FRET chromophore. In the embodiments herein described the first FRET chromophore and the second FRET chromophore are selected in the pair in view of their capability of providing an energy transfer from one to another when located at a Förster distance one with respect to the another.

In the embodiments herein described, the first FRET-chromophore-labeled primer and second FRET-chromophore-labeled primer are specific for a first and second target polynucleotide respectively within the at least one polynucleotide analyte, wherein the first target polynucleotide and the second target polynucleotide are located within the at least one polynucleotide analyte so that upon specific binding with the first FRET-chromophore-labeled reagent and the second FRET-chromophore-labeled reagent, the first FRET chromophore and the second FRET chromophore are located within a distance up to four times the Förster distance one with respect to the other. In embodiments, where the first FRET-chromophore-labeled primer and the second FRET-chromophore-labeled primer are a FRET-chromophore-labeled forward and reverse primer, a forward FRET-chromophore-labeled primer has a sequence specific for a first target polynucleotide within the at least one polynucleotide analyte and the reverse FRET-chromophore-labeled primer has a sequence specific for a second target polynucleotide.

The methods of the present disclosure may use one or more reagents (e.g., an oligonucleotide such as a primer or a probe that is attached to a chromophore) to detect each analyte. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more reagents may be used to detect of each analyte. In some cases, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 reagents may be used to detect of each analyte. In some cases, fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 reagents may be used to detect of each analyte.

In some cases, a sample is contacted with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more reagents to detect of all analytes. In some cases, a sample is contacted with at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more reagents to detect of all analytes. In some cases, a sample is contacted with fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 reagents to detect all analytes.

In all of the above cases, in addition or in the alternative to detection of presence or absence of one or more analytes, quantitative detection of one or more analytes can also be performed as will be understood by a skilled person upon reading of the disclosure.

In particular primers or other oligonucleotides are designed to specifically bind to respective target sequences on at least one polynucleotide analyte or region thereof to be targeted. The target sequences for each pair of primers or primer/oligonucleotide attaching a FRET donor-acceptor chromophore pair are selected on the at least one polynucleotide or region therefore to be targeted so that upon specific binding of the primer pair or primer/probe pair with the corresponding target sequence, the primer pair or primer/probe pair present the FRET donor-acceptor chromophore at a distance up to four times their Förster distance one with respect to the other.

General concepts for PCR primer design are well-known for a person skilled in the art. In obtaining a balance between specificity and efficiency of amplification, parameters that need to be considered for designing primers include primer length, reasonable GC content and melting temperature ($T_m$) that provide a sufficient thermal condition for efficient annealing, the PCR product length, placement of the primers within the target sequence, and many other factors identifiable to a skilled person in the art. In particular, complementarity between primers should be avoided as undesirable formation of primer-dimer may be formed as a result of the amplification of the complementary primers themselves. The selection of PCR primer sets can be performed manually or using analytic computer software widely available to a skilled person.

The FRET-chromophore-labeled primers are designed and labeled in such a way that resulting amplicons can produce FRET signal after annealing step. In cases when SNPs are the target of interest, primes typically have their 3' end opposite to the targeted point mutation for maximal specificity. In particular As described above, primers attached to a FRET donor or a FRET acceptor chromophore may be used to detect at least an analyte in a polynucleotide amplification assay. The receptor can emit a fluorescence signal generated upon excitation by the energy released from the donor when the donor and acceptor are in close proximity. The sequence of the primer can be designed to be complementary to a polynucleotide sequence present in an analyte, and the primer is capable of hybridizing to the analyte. The sequence of the primer can also be designed to contain one or more nucleotide variations in a polynucleotide sequence of an analyte, and the primer is capable of hybridizing to the analyte. A donor chromophore can be attached to the 5' end of one of a primer pair. An acceptor chromophore can be attached to the 5' end of the second primer of the primer pair. In some cases, one of the primer pair is specific to the target sequence of the analyte containing one or more nucleotide variations and the other primer is specific to the wild-type of the analyte. In some cases, both primers are specific to the target sequence of the analyte containing one or more nucleotide variations. In some cases, the 3'-end basepairs of both primers are specifically designed to match the SNP sequence in the cases for SNP detection and characterization. Hybridization of the primers may be performed in a nucleic acid amplification reaction comprising donor/acceptor attached primers (e.g., a polymerase chain reaction). Upon extension of the primers by a DNA polymerase, the donor and acceptor are incorporated in the amplicon or amplification product (e.g., an analyte). The incorporation of the donor and the acceptor in the newly generated amplicon can lead to signal generation (e.g., an increase of fluorescence emission intensity from the receptor or a decrease of fluorescence emission intensity from the donor). With each iterative amplification reaction, the fluorescence intensity is changed by a factor having a value in a range between 1 and 2, with a maximum value of 2. The amount of fluorescence emission intensity detected can be used to directly determine the amount of analyte present. If no analyte is present, little or no emission will be observed.

The size of the generated amplicons can depend on the specific application. In some cases, the generated amplicons that lead to emission of fluorescence can have a length anywhere between 30-1000 bp. In some cases, the generated amplicons are preferably within the range of 30-250 bp. In some cases, the generated amplicons are preferably within the range of 40-60 bp for generating a preferred signal intensity as FRET signal decrease over distance. In some embodiments, the generated amplicons are about 40 bp long.

In some cases, a sample to be analyzed is contacted with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more pairs of primers (e.g. a forward primer and a reverse primer). In some cases a sample to be analyzed is contacted with at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more pairs of primers. In some cases a sample to be analyzed is contacted with fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 pairs of primers. In some cases, the number of pairs of primers is 2-10, 3-15, 4-20, 3-10, 4-10, 5-10, 6-8, or 6-10. In some cases, a sample to be analyzed is contacted with 1 pair of primers.

In some cases, a sample may contain one or more analytes. In some cases, one primer pair may be used to detect each analyte. In some cases, a sample is contacted with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, 10000 or more different pairs of primers with each primer pair detecting a single analyte. In some cases, a sample is contacted with at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, 10000 or more different pairs of primers with each primer pair detecting a single analyte. In some cases, a sample is contacted with fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, 10000 or more different pairs of primers with each primer pair detecting a single analyte. In some cases, the number of pairs of primers is 2-10, 3-15, 4-20, 3-10, 4-10, 5-10, 6-8, or 6-10. In all of the above cases, in addition or in the alternative to detection of presence or absence of one or more analytes, quantitative detection of one or more analytes can also be performed as will be understood by a skilled person upon reading of the disclosure.

In some cases, primers may be specific for a particular analyte and capable of amplifying a region complementary to a probe. In some cases, the number of primers used is equivalent to the number of probes. In other cases, the number of probes used may exceed the number of primer used. In some cases, the number of primers and probes is defined by a ratio. In some cases, the ratio of primer to probe is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000. In some cases, the ratio of probe to primer is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000.

The term "FRET-chromophore-labeled primer" refers to a primer attached with either a FRET donor chromophore or a FRET acceptor chromophore. A primer attached with a FRET donor chromophore is referred to as a FRET-donor-labeled primer and a primer attached with a FRET acceptor chromophore is referred to as a FRET-acceptor-labeled primer.

The FRET chromophore labels of the present disclosure can be attached to a primer at any location except for the 3' end. In some cases, a single chromophore is attached to the primer at the 5' end. In some cases, multiple chromophores are labeled to the primer with at least one chromophore labeled at the 5' end. When a donor chromophore is attached to the 5' end of one primer and an acceptor chromophore is attached to the 5' end of the other primer, the distance from the 5' end of one primer to the 5' end of the other primer along the template sequence should be short enough to allow efficient FRET between the donor and acceptor chromophores. In some cases, chromophores are not directly attached to the primers. Instead, the chromophores are attached to aptamers or other synthetic recognition molecules that are subsequently attached to the primers. Methods of chromophore labeling are well defined in the art. See, e.g. Pesce et al, editors, Fluorescence Spectroscopy, Marcel Dekker, New York, (1971); White et al. Fluorescence Analysis: A Practical Approach, Marcel Dekker, New York, (1970); and the like. Further, there is extensive guidance in the literature for derivatizing donor and acceptor chromophore molecules for covalent attachment via common reactive groups that can be added to an oligonucleotide. See, e.g. U.S. Pat. Nos. 3,996,345; and 4,351,760. In examples that utilize chromophore labels as described herein, any suitable labeling techniques identifiable by a skilled person may be used.

Attachment of donors and acceptors to a primer may be performed in the same reaction or in serial reactions. A series of reactions may be performed to label probes with at least one donor or acceptor chromophore and the reaction products may be mixed to generate a mixture of probes with different donor or acceptor chromophores.

In some cases, a single primer pair may be used for each analyte. In order to utilize supercolor multiplexing, each primer pair may be labeled with a same donor and acceptor chromophore pair but at varied pre-determined concentration ratios for different primer pairs. The concentration ratios ensure that the respective FRET signals will produce intensities of respective predetermined ratios as well. Then the measured intensity can be decoded to give information about the present analyte(s), if any. A positive control can be set up in the same way to produce a predetermined intensity, e.g. 1×. Then the control becomes part of the same measurement and coding scheme.

Although many aspects of the present disclosure are exemplified using nucleic acid-based probes and primers, one of ordinary skill in the art will readily recognize that other forms of probes and primers would work equally well with the examples described in this disclosure. For example, a binding molecule specific to an analyte could be used as a probe. Non-limiting exemplary binding molecules include an antibody recognizing an analyte, and generating a signal in the presence of an analyte.

VII. Chromophores

Chromophores are molecules capable of selective light absorption resulting in the coloration of these molecule containing compounds. The color arises when a molecule at an excited state releases energy in the form of light with a defined spectrum. When two chromophores are selected such that the emission spectrum of one (e.g. donor) overlaps the excitation spectrum of the other (e.g. acceptor), the two chromophores can form a FRET pair. A FRET pair of chromophores when positioned at a Förster distance of each other can produce FRET signal with 50% energy transfer efficiency when the donor is excited optically. Exemplary FRET-based chromophores include, but are not limited to, a fluorochrome, a non-fluorochrome chromophore, an absorption chromophore, a fluorophore, any organic or inorganic dye, metal chelate, or any fluorescent enzyme substrate. In some cases, the chromophore is a fluorochrome. In some cases, the fluorochrome is a fluorophore.

Several chromophores are described in the art, e.g. Berlman, Handbook of Fluorescence Spectra of Aromatic Molecules, 2nd Edition, Academic Press, New York, (1971). In examples that utilize fluorescent labels as described herein, any suitable fluorescent label may be used.

Exemplary FRET donors suitable for use with the present disclosure includes rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, and thiorhodamine; cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyrene derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, and bilirubin; 1-dimethylaminonaphthyl-5-sulfonate, 1-anilino-8-naphthalene sulfonate, 2-p-touidinyl-6-naphthalene sulfonate, 3-phenyl-7-isocyanatocoumarin, N-(p-(2-benzoxazolyl)phenyl)maleimide, stilbenes, pyrenes, and the like.

Exemplary FRET acceptors suitable for use with the present disclosure include Cy5, HEX, ROX, TMR, YFP, and RFP.

The donor/acceptor chromophores that may be used with the disclosure are not limited to any of the donor/acceptor chromophores described herein. For example, donor/acceptor chromophores with improved properties are continually developed, and these donor/acceptor chromophores could readily be used with the methods provided in this disclosure. Such improved donor/acceptor chromophores include quantum dots, which may emit energy at different wavelengths after being excited at a single wavelength.

A. Chromophore Combinations

In some cases, a plurality of chromophores is labeled on a probe. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more chromophores are labeled on a probe. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more chromophores are labeled on a probe. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 chromophores are labeled on a probe. In some cases, one chromophore is labeled on a probe.

In some cases, the probe comprises a primer. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more chromospheres is labeled on a primer. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more chromospheres is labeled on a primer. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 chromospheres is labeled on a primer. In some cases, one chromophore is labeled on a primer. In some cases, one chromophore is labeled at the 5' end of a primer. In some cases, a plurality of chromophores is labeled on a primer with at least one chromophore labeled at its 5' end.

In some cases, a plurality of FRET donor chromophores and FRET acceptor chromophores are labeled on a probe. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more donors are labeled on a probe. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more donors are labeled on a probe. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 donors are labeled on a probe. In some cases, one donor is labeled on a probe. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more acceptors are labeled on a probe. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more acceptors is labeled on a probe. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 acceptors are labeled on a probe. In some cases, one acceptor is labeled on a probe.

In some cases, a combination of FRET donor and acceptor chromophores are labeled on a probe. In some cases, the number of donors and acceptors on a probe is defined by a ratio. In some cases, the ratio of donor to acceptor is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000. In some cases, the ratio of donor to acceptor is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000. In some cases, the ratio of acceptor to donor is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000. In some cases, the ratio of acceptor to donor is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000.

In some cases, a plurality of donors and acceptors is labeled on a primer. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more donors are labeled on a primer. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more donors are labeled on a primer. In some cases, a primer is labeled with one donor is labeled on a primer. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 donors are labeled on a primer. In some cases, one donor is labeled at the 5' end of a primer. In some cases, a plurality of donors re labeled on a primer with at least one donor labeled at its 5' end. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more acceptors are labeled on a primer. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more acceptors are labeled on a primer. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 acceptors are labeled on a primer. In some cases, one acceptor is labeled on a primer. In some cases, one acceptor is labeled at the 5' end of a primer. In some cases, a plurality of acceptors is labeled on a primer with at least one acceptor labeled at its 5' end.

In some cases, a combination of donors and acceptors are labeled on a primer. In some cases, the number of donors and acceptors on a primer is defined by a ratio. In some cases, the ratio of donor to acceptor is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000. In some cases, the ratio of acceptor to donor is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000.

In some cases, multiple donors are paired with one acceptor. In some cases 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more donors are paired with one acceptor. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more donors are paired with one acceptor. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 donors are paired with one acceptor. In some cases, multiple donor and acceptor pairs are used. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more donor and acceptor pairs are used. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more donor and acceptor pairs are used. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more donor and acceptor pairs are used. In some cases, 1 donor and acceptor pair is used.

In some cases, a pair of primers comprises a first primer and a second primer. In some cases, multiple donors are labeled on a first primer and one acceptor is labeled on a second primer. In some cases, at least one donor is labeled on the 5' end of the first primer. In some cases, the acceptor is labeled on the 5' end of the second primer. In some cases, multiple donors are labeled on a second primer and one acceptor is labeled on a first primer. In some cases, at least one donor is labeled on the 5' end of the second primer. In some cases, the acceptor is labeled on the 5' end of the first primer.

In some cases, the first primer is a forward primer and the second primer is a reverse primer. The term "FRET-labeled forward primer" is referred to as a forward primer attached with one chromophore of an at least one FRET donor-acceptor chromophore pair. The term "FRET-labeled reverse primer" is referred to as a reverse primer attached with the other chromophore of the at least one FRET donor-acceptor chromophore pair.

In some cases, multiple donors are labeled on the forward primer and one acceptor is labeled on the reverse primer. In some cases, at least one donor is labeled on the 5' end of the forward primer. In some cases, the acceptor is labeled on the 5' end of the reverse primer. In some cases, multiple donors are labeled on a reverse primer and one acceptor is labeled on a forward primer. In some cases, at least one donor is labeled on the 5' end of the reverse primer. In some cases, the acceptor is labeled on the 5' end of the forward primer.

The skilled artisan will realize that the advantages of the present disclosed probes or primers may be retained while modifying various aspects of its structure. For example, but not by way of limitation, the number of donor/acceptor pairs may be modified. The addition of more donor/acceptor pairs to the probe or primer is expected to increase the amount of total fluorescence observable prior to initiation of amplification reaction. There is no upper limit to the number of donor/acceptor pairs that may be added to the probe or primer. In one example, the number of donor/acceptor pairs is at least two. In other examples, the detector contains at least three or more donor/acceptor pairs. In some examples, the detector may contain at least 10, 20, 30, or 50 pairs, or it may contain hundreds of donor/acceptor pairs, as needed to produce, for example, an optimal signal-to-noise ratio and assay sensitivity.

In some cases, the methods provided in this disclosure may include the use of donor/acceptor pair as a control. The control donor/acceptor pair may be attached to one or more detector pairs binding a positive control analyte, and each analyte to be detected, in a sample. If the same sequence occurs in the positive control analyte and each analyte to be detected, a single control primer pair may be used. If the same sequence does not occur in the positive control analyte and each analyte to be detected, different primer pairs may be used, but each primer pair may still be attached to the control donor/acceptor pair.

For example, building on the methods described above, one donor/acceptor pair may be used to encode the presence of a control analyte that is always present in the sample. The control analyte may be added to the sample, or may be inherently present in the sample. Additional donor/acceptor pairs may be used to encode the presence of additional analytes.

B. Signals

Disclosed herein is a method of utilizing the signal intensity to detect an analyte. In some cases, the signal is an increase in intensity. In some cases, the signal is a decay in intensity. In some cases, a signature profile is generated based on the changes in intensity at a specific distance. In some cases, once the length of an analyte is known, additional information can be extrapolated. In some cases, additional information includes the molecular weight of an analyte.

In some cases, the methods presented in this disclosure may be used with any quantifiable signal. As described herein and else wherein, a coding scheme may be utilized to indicate a multiplicity of signal intensity without consideration of color. In some cases, the coding scheme is equally applicable to any other method providing a quantifiable signal, including an electrochemical signal and a chemiluminescent signal.

The methods presented in this disclosure may also utilize the measurement of a signal in at least two dimensions, also referred to as the measurement of at least two components of a signal. In some cases, the utilization of at least two components of a signal (e.g., color and intensity) allows the generation of more unique codes per unit of signal intensity bandwidth.

In some cases, a quantifiable signal comprises a waveform that has both a frequency (wavelength) and amplitude (intensity). A signal may be an electromagnetic signal. An electromagnetic signal may be a sound, a radio signal, a microwave signal, an infrared signal, a visible light signal, an ultraviolet light signal, an x-ray signal, or a gamma-ray signal. In some cases, an electromagnetic signal may be a fluorescent signal, for example a fluorescence emission spectrum that may be characterized in terms of wavelength and intensity.

In certain portions of this disclosure, the signal is described and exemplified in terms of a fluorescent signal. This is not meant to be limiting, and one of ordinary skill in the art will readily recognize that the principles applicable to the measurement of a fluorescent signal are also applicable to other signals. For example, like fluorescent signals, any of the electromagnetic signals may also be characterized in terms of a wavelength and intensity. The wavelength of a fluorescent signal may also be described in terms of color. The color may be determined based on measuring intensity at a particular wavelength or range of wavelengths, for example by determining a distribution of fluorescent intensity at different wavelengths and/or by utilizing a band pass filter to determine the fluorescence intensity within a particular range of wavelengths. Such band pass filters are commonly employed in a variety of laboratory instrumentation, including quantitative PCR machines. Intensity may be measured with a photodetector. A range of wavelengths may be referred to as a "channel."

In cases when fluorophores are used as FRET-based chromophore, the FRET signal can be in a range between 480 and 700 nm. The FRET signal intensity generated by FRET fluorophores can vary largely from a single photon to any level of intensity.

In some cases, more than two components of a signal may be measured. For example, 3, 4, 5, 6, 7, 8, 9, 10, 11, 12, 13, 14, 15, 16, 17, 18, 18, 20 or more components of a signal may be measured. At least 2, 3, 4, 5, 6, 7, 8, 9, 10, 11, 12, 13, 14, 15, 16, 17, 18, 18, or 20 components of a signal may be measured. At least 2, but fewer than 3, 4, 5, 6, 7, 8, 9, 10, 11, 12, 13, 14, 15, 16, 17, 18, 18, or 20 components of a signal may be measured. In some cases, 2-3, 2-4, 2-5, 2-6, 3-5, 3-6, 3-8, or 5-10 components of a signal may be measured. These additional components may include kinetic components, such as a rate of signal decay and rate of photobleaching.

Signals can be measured and compared at various points during a detection method described herein. For example, during an amplification reaction (e.g., a PCR reaction), pairwise signals can be measured. In some cases, a signal can be measured: before annealing and after annealing of the primers to the template (e.g., analyte); before and after denaturing the double stranded template; and before the annealing step and after the denaturing step. Generally, a fluorescence signal in one or multiple segments of the spectrum can be detected and correlated with the current temperature of the sample and phase of the reaction, to generate a signature. A signal signature as described herein can be generated using these measurements.

C. Signature Profiles

A signature profile typically comprises a plurality of signals. In some cases, a signal includes an electrochemical signal, a chemiluminescence signal and a fluorescence signal. In some cases, a signature profile contains a plurality of fluorescence signals. In some cases, a profile curve is generated from the plurality of florescence signals. In some cases, a signature profile contains an initial fluorescence signal and an end-point fluorescence signal. In some cases, a fluorescence signal is influenced by external factors. In some cases, the external factors include temperature, pH, organic and inorganic agents (e.g. salts, urea, DMSO) and addition or removal of chromophores.

In some cases, signature profiles are generated from different types of detection experiments. In some cases, a signature profile generated from a polynucleotide morphology study is referred to as a morphology curve. In some cases, a signature profile generated from a denaturation study is referred to as a melt curve. In some cases, a signature profile generated from a persistence length study is referred to as a length curve. In some cases, a signature profile generated from a single-nucleotide polymorphism (SNP) study is referred to as a SNP curve.

In some cases, the change in signal can be calculated as a percentage. In some cases, the percentage of signal change is 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 150, 200, 300, 400, 500, 600, 700, 800, 900, 1000, 10,000%. In some cases, the percentage of signal change is about 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 150, 200, 300, 400, 500, 600, 700, 800, 900, 1000, 10,000%.

VIII. Analytical Techniques and Instrumentation

The methods described in this disclosure are compatible with a variety of amplification methods, including polymerase chain reaction (PCR), ligase chain reaction (LCR), replicase-mediated amplification, strand-displacement amplification (SDA), "rolling circle" types of amplification, and various transcription associated amplification methods. See, e.g., PCR amplification: U.S. Pat. Nos. 4,683,195, 4,683,202, and 4,800,159; LCR amplification: U.S. Pat. No. 5,516,663 and EP 0320308 B1; replicase-mediated amplification: U.S. Pat. No. 4,786,600; SDA amplification: U.S. Pat. Nos. 5,422,252 and 5,547,861; rolling circle types of amplification: U.S. Pat. Nos. 5,714,320 and 5,834,252; and transcription associated amplification: U.S. Pat. Nos. 5,399,491, 5,554,516, 5,130,238, 5,437,990, 4,868,105 and 5,124,246, PCT Pub. WO 1988/010315 A1 and US Pub. 2006-0046265 A1, which are hereby incorporated by reference.

In some cases, the polymerase chain reaction (PCR) is a multiplex-PCR, a variable number of tandem repeats (VNTR) PCR, an asymmetric PCR, long PCR, a nested PCR, a hot-start PCR, a Touchdown PCR, an assembly PCR, a colony PCR, a quantitative PCR (qPCR), an end point PCR, a reverse transcriptase PCR, a digital PCR or a droplet digital PCR. In some cases, the PCR is a quantitative PCR.

In some cases, the PCR amplification step of the present disclosure can be performed by standard techniques well known in the art (See, e.g., Sambrook, E. F. Fritsch, and T. Maniatis, Molecular Cloning: A Laboratory Manual, Second. Edition, Cold Spring Harbor Laboratory Press (1989); U.S. Pat. No. 4,683,202; and PCR Protocols: A Guide to Methods and Applications, Innis et al., eds., Academic Press, Inc., San Diego (1990) which are hereby incorporated by reference), PCR cycling conditions typically consist of an initial denaturation step, which can be performed by heating the PCR reaction mixture to a temperature ranging from about 80° C. to about 105° C. for times ranging from about 1 to about 10 min. Heat denaturation is typically followed by a number of cycles, ranging from about 1 to about 50 cycles, each cycle usually comprising an initial denaturation step, followed by a primer annealing step and concluding with a primer extension step. Enzymatic extension of the primers by a nucleic acid polymerase, e.g. TAQ polymerase, produces copies of the template (e.g., an analyte) that can be used as templates in subsequent cycles. In some cases, the number of cycles ranges from about 1, 2, 3, 4, 5, 6, 7, 8, 9, 10, 15, 20, 25, 30, 35, 40, 45, 50, 55, 60, 65, 70, 75 to about 80 cycles.

The methods provided herein are suitable for use with a variety of detection methods. For example, the methods may be applied using an analytical technique that measures the wavelength and intensity of a fluorescent signal. This may be accomplished by measuring the intensity of a signal across a spectrum of wavelengths, or by using band pass filters that restrict the passage of certain wavelengths of light, thereby allowing only light of certain wavelengths to reach a photodetector. Many real-time PCR and quantitative PCR instruments comprise an excitation light source and band pass filters that enable the detection of fluorescent signals. Therefore, the methods of the present disclosure can be readily applied using instruments widely used in the art. No separation is necessary. The present disclosure does not require the use of beads or a solid phase. Of course, one of ordinary skill in the art would understand that the present disclosure could be used with separation, beads, or a solid phase, if desired.

IX. Diseases

The methods described herein can be used, for example, to detect one or more analytes associated with a disease or one or more genetic variations (e.g., a SNP) associated with a disease. A disease is an abnormal condition of an organism. In some cases, the organism is a mammal, such as a human, non-human primate, mouse, rat, rabbit, goat, dog, cat, or cow. In some cases, the mammal is a human. In some cases, the human is a patient or subject. In some cases, the disease is a genetic disorder, an autoimmune disease, a neurological disease, a cardiovascular disease or a cancer.

A genetic disorder is a disease caused by one or more abnormalities in the genome. Exemplary genetic disorders include 22q11.2 deletion syndrome, Acrocephaly, Acute cerebral Gaucher's disease, Adrenal gland disorders, Adrenogenital syndrome, Alzheimer's disease, Amelogenesis imperfect, androgen insensitivity syndrome, anemia, Angelman syndrome, Apert syndrome, ataxia telangiectasia, Canavan disease, Charcot-Marie-Tooth disease, Color blindness, Cri du chat, Cystic fibrosis, Down syndrome, Duchenne muscular dystrophy, Haemochromatosis, Haemophilia, Klinefelter syndrome, Neurofibromatosis, Phenylketonuria, Polycystic kidney disease, Prader-Willi syndrome, Sickle-cell disease, Tay-Sachs disease and Turner syndrome.

An autoimmune disease is a disease caused when the immune system mistakenly attacks and destroys healthy body tissue. Exemplary autoimmune diseases include lopecia areata, autoimmune hemolytic anemia, autoimmune hepatitis, dermatomyositis, diabetes (type 1), several forms of juvenile idiopathic arthritis, glomerulonephritis, Graves' disease, Guillain-Barré syndrome, idiopathic thrombocytopenic purpura, myasthenia gravis, several forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, several forms of thyroiditis, several forms of uveitis, vitiligo, and granulomatosis with polyangiitis (Wegener's).

Exemplary neurological diseases include attention deficit hyperactivity disorder (ADHD), ALS, Alzheimer's disease, bipolar disorder, Bell's palsy, birth defects of the brain and spinal cord, cerebral palsy, chronic fatigue syndrome, dyslexia, epilepsy, Guillain-Barré syndrome, multiple sclerosis, muscular dystrophy, neuropathy, neuromuscular and related diseases, Parkinson's disease, schizophrenia, scoliosis and spinal deformity.

Exemplary cardiovascular disease include acute myocardial infarction, angina, arrhythmia, atherosclerosis, cardiomegaly, cardiomyopathy, carotid artery disease, congenital heart disease, congestive heart failure, coronary artery disease, endocarditis, fluid around the heart, hypertension, infective endocarditis, mitral valve prolapsed, peripheral artery disease, stroke, and valvular heart disease.

Cancer is characterized by an abnormal growth of cells. Exemplary cancer include bladder, brain, breast, bladder, bone, cervical, colon, esophageal, kidney, liver, lung, ovarian, pancreatic, proximal or distal bile duct, prostate, skin, stomach, thyroid, and uterine cancer.

Figure 5:
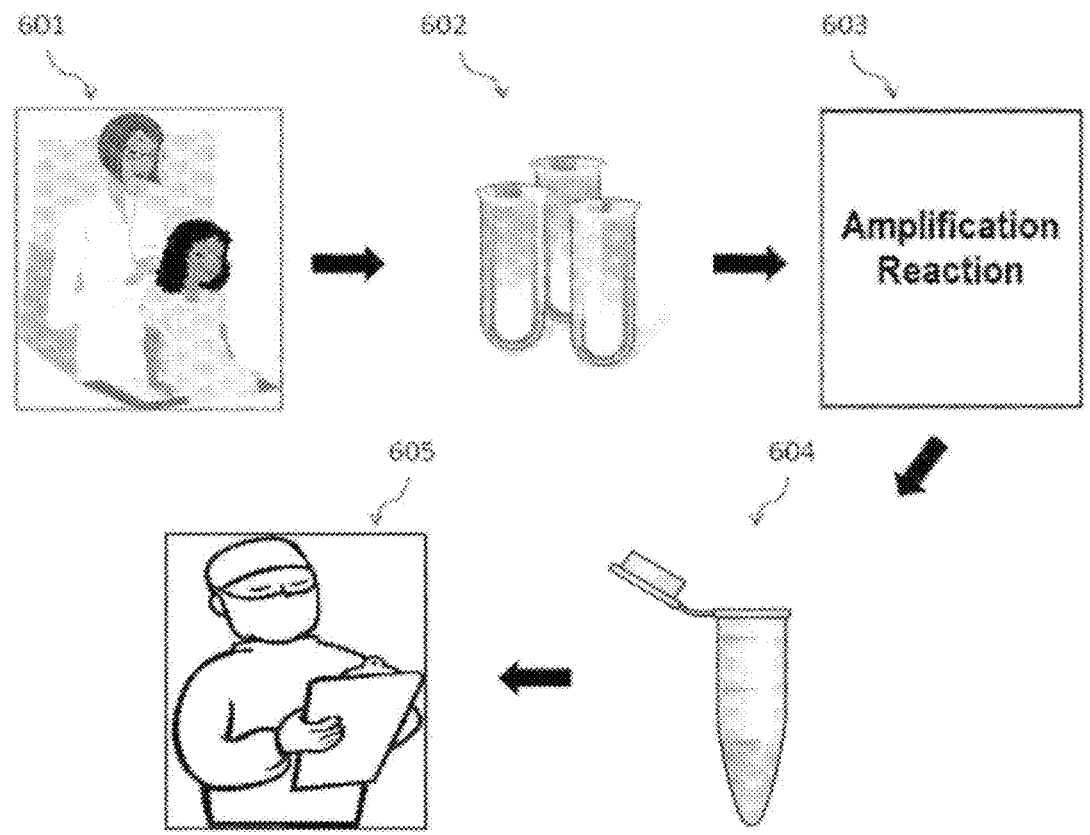
FIG. 5 illustrates a diagnostic protocol and treatment method for use with detection methods described herein.

In some cases, the presence of an analyte or a genetic variation in an analyte (e.g., a SNP) can serve as a disease marker. In some cases, the method disclosed herein can be used to detect a disease marker. In some cases, the method disclosed herein can be applicable in determining the presence or absence or the type of diseases affecting a patient. For example, FIG. 5 illustrates an overview of a method of providing a treatment in conjunction with a detection method described herein. 601 illustrates a clinician preparing to take a sample from a patient. In some cases, the sample can be a blood sample. In some cases, the sample can be a tissue sample. 602 illustrates the sample in an Eppendorf tube. 603 indicates the amplification step. 604 illustrates products from the PCR assay that have been performed to amplify the hybridized biomarkers. 605 depicts a clinician returning the results of an analysis to a subject.

X. Compositions and Kits

This disclosure also provides compositions and kits for use with the methods described herein. The compositions may comprise any component, reaction mixture and/or intermediate described herein, as well as any combination thereof. For example, the disclosure provides detection reagents for use with the methods provided herein. Any suitable detection reagents may be provided, including a primer pair labeled with two different chromophores (e.g., a donor chromophore and an acceptor chromophore), as described elsewhere in the specification.

In some cases, compositions comprise a first and a second primer or probe for the detection of at least one analyte wherein the primers are labeled with either a FRET donor or a FRET acceptor at the 5' end. In some cases, compositions comprise primers labeled at the 5' end with either a FRET donor or a FRET acceptor for the detection of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, or 10000 analytes. In some cases, compositions comprise primers labeled with multiple different FRET donors or acceptors wherein at least one donor or acceptor is at the 5' end for the detection of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, or 10000 analytes. In some cases the compositions comprise multiple pairs of first and second primers, wherein each pair of first and second primers comprise either a FRET donor or a FRET acceptor at the 5' end. In some cases each pair of first and second primers comprise a different FRET donor and FRET acceptor from the remaining set of primers. In some cases the compositions comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, or 10000 pairs of first and second primers.

The present disclosure also provides kits for carrying out the methods of the invention. Accordingly, a variety of kits are provided in suitable packaging. The kits may be used for any one or more of the uses described herein, and, accordingly, may contain instructions for detecting the presence or absence of each analyte or a plurality of analytes. A kit may be a diagnostic kit, for example, a diagnostic kit suitable for the detection of one or more analytes, including the analytes recited herein. A kit may contain any of the compositions provided in this disclosure, including those recited above.

XI. Services

The methods provided herein may also be performed as a service. For example, a service provider may obtain the identity of a plurality of analytes that a customer wishes to analyze. The service provider may then encode each analyte to be detected by any of the methods described herein and provide appropriate reagents to the customer for the assay. The customer may perform the assay and provide the results to the service provider for decoding. The service provider may then provide the decoded results to the customer. The customer may also encode analytes, generate probes, and/or decode results by interacting with software installed locally (at the customer's location) or remotely (e.g., on a server reachable through a network). Exemplary customers include clinical laboratories, physicians, manufacturers of food and consumer products, industrial manufacturers (e.g., petroleum companies) and the like. A customer or party may be any suitable customer or party with a need or desire to use the methods, systems, compositions, and kits of the invention.

A. Server

Figure 6:
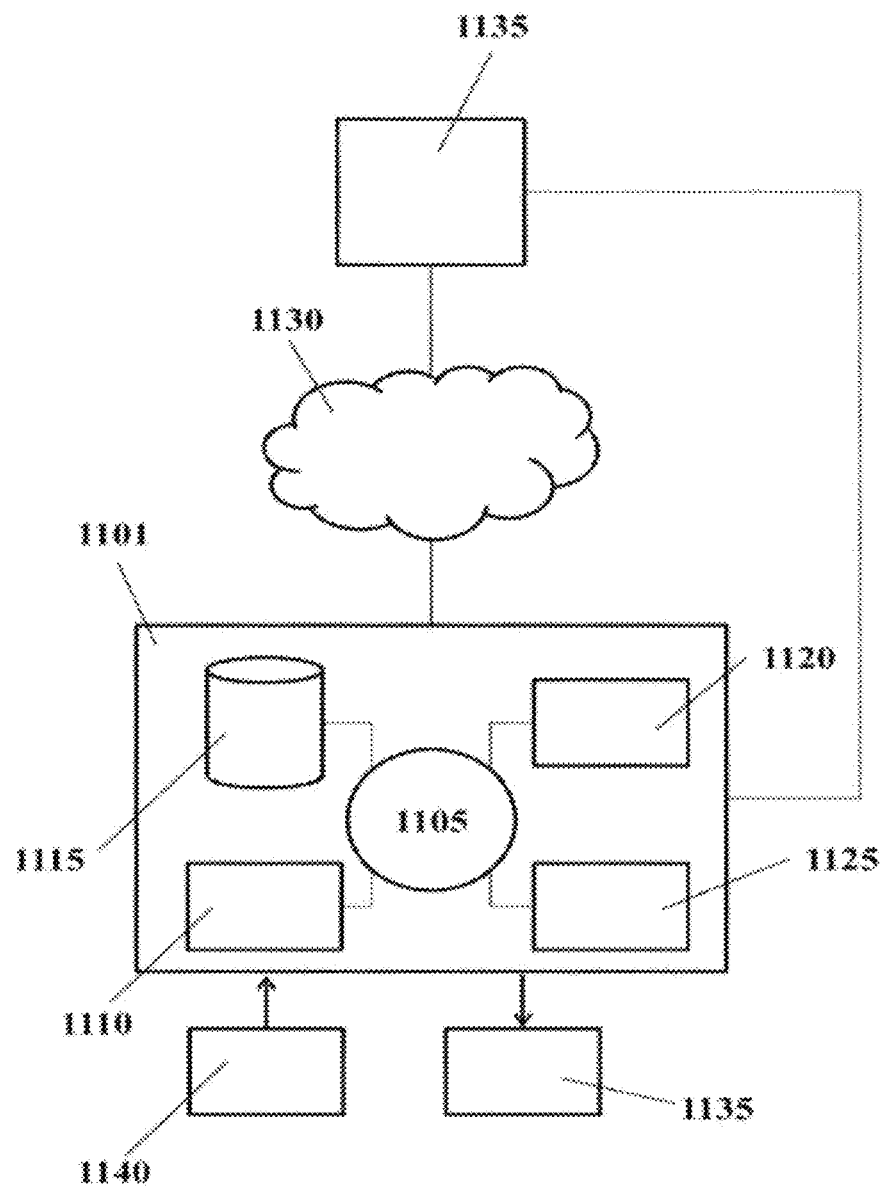
FIG. 6 illustrates a conceptual schematic of an exemplary computer server to be used for processing methods described herein.

The methods provided herein may be processed on a server or a computer server (FIG. 6). The server 1101 includes a central processing unit (CPU, also "processor") 1105 which can be a single core processor, a multi core processor, or plurality of processors for parallel processing. A processor used as part of a control assembly may be a microprocessor. The server 1101 also includes memory 1110 (e.g. random access memory, read-only memory, flash memory); electronic storage unit 1115 (e.g. hard disk); communications interface 1120 (e.g. network adaptor) for communicating with one or more other systems; and peripheral devices 1125 which may include cache, other memory, data storage, and/or electronic display adaptors. The memory 1110, storage unit 1115, interface 1120, and peripheral devices 1125 are in communication with the processor 1105 through a communications bus (solid lines), such as a motherboard. The storage unit 1115 can be a data storage unit for storing data. The server 1101 is operatively coupled to a computer network ("network") 1130 with the aid of the communications interface 1120. A processor with the aid of additional hardware described herein, may also be operatively coupled to a network. The network 1130 can be the Internet, an intranet and/or an extranet, an intranet and/or extranet that is in communication with the Internet, a telecommunication or data network. The network 1130 in some cases, with the aid of the server 1101, can implement a peer-to-peer network, which may enable devices coupled to the server 1101 to behave as a client or a server. In general, the server may be capable of transmitting and receiving computer-readable instructions (e.g., device/system operation protocols or parameters) or data (e.g., sensor measurements, raw data obtained from detecting nucleic acids, analysis of raw data obtained from detecting nucleic acids, interpretation of raw data obtained from detecting nucleic acids, etc.) via electronic signals transported through the network 1130. Moreover, a network may be used, for example, to transmit or receive data across an international border.

The server 1101 may be in communication with one or more output devices 1135 such as a display or printer, and/or with one or more input devices 1140 such as, for example, a keyboard, mouse, or joystick. The display may be a touch screen display, in which case it may function as both a display device and an input device. Different and/or additional input devices may be present such an enunciator, a speaker, or a microphone. The server may use any one of a variety of operating systems, such as for example, any one of several versions of Windows, or of MacOS, or of Unix, or of Linux.

The storage unit 1115 can store files or data associated with the operation of a device or method described herein.

The server can communicate with one or more remote computer systems through the network 1130. The one or more remote computer systems may be, for example, personal computers, laptops, tablets, telephones, Smart phones, or personal digital assistants.

In some situations a control assembly includes a single server 1101. In other situations, the system includes multiple servers in communication with one another through an intranet, extranet and/or the Internet.

The server 1101 can be adapted to store device operation parameters, protocols, methods described herein, and other information of potential relevance. Such information can be stored on the storage unit 1115 or the server 1101 and such data can be transmitted through a network.

The details of one or more embodiments of the disclosure are set forth in the accompanying drawings and the description below. Other features, objects, and advantages will be apparent from the description and drawings, and from the claims.

EXAMPLES

The FRET labeled primers methods and system herein described are further illustrated in the following examples, which are provided by way of illustration and are not intended to be limiting. In particular, in the following examples a further a description of the FRET-labeled primers and related methods and systems of the present disclosure is provided with reference to detection of KRAS mutation performed by FRETplexing in combination with qPCR. A person skilled in the art will appreciate the applicability of the features described in detail for FRET-chromophore-labeled primers designed to detect different SNPs or other genetic variations or other variations including deletion, mutations and insertions involving more than one residue in the polynucleotide analytes with different FRET labels in accordance with the present disclosure. In particular, a skilled person reading the present disclosure will appreciate that the FRET-chromophore-labeled primers illustrated in the Examples, are only one exemplary of FRET-chromophore-labeled primers and that FRET-chromohore-labeled primers can include also other fluorophores identifiable to a skilled person.

Example 1: Exemplary Experimental Approach for FRET Detection of SNPs

An approach involving use of FRET-chromophore-labeled primers in standard q-PCR has been designed to achieve SNPs detection. In particular, in the following approach, primers are designed and labeled in view of the specific SNPs to be detected and then used in q-PCR experiments for the related detection.

In order to design the primers first, at least one target sequence is selected which is associated with the SNP (or other mutation) to be detected. In particular, at least one of the target sequences corresponds to the primers, preferably both target sequences includes the sequence where the SNP to be detected might be located. In particular, in cases in which both primers carry corresponding FRET donor-acceptor, the target sequences are identified so that upon specific binding of the primers the FRET donor and FRET acceptor attached to the primers are located at a distance up to four times their related Förster distance, preferably within three times the related Förster distance one with respect to the other, more preferably within two times the Förster distance one with respect to the other, even more preferably within or at the Förster distance one with respect to the other.

For example for the FRET donor-acceptor chromophore pair Cy3 and Cy5 the target sequence are selected on the polynucleotide analyte so that upon binding on the respective primer Cy3 and Cy5 are placed at the related Förster distance of 5.6 nm one with respect to the other. Therefore the target sequences will be selected on the polynucleotide to be investigated so that upon specific hybridization a pair of suitable primers will locate the Cy3 and Cy5 label within 5.6 nm. Based on the base pair to length conversion factor identifiable to a skilled person in the art, the optimal FRET distance between one FRET chromophore and the other is preferably in a range between 15-250 bp, more preferably in a range between 15-80 bp, possibly up to 1,000 bp. Such ranges can be different depending on particular chemical environments, instrumentation used in the qPCR experiments and many other factors that may contribute to the FRET signal detection.

A pair of forward and reverse primers is then constructed to be specific to a corresponding target sequence at the reaction conditions of the q-PCR. Identification and design of specific primer for a target sequence can be performed by applying, the general concepts for PCR primer design which are identifiable by a person skilled in the art. In general, the primers can be selected to ensure that the forward and reverse primers are specific to the corresponding target sequence and have similar melting temperatures (preferably within 1 or 2° C. one from the other and no more than 5° C.) so that specific hybridization and extension of both forward and reverse primers takes place under same reaction conditions in reaction mixture. Under reaction conditions of commercially available q-PCR kits, primers can be typically between 20 to 35 bp long to allow for enough specificity at the related melting temperatures, typically within a range between 55-65° C., possibly between 50-75° C. The limit for the melting temperatures is below the boiling point of water and the enzyme hybridization temperature. When the target sequence includes a SNP or point mutation, the primers typically have the 3' end base overlapping the point mutation to maximize sensitivity. In particular, for detection of a SNP a base complementary to the expected SNP in the target sequence is included in the primer at the 3' end of the primer within a range of 1 to 3 bp from such 3' end towards the 5' end direction, preferably at the 3' terminus. The mutations cannot be located beyond the 3'end in the 5'->3' direction of the primer as such location renders the primer non-specific for the SNP to be detected.

A similar approach can be used for a different variation of a reference polynucleotide analyte, e.g. a mutation, deletion or insertion, wherein the primers can be designed so that they specifically bind to a target sequence where the expected variation might be located one or more consecutive base pairs that are indicative of the variation. In particular, the primer are designed to specifically bind the sequence indicative of the variation preferably with their 3' end.

Each forward and reverse primer is then labeled with a FRET chromophore (in the following examples Cy3-Cy5). The FRET chromophore labels can be located anywhere along the primer sequence except for the 3' end as long as upon binding the related location one with respect to the other is within the related forester distance.

In general, a donor chromophore can be attached to the 5' end of one primer and an acceptor chromophore can be attached to the 5' end of the second primer to minimize interference of the label with primer hybridization. The attachment can be done through NHS chemistry, peptide bonding or other approaches identifiable to a person skilled in the art. When the donor is attached to the 5' end of one primer and the acceptor is attached to the 5' end of the other primer, the distance from the 5' end of one primer to the 5' end of the other primer along the template sequence should be short enough to allow efficient FRET between the donor and acceptor, preferably in a range between 15-80 bp, more preferably between 15-45 bp.

As described previously, the donor and acceptor fluorophores are selected to form a FRET donor-acceptor chromophore pair so that when placed within a Förster distance the receptor can emit a fluorescence signal generated upon excitation by the energy released from the donor with at least 50% energy transfer efficiency.

The primers are then mixed with the sample and PCR reagents (e.g. a PCR mastermix) to perform PCR experiments. Signal detection can be performed after each annealing step and each denaturing step. Each such detection is done by exciting the donor at a certain wavelength and detecting the donor emission and/or the acceptor emission at the same or different wavelengths. In particular, typically detection can be performed after one or more annealing cycle with respect to the acceptor and possibly also the donor. In cases where multiple detection is performed with different FRET donor-acceptor chromophore pair, detection can be performed of the different acceptors possibly in combination with related donors after one or more of the annealing cycle in accordance with the experimental design.

In the FRET detection herein described, the donor is expected to generate a fluorescence emission signal both after the denaturing and annealing steps, while the acceptor typically produces little to no detectable emission signal as donor excitation is not efficient in exciting the acceptor directly as this point when FRET has not occurred. Thus, no change in donor and/or acceptor emission indicates that the target sequence is absent from the sample. When the target sequence is present, primer extension and amplicon hybridization will take place, resulting in a decrease of donor emission and a concomitant increased in acceptor emission.

Following detection of FRET labels signals, the related result can be plotted in function of the time and/or annealing cycle to derive a signature profile with respect to one or both of the FRET labels and/or with respect to all the FRET labels used. For example a measured FRET signal after annealing in each cycle can be used to form a real-time curve that can be used for quantitative measurement of the target analyte.

The speed of the reaction, e.g. as measured by Ct, can be compared to a positive control to determine the relative amount of the target present. The total present of the target and the wild type can be estimated using different techniques in order to produce an abundance measurement.

Example 2: Exemplary Mutations Detected and Characterized by FRET-Based Methods and Systems FRET-based methods and systems herein described have been used in connection with detection and characterization of KRAS gene. KRAS mutations have been selected as they are a major source of drug resistance in colorectal cancer (CRC).

CRC is responsible for 140,000 new cases and 49,000 deaths per year in the US alone. One of the most effective and widely used drugs against CRC is Cetuximab. The total cost of Cetuximab therapy is estimated to be $1.75 billion per year world-wide. However, KRAS mutations lead to resistance to Cetuximab in at least 35% of the patients. As a result, the American Society of Clinical Oncology (ASCO) issued a recommendation in 2009 that patients should be tested for KRAS mutations before being prescribed the drug. Nevertheless, half of the patients that are tested negative by traditional allele-specific assays still fail the 8-week regimen with high cost.

FRET-labeled primers have been designed to detect KRAS mutation carriers. FRET-based characterization and detection methods are expected to provide carrier detection with sensitivity and accuracy.

Experiments were conducted on six of the top eight KRAS mutations: G216A, G216C, G219A, G215A, G215T and G216T. These six mutations are responsible for over 90% of all observed KRAS mutations, and are present in 18% of all CRC tumors as well as 90% of all pancreatic cancers.

While these mutations are not exhaustive, such mutations have a strong clinical representation and significance, as many of these same mutations are also found in other cancers, affording general cancer screening test that covers several of the most common cancers.

Example 3: Selection of KRAS Related Target DNA Sequences

Synthetic nucleic acid targets within KRAS gene sequences, including wild type and mutant nucleic acid were chosen for exemplary detection studies using a PCR amplification technique.

In particular, the selected wild type and six mutant sequences can be found in Table 2, in which the positions of the SNPs are underlined. Each of the mutant sequences represents one of the six above mentioned SNP mutations found in KRAS. For example, in the 216T mutant, base-pair G at locus 216 is mutated into T, while in 216C mutant, base-pair G is mutated into C. "G" is omitted from the notation for the simplicity purpose.

TABLE 2

Sequences of the wild type and mutant templates

| WT/Mutants | Sequence | SEQ ID NO |
|---|---|---|
| WT | 5'- ATG ACT GAA TAT AAA CTT GTG GTA GTT GGA GCT G̲G̲T GG̲C GTA GGC AAG AGT GCC TTG ACG ATA CAG CTA ATT CAG AAT CAT TTT GTG GAC -3' | SEQ ID NO: 1 |
| 216A | 5'- ATG ACT GAA TAT AAA CTT GTG GTA GTT GGA GCT GA̲T GGC GTA GGC AAG AGT GCC TTG ACG ATA CAG CTA ATT CAG AAT CAT TTT GTG GAC -3' | SEQ ID NO: 2 |
| 216T | 5'- ATG ACT GAA TAT AAA CTT GTG GTA GTT GGA GCT GT̲T GGC GTA GGC AAG AGT GCC TTG ACG ATA CAG CTA ATT CAG AAT CAT TTT GTG GAC -3' | SEQ ID NO: 3 |
| 216C | 5'- ATG ACT GAA TAT AAA CTT GTG GTA GTT GGA GCT GC̲T GGC GTA GGC AAG AGT GCC TTG ACG ATA CAG CTA ATT CAG AAT CAT TTT GTG GAC -3' | SEQ ID NO: 4 |
| 219A | 5'- ATG ACT GAA TAT AAA CTT GTG GTA GTT GGA GCT GCT GA̲C GTA GGC AAG AGT GCC TTG ACG ATA CAG CTA ATT CAG AAT CAT TTT GTG GAC -3' | SEQ ID NO: 5 |
| 215A | 5'- ATG ACT GAA TAT AAA CTT GTG GTA GTT GGA GCT A̲CT GGC GTA GGC AAG AGT GCC TTG ACG ATA CAG CTA ATT CAG AAT CAT TTT GTG GAC -3' | SEQ ID NO: 6 |
| 215T | 5'- ATG ACT GAA TAT AAA CTT GTG GTA GTT GGA GCT T̲CT GGC GTA GGC AAG AGT GCC TTG ACG ATA CAG CTA ATT CAG AAT CAT TTT GTG GAC -3' | SEQ ID NO: 7 |

Example 4: Design of Primers for Detection of KRAS Target DNA Sequence Using FRETplexing Specific primers were designed according to each sequence of the mutants listed in Table 2. For each of the six mutants listed in Table 2, a forward primer and a reverse primer are specifically designed so that the 5'-end of a forward primer is tagged with a donor (Cy3), the 5'-end of a reverse primer is tagged with a receptor (Cy5) and both their 3'-end basepairs match the corresponding SNP. Thus, both primers are mutation-specific. For example, the forward primer for 216A mutation has an "A" at the 3' end position and the reverse primer has a complementary "T" at the 3' end position. Table 3 shows a list of forward and reverse primers used for each of the six mutants in Table 2.

In particular, PCR reactions were performed on a Roche 480 lightcycler I and Roche 480 lightcycler II instrument. The PCR cycling conditions were set up with an initial heating step of 5 minutes at 95°, followed by 40 PCR cycles each cycle comprising a 10-second denature step at 95°, a 50-second primer annealing step at 50° and a 5-second primer extension step at 72°. Fluorescence measurements in 523 nm-568 m (Cy3) and 615 nm-670 nm (Cy5) were taken at the end of annealing for every cycle. Melt curve analysis can be performed for the amplification products to ensure that desired amplicons have been detected. Different double-stranded DNA molecules melt at different temperature, dependent upon a number of factors including GC content, amplicon length, secondary and tertiary structure etc. To produce melt curve, the PCR product is exposed to a temperature gradient from about 50° C. to 95° C. while

TABLE 3

Exemplary forward and reverse primers designed for detecting KRAS mutations

| KRAS mutation | Forward Primer | SEQ ID NO | Reverse Primers | SEQ ID NO |
|---|---|---|---|---|
| 216A | /5Cy3/GAATATAAACTTGT GGTAGTTGGAGCTGA | SEQ ID NO: 8 | /5Cy5/GCACTCTTGCCTA CGCCAT | SEQ ID NO: 9 |
| 216T | /5Cy3/GAATATAAACTTGT GGTAGTTGGAGCTGT | SEQ ID NO: 10 | /5Cy5/GCACTCTTGCCTA CGCCAA | SEQ ID NO: 11 |
| 216C | /5Cy3/GAATATAAACTTGT GGTAGTTGGAGCTGC | SEQ ID NO: 12 | /5Cy5/GCACTCTTGCCTA CGCCAG | SEQ ID NO: 13 |
| 219A | /5Cy3/GAATATAAACTTGT GGTAGTTGGAGCTGGTG A | SEQ ID NO: 14 | /5Cy5/TCAAGGCACTCT TGCCTACGT | SEQ ID NO: 15 |
| 215A | /5Cy3/GAATATAAACTTGT GGTAGTTGGAGCTA | SEQ ID NO: 16 | /5Cy5/CACTCTTGCCTAC GCCACT | SEQ ID NO: 17 |
| 215T | /5Cy3/GAATATAAACTTGT GGTAGTTGGAGCTT | SEQ ID NO: 18 | /5Cy5/CACTCTTGCCTAC GCCACA | SEQ ID NO: 19 |

Example 5: FRET Labels and Related Attachment to the KRAS Specific Primers

Cy3-Cy5 is commonly used as a FRET pair. Green excitation (Cy3) together with FRET can be used for any tissue assay as it is known from experience that the tissue tends to scatter most strongly from blue excitation.

The KRAS specific primers of Example 4 were labeled with Cy3-Cy5 FRET labels in which the forward primer is attached to Cy3 FRET donor chromophore and the reverse primer is attached to Cy5 FRET acceptor chromophore. The Cy3-Cy5 labels are attached by the manufacturer of DNA oligonucleotides as part of the fabrication process.

For FRET and primer design, for the oligos of the examples the fluorophore was attached at the 5' terminus. The linkage between the label and the base is very short (shorter than 1 bp width).

Example 6: Polymerase Chain Reactions on the KRAS DNA Target Sequences with KRAS Specific FRET-Chromophore-Labeled Primers The KRAS DNA target sequences obtained in Example 3 were amplified using the KRAS specific FRET-labeled primers of Example 5.

fluorescence readouts are continually collected. The increase in temperature causes the denaturation of the dsDNA. The point at which the dsDNA melts into ssDNA is observed as a drop in fluorescence as the chromophore/dye labels dissociate. The melt temperature of the amplicon can be determined from the melt curve.

The results of the PCR experiments on each KRAS target sequence with KRAS specific FRET-chromophore-labeled primers are discussed in the Examples 7-12 with reference to FIGS. 7-16.

Example 7: Primer Titration Experiments for Calibration of Fluorescence Output in FRETplexing Primer concentration usually has an effect on the quality and intensity of the fluorescence output. A number of PCR titration experiments were carried out for each of the six mutant sequences synthesized in Example 3 to determine optimum primer concentration to be used in subsequent detection experiments. For each mutation, a pair of forward and reverse primers specifically designed for that mutation in Example 4 was used. Each primer of the primer pair is labeled with a single color by attaching a FRET donor chromophore (Cy3) and a FRET acceptor chromophore (Cy5), respectively. Each of the PCR titration experiments includes reagents, templates and primers.

TABLE 4 primer titration experiment cocktail for each of the six mutations

| Components | Concentration | Volume |
|---|---|---|
| Reagents | 100 uM | 20 uL |
| Templates | 10 uM | 10 uL |
| Primers | 10 uM | 1-10 uL in 1 uL integers |
| DI Water | | 60-69 uL |

A calibration curve was produced for each mutation documenting the end-point fluorescence output as a function of the primer concentration.

Example 8: Proof Testing FRETplexing with Synthetic DNA

The calibration curves obtained from Example 7 were then used to design appropriate ratio of the primer concentrations when combined together in a multiplexed assay. Primers at different concentration obtained from the calibration curves were combined and tested. Tables 5-6 show different combinations of primer concentration used in multiplexed assays, each containing a mixture of at least one of the six mutant templates listed in Table 2 and at least one of the six pairs of primer pairs listed in Table 3 at various concentration ratios. The output for each of the combinations was reported in chromatograms.

TABLE 5

Combinations of primer concentration ratios used in multiplexed assays of mutations 216A, 216C and 216T

| Number | Combination of Primer Concentration |
|---|---|
| 1 | 216A: 8 ul of 10 uM; 216T: 4 ul of 10 uM |
| 2 | 216A: 8 ul of 10 uM; 216C: 2 ul of 10 uM |
| 3 | 216T: 4 ul of 10 uM; 216C: 2 ul of 10 uM |
| 4 | 216A: 8 ul of 10 uM; 216T: 4 ul of 10 uM; 216C: 2 ul of 10 uM |
| 5 | 216A: 8 ul of 10 uM; 216T: 8 ul of 10 uM; 216C: 8 ul of 10 uM |
| 6 | 216T: 8 ul of 10 uM; 216C: 8 ul of 10 uM |
| 7 | 216A: 8 ul of 10 uM; 216C: 8 ul of 10 uM |
| 8 | 216A: 8 ul of 10 uM; 216T: 8 ul of 10 uM |

TABLE 6

Combinations of primer concentration ratios used in multiplexed assays of mutations 215A, 215T and 219C

| Number | Combination of Primer Concentration |
|---|---|
| 1 | 215A: 8 ul of 10 uM; 215T: 4 ul of 10 uM |
| 2 | 215A: 8 ul of 10 uM; 219C: 2 ul of 10 uM |
| 3 | 215T: 4 ul of 10 uM; 219C: 2 ul of 10 uM |
| 4 | 215A: 8 ul of 10 uM; 215T: 4 ul of 10 uM; 219C: 2 ul of 10 uM |
| 5 | 215A: 8 ul of 10 uM; 215T: 8 ul of 10 uM; 219C: 8 ul of 10 uM |
| 6 | 215T: 8 ul of 10 uM; 219C: 8 ul of 10 uM |
| 7 | 215A: 8 ul of 10 uM; 219C: 8 ul of 10 uM |
| 8 | 215A: 8 ul of 10 uM; 215T: 8 ul of 10 uM |

Example 9: Wild Type Calibration for Mutant Primers

WT concentration can affect the specificity and sensitivity of mutant primers. A set of PCR titration experiments were carried out using a mastermix to compare the real-time PCR data with the WT sequence at various concentrations. The mastermix is a premixed solution containing a combination of DNA polymerase, dNTPs, reaction buffers and other reagents needed for a PCR reaction. Optimum WT concentrations were then determined from the calibration experiments.

The qPCR experiments were carried out with the WT sequence at five different concentrations: 10 uM, 100 uM, 1000 uM, 10,000 uM and 100,000 uM. The components for two of the qPCR WT calibration experiments including reagents, WT, and mutant primers are tabulated in Tables 7-8 with two different WT concentrations. Note that no mutant sequence is present in the WT calibration experiments. The mutant primers contained in the assay represent a mixture of 216A, 216T, 216C primer pairs each at an 8 uL of 10 uM volume/concentration.

TABLE 7

WT concentration titration experiment cocktail

| Components | Concentration | Volume |
|---|---|---|
| Reagents | 100 uM | 20 uL |
| WT | 10-100,000 uM | 10 uL |
| Each primer pair | 10 uM for each forward and reverse primer | 8 uL |

TABLE 8

WT concentration titration experiment cocktail

| Components | Concentration | Volume |
|---|---|---|
| Reagents | 100 uM | 20 uL |
| WT | 10-100,000 uM | 10 uL |
| Each primer pair | 10 uM for each forward and reverse primer | 8 uL |

Figure 7:
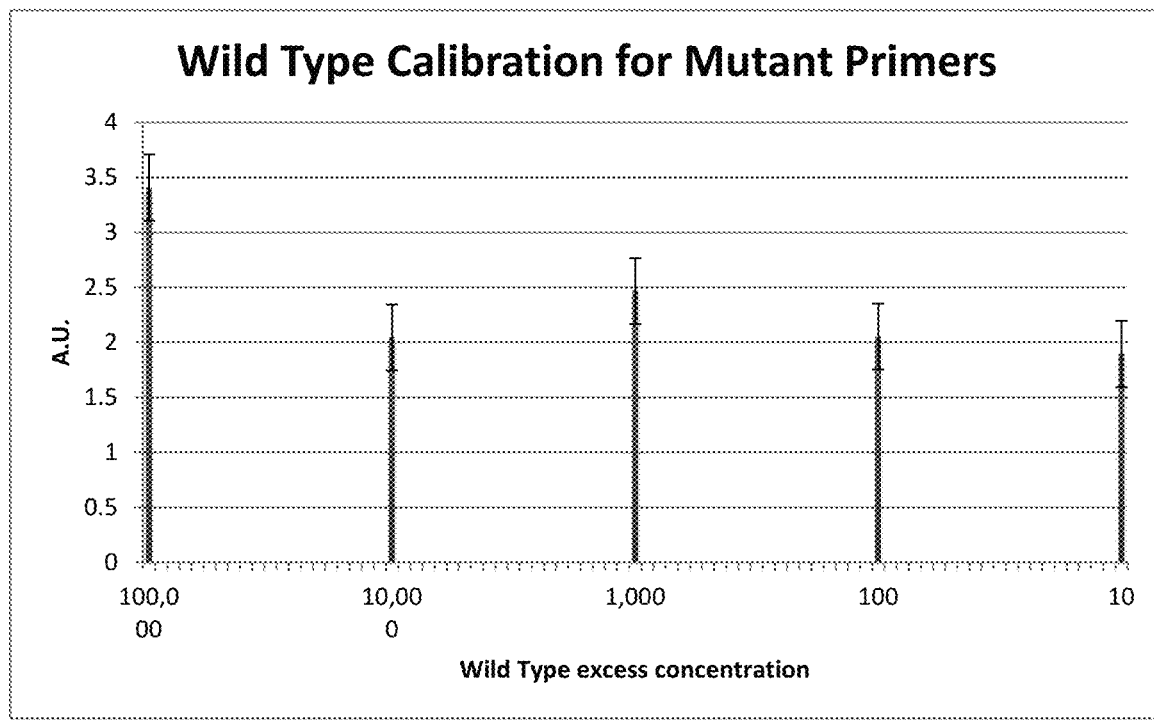
FIG. 7 shows a chart reporting the wild type concentration calibration experiments using FRET-chromophore-labeled primers with qPCR. Each multiplexed assay contains 20 uL of Taq 5× mastermix, 8 uL of 10 uM for each primer 216C, 216A and 216T and the WT sequence at different concentrations (10 uM, 100 uM, 1000 uM, 10,000 uM and 100,000 uM). 10 uL was used for each concentration. The y-axis shows averaged relative FRET emission intensities obtained from 22 qPCR replica experiments. For each qPCR experiment, the relative FRET emission intensity (delta value) is calculated by subtracting the maximum FRET emission intensity with the minimum FRET emission intensity.

FIG. 7 shows a chart reporting the wild type concentration calibration experiments using FRET-chromophore-labeled primers with qPCR. Each multiplexed assay contains 20 uL of Taq 5× mastermix, 8 uL of 10 uM for each primer 216C, 216A and 216T and the WT sequence at different concentrations (10 uM, 100 uM, 1000 uM, 10,000 uM and 100,000 uM). The y-axis shows averaged relative FRET emission intensities obtained from 22 qPCR replica experiments. For each qPCR experiment, the relative FRET emission intensity (delta value) is calculated by subtracting the maximum FRET emission intensity with the minimum FRET emission intensity.

The results indicate that as the concentration of wild type sequence increases, the delta value remains relatively leveled until the WT concentration reaches to 100,000 uM at which an increase in delta value is noted. The false positive signal observed at the high concentration suggests that mispriming has occurred due to non-specific annealing and subsequent extension upon addition of nucleotide by DNA polymerase.

Example 10: Detection of Single Mutation 216T, 216A, and 216C Using FRET-Chromophore-Labeled Primers with OCR Example described in this section is a proof of concept experiment indicating that FRET detection herein described can be used in conjunction with a qPCR without affecting the amplification reaction.

qPCR experiments were conducted to detect single mutation 216T, 216A, and 216C from KRAS gene. Tables 9-11 lists the components contained in 216T, 216A, and 216C detection experiments. Initial experiment results show a progressive increase of the emission intensity as the number of PCR cycles increase.

TABLE 9

Experiment cocktail for detection of a single 216T mutation

| Components | Volume (uL)/Concentration(uM) |
| --- | --- |
| Reagents | 20 uL of 100 uM Taq 5x matermix |
| WT | 10 uL of 100 uM |
| 216T | 10 uL of 10 uM |
| 216T primer 1x | 2 uL of 10 uM forward and reverse primer |

TABLE 10

Experiment cocktail for detection of a single 216A mutation

| Components | Volume (uL)/Concentration(uM) |
| --- | --- |
| Reagents | 20 uL of 100 uM Taq 5x matermix |
| WT | 10 uL of 100 uM |
| 216A | 10 uL of 10 uM |
| 216A primer 4x | 48 uL of 10 uM forward and reverse primer |

TABLE 11

Experiment cocktail for detection of a single 216C mutation

| Components | Volume (uL)/Concentration(uM) |
| --- | --- |
| Reagents | 20 uL of 100 uM Taq 5x matermix |
| WT | 10 uL of 100 uM |
| 216C | 10 uL of 10 uM |
| 216C primer 2x | 4 uL of 10 uM forward and reverse primer |

Figure 8:
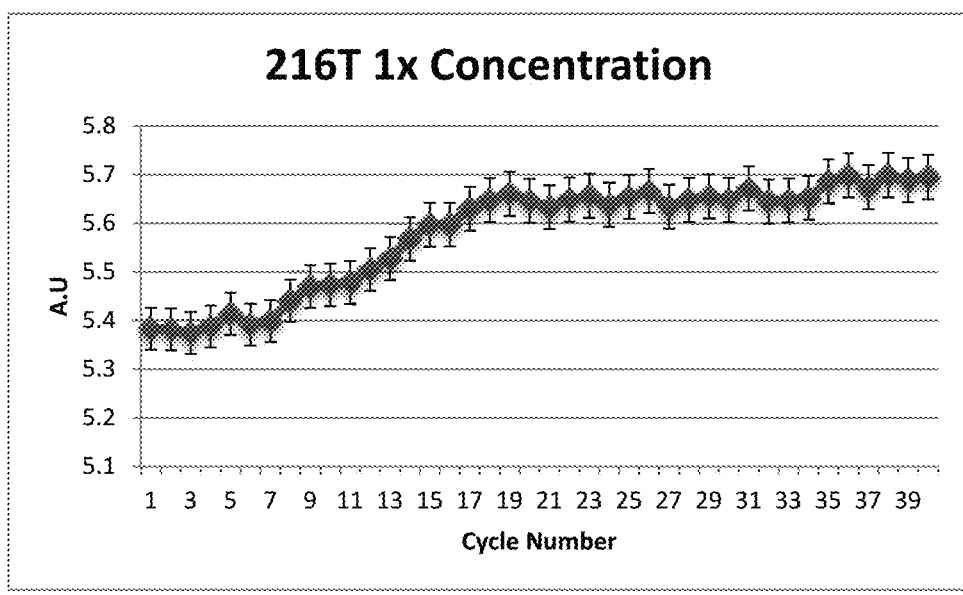
FIG. 8 shows a chart reporting detection of 216T mutant sequence from KRAS gene using FRET-chromophore-labeled primers with quantitative PCR (qPCR). The assay contains 2 uL of 10 uM forward and reverse primer concentration, 20 uL of Taq 5× mastermix, 10 uL of 10 uM 216T mutant sequence and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR experiments (y-axis) plotted as a function of PCR cycles (x-axis) with a standard deviation of 1σ. The FRET emission signal intensity is generated by Cy5 (y-axis) and detected after each annealing step. The delta value calculated by subtracting the maximum FRET signal recorded during the PCR saturation period and the minimum FRET signal recorded at the beginning of the PCR cycles is 0.27 A.U. The PCR reaction system reaches saturation at cycle 18 and the exponential growth begins at cycle 7.

FIG. 8 shows a chart reporting detection of 216T mutant sequence from KRAS gene using FRET-chromophore-labeled primers with quantitative PCR (qPCR). The assay contains 2 uL of 10 uM forward and reverse primer concentration, 20 uL of Taq 5x mastermix, 10 uL of 10 uM 216T mutant sequence and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR replica experiments (y-axis) plotted as a function of PCR cycles (x-axis) with a standard deviation of 1$\sigma$. The FRET emission signal intensity is generated by Cy5 (y-axis) and detected after each annealing step.

Generally, in a PCR curve, a baseline region in the early stage of the PCR amplification is followed by an exponential phase where an exponential increase in signal intensity is observed. The exponential phase is then followed by a plateau phase where the growth is slowed down and eventually levels off at the saturation stage where changes in signal intensity can no longer be recognized. In FIG. 8 a typical PCR curve is observed in which a baseline region in the early stage of the PCR amplification (cycles 1-6) is followed by an exponential phase (cycles 7-17) and finished with a plateau phase at cycle 15-17. The final saturation stage is reached at cycles 19.

Figure 9:
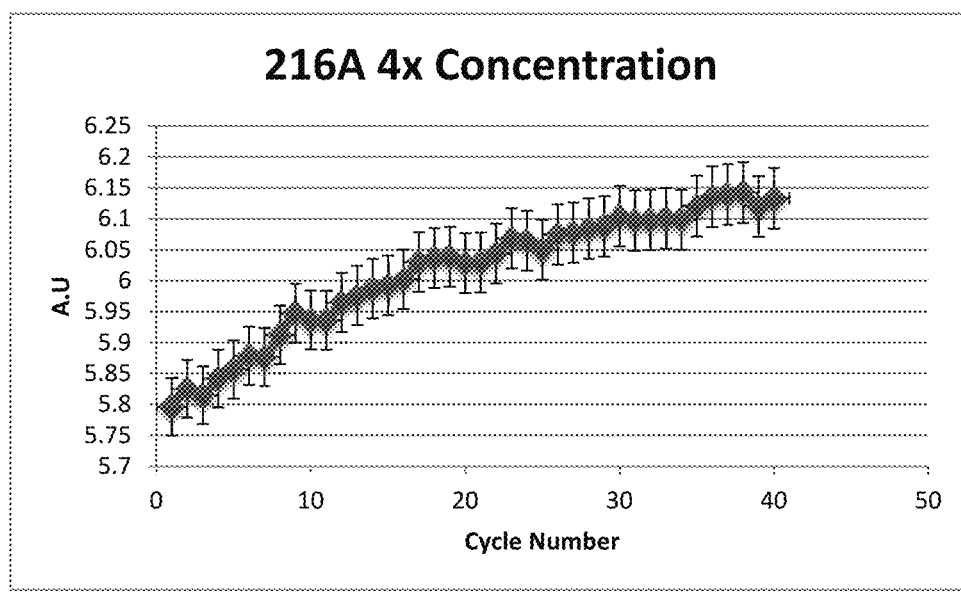
FIG. 9 shows a chart reporting detection of 216A mutant sequence from KRAS gene using FRET-chromophore-labeled primers with quantitative PCR (qPCR). The assay contains 8 uL of 10 uM forward and reverse primer concentration, 20 uL of Taq 5× mastermix, 10 uL of 10 uM 216A mutant sequence and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR replica experiments (y-axis) plotted as a function of PCR cycles (x-axis) with a standard deviation of 1σ. The FRET emission signal intensity is generated by Cy5 (y-axis) and detected after each annealing step. The delta value calculated by subtracting the maximum FRET signal recorded during the PCR saturation period and the minimum FRET signal recorded at the beginning of the PCR cycles is 0.35 A.U. The system appears to already be in the amplification cycle at the start of the experiment and reaches saturation at cycle 25.

FIG. 9 shows a chart reporting detection of 216A mutant sequence from KRAS gene using FRET-chromophore-labeled primers with quantitative PCR (qPCR). The assay contains 8 uL of 10 uM forward and reverse primer concentration, 20 uL of Taq 5x mastermix, 10 uL of 10 uM 216A mutant sequence and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR replica experiments (y-axis) plotted as a function of PCR cycles (x-axis) with a standard deviation of 1$\sigma$. The FRET emission signal intensity is generated by Cy5 (y-axis) and detected after each annealing step. The delta value calculated by subtracting the maximum FRET signal recorded during the PCR saturation period and the minimum FRET signal recorded at the beginning of the PCR cycles is 0.35 A.U. The system appears to already be in the amplification cycle at the start of the experiment and reaches saturation at cycle 25.

Figure 10:
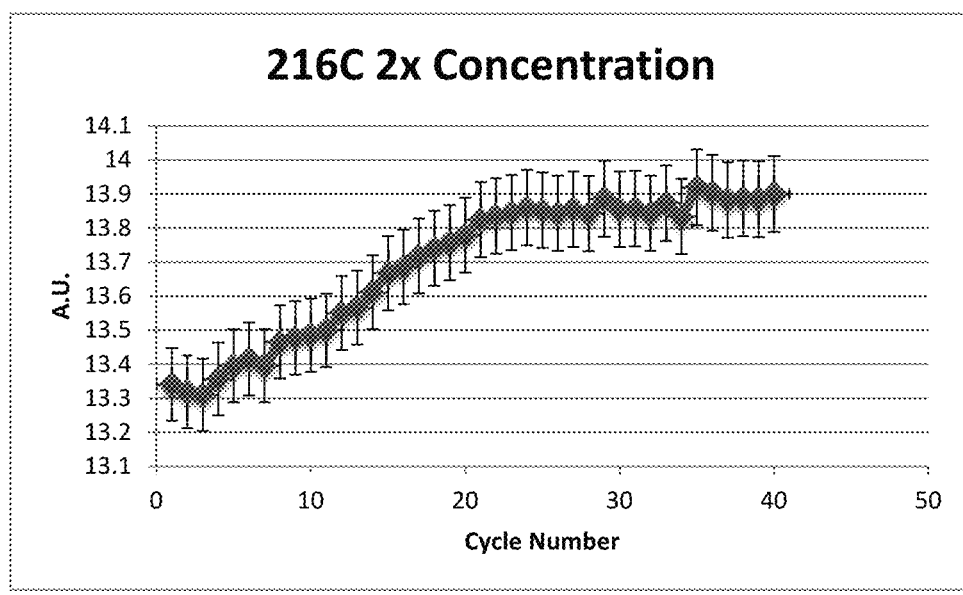
FIG. 10 shows a chart reporting detection of 216C mutant sequence from KRAS gene using FRET-chromophore-labeled primers with quantitative PCR (qPCR). The assay contains 4 uL of 10 uM forward and reverse primer concentration, 20 uL of Taq 5× mastermix, 10 uL of 10 uM 216C mutant sequence and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR replica experiments (y-axis) plotted as a function of PCR cycles (x-axis) with a standard deviation of 1σ. The FRET emission signal intensity is generated by Cy5 (y-axis) and detected after each annealing step. The delta value calculated by subtracting the maximum FRET signal recorded during the PCR saturation period and the minimum FRET signal recorded at the beginning of the PCR cycles is 0.6 A.U. The PCR reaction system reaches saturation at cycle 20 and the exponential growth begins at cycle 5.

FIG. 10 shows a chart reporting detection of 216C mutant sequence from KRAS gene using FRET-chromophore-labeled primers with quantitative PCR (qPCR). The assay contains 4 uL of 10 uM forward and reverse primer concentration, 20 uL of Taq 5x mastermix, 10 uL of 10 uM 216C mutant sequence and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR replica experiments (y-axis) plotted as a function of PCR cycles (x-axis) with a standard deviation of 1$\sigma$. The FRET emission signal intensity is generated by Cy5 (y-axis) and detected after each annealing step. The delta value calculated by subtracting the maximum FRET signal recorded during the PCR saturation period and the minimum FRET signal recorded at the beginning of the PCR cycles is 0.6 A.U. The PCR reaction system shown in FIG. 10 reaches saturation at cycle 20 and the exponential growth begins at cycle 5.

FIGS. 8-10 in particular show the successful detection of 216T, 216A and 216C mutants using the templates, primer pair designed for the specific mutant and methods described in the above examples.

The observed effect suggest an increase in the emission signal generated by the attached Cy5 upon electron transfer from Cy3 donor chromophore to Cy5 receptor chromophore following the formation of a labeled amplicon (see FIG. 4, S4 and S5).

Figure 15:
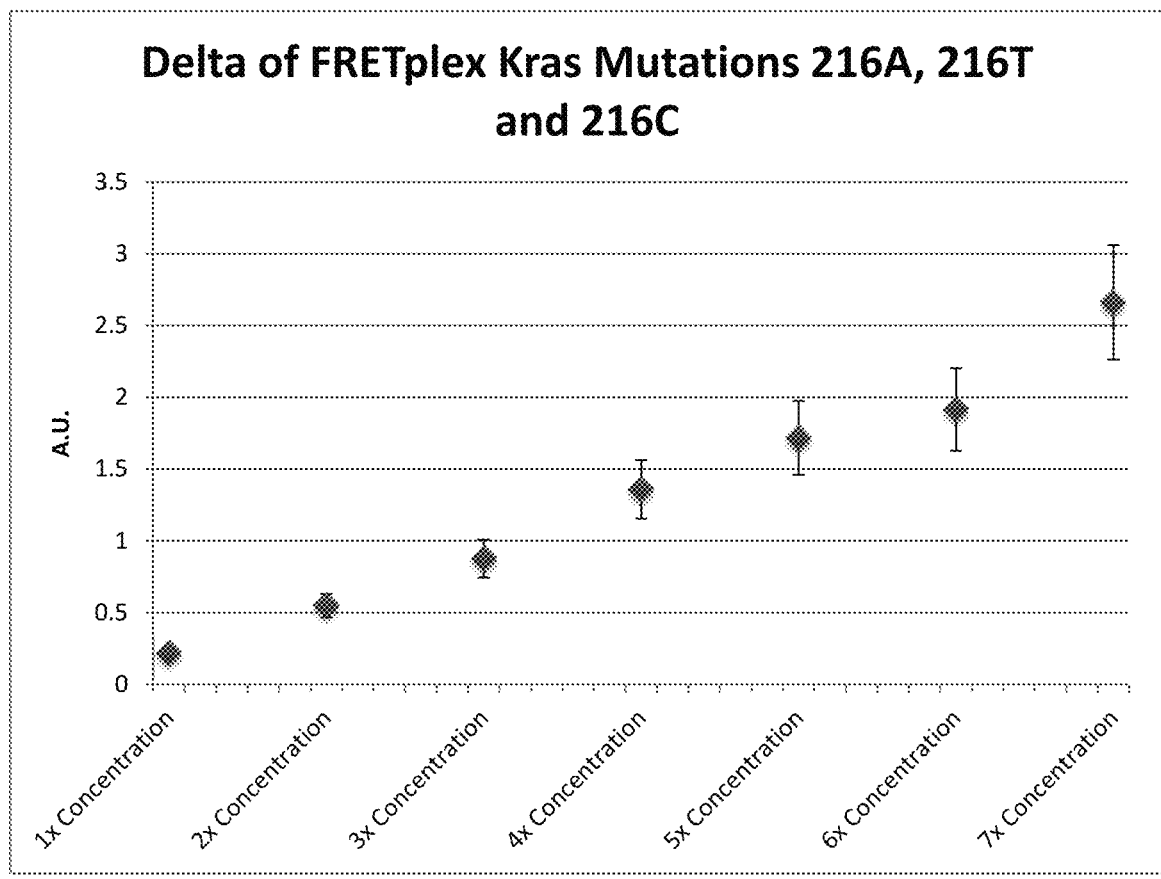
FIG. 15 shows a chart of relative FRET emission intensities (delta values) obtained from FIGS. 7-13 plotted as a function of the accumulated primer concentration ratio (x-axis) with a standard deviation of 1σ. Each delta value was the average of FRET emission signal intensity of 24 qPCR replica experiments for each concentration value. Statistical analysis was used to remove outliners from the data set.

Using the graph shown in FIGS. 8-10, a delta value can be calculated by subtracting the maximum FRET signal recorded during the PCR saturation period or at the end of the PCR cycles when the saturation period has not been in certain qPCR experiments and the minimum FRET signal recorded at the beginning of the PCR cycles (cycle 0). For example, the delta value for 216T mutant at 1× primer concentration ratio is estimated at about 0.27 A.U. Delta values from other PCR amplifications having different mutant sequence and primer concentration ratios can be obtained similarly. The delta values can then be used to chart the relatively output intensity changes that correspond to that specific mutation or a mixture of various mutations in a multiplexed assay, as shown in FIG. 15

Accordingly the experiments described herein in connection with the detection of the mutant 216T, 216A and 216C can be performed as part of FRETplex detection of multiple SNPs within the KRAS gene.

Reference is made in this connection to the illustration of FIGS. 8-10 where the notation #× used for detecting 216T, 216C and 216A mutants specifies a ratio between the concentration of one primer pair specific to a mutation and the concentration of another primer pair specific to a different mutation in a multiplexed assay.

1× denotes that the primer pair is at the lowest concentration. The lowest concentration used in the mutation detection experiments using FRET-chromophore-labeled primers with qPCR herein described is 2 uL of 10 uM for both the forward and reverse primers. 2× denotes that the primer concentration is twice the lowest concentration, which is 4 uL of 10 uM for both the forward and reverse primers. 4× denotes that the primer concentration is four times the lowest concentration, which is 8 uL of 10 uM for both the forward and reverse primers. The primer concentration level is directly related to the FRET emission intensity level, that is, the higher the primer concentration, the more intense is the FRET emission signal.

The related FRETplexing experiments are reported in Example 11.

Example 11: Detection of Multiple Mutations Based on Emission Intensity Using FRETplexing To detect multiple mutations in a single sample, multiplex assays described in Examples 3-9 were used. The goal with multiplexing is to have multiple mutations coded in a single color with each mutation assigned with different emission intensities, which can be achieved by adjusting the relative concentrations of primers when comparing two constituent assay that form a multiplexed assay. For example, a first mutation can be assigned with a single intensity (1×) with the lowest primer concentration (2 uL of 10 uM), the second mutation can be assigned with a double intensity (2×) with a primer concentration at 4 uL of 10 uM, the third mutation can be assigned with a quadruple intensity (4×) with a primer concentration at 8 uL of 10 uM, and so on. Thus, a combination of two mutations will accumulate a 3× intensity response and a combination of 3 mutations will accumulate a 7× intensity response. The level of intensity, such as 1×, 2×, 4×, and 7× can be controlled by adjusting the concentration of the primer pair for that specific mutation. Table 12 lists combinations of mutant primers at different concentrations for seven multiplexed assays. Note that the lowest prime volume is 2 uL of 10 uM for 216T primer, but any primer volume can be used as long as the FRET signal intensity is strong enough to be detected over background noise signal generated during a qPCR reaction. The concentrative primer volume for each of other primer pairs can be incremented by a multiplicative factor of 2, such as 2×, 4×, 8×, 16×, 32× and so on.

TABLE 12

Combinations of mutant primers at different concentration levels for muLtiplexed assays

| Multiplex number/accumulated concentration level | Combination of Primer Concentration | Volume |
|---|---|---|
| 1× | 216T: 2 ul of 10 uM | 10 uL |
| 2× | 216C: 4 ul of 10 uM | 10 uL |
| 4× | 216A: 8 ul of 10 uM; | 10 uL |
| 3× | 216C: 4 ul of 10 uM; | 10 uL |
|  | 216T: 2 ul of 10 uM | 10 uL |
| 5× | 216A: 8 ul of 10 uM; | 10 uL |
|  | 216T: 2 ul of 10 uM | 10 uL |
| 6× | 216A: 8 ul of 10 uM; | 10 uL |
|  | 216C: 4 ul of 10 uM | 10 uL |
| 7× | 216A: 8 ul of 10 uM; | 10 uL |
|  | 216C: 4 ul of 10 uM; | 10 uL |
|  | 216T: 2 ul of 10 uM | 10 uL |

Tables 13-16 list the components contained in the multiplexed detection experiments. For each PCR experiment, the concentration of the WT is 10 times the concentration of the mutant.

TABLE 13

Experiment cocktail for detection of a double mutation 216C at 2× and 216T at 1× primer concentrations

| Components | Concentration | Volume |
|---|---|---|
| Reagents | 100 uM | 20 uL |
| WT | 100 uM | 10 uL |
| 216C | 10 uM | 10 uL |
| 216T | 10 uM | 10 uL |
| 216C Primer | 10 uM | 4 uL |
| 216T Primer | 10 uM | 2 uL |

TABLE 14

Experiment cocktail for detection of a double mutation 216C at 2× and 216A at 4× primer concentrations.

| Components | Concentration | Volume |
|---|---|---|
| Reagents | 100 uM | 20 uL |
| WT | 100 uM | 10 uL |
| 216C | 10 uM | 10 uL |
| 216A | 10 uM | 10 uL |
| 216C Primer | 10 uM | 4 uL |
| 216A Primer | 10 uM | 8 uL |

TABLE 15

Experiment cocktail for detection of a double mutation 216T at 1× and 216A at 4× primer concentrations.

| Components | Concentration | Volume |
|---|---|---|
| Reagents | 100 uM | 40 uL |
| WT | 100 uM | 10 uL |
| 216T | 10 uM | 10 uL |
| 216A | 10 uM | 10 uL |
| 216T Primer | 10 uM | 2 uL |
| 216A Primer | 10 uM | 8 uL |

TABLE 16

Experiment cocktail for detection of a triple mutation 216C at 2×
and 216T at 1× and 216A at 4× primer concentrations.

| Components | Concentration | Volume |
|---|---|---|
| Reagents | 100 uM | 40 uL |
| WT | 100 uM | 10 uL |
| 216C | 10 uM | 10 uL |
| 216T | 10 uM | 10 uL |
| 216A | 10 uM | 10 uL |
| 216C Primer | 10 uM | 4 uL |
| 216T Primer | 10 uM | 2 uL |
| 216A Primer | 10 uM | 8 uL |

Figure 11:
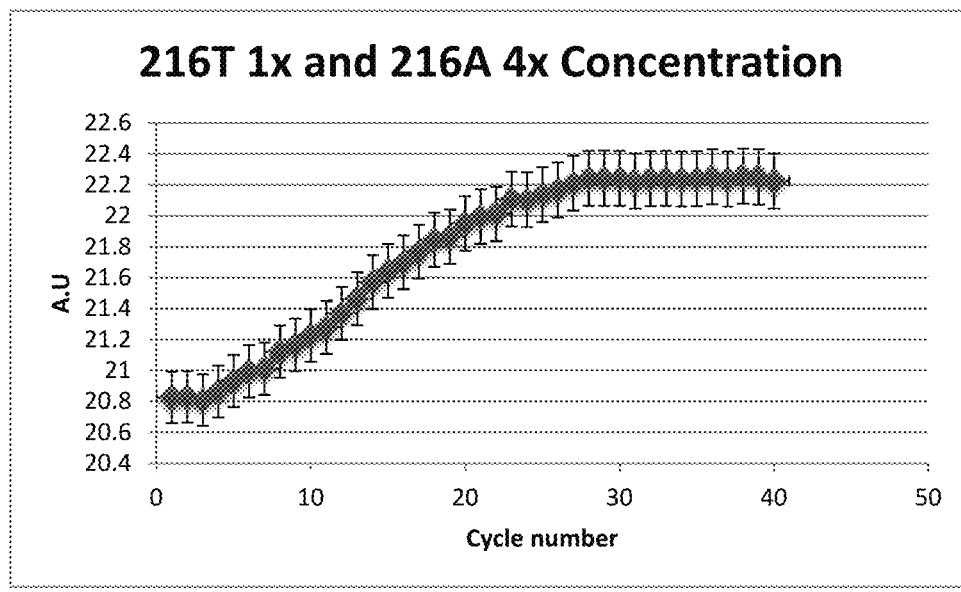
FIG. 11 shows a chart reporting detection of double mutation 216T and 216A from KRAS gene using FRET-chromophore-labeled primers with quantitative PCR (qPCR). The assay contains 8 uL of 10 uM forward and reverse primer concentration for 216A, 2 uL of 10 uM forward and reverse primer concentration for 216T, 20 uL of Taq 5× mastermix, 10 uL of 10 uM for each 216A and 216T mutant and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR replica experiments (y-axis) plotted as a function of PCR cycles (x-axis) with a standard deviation of 1σ. The FRET emission signal intensity is generated by Cy5 (y-axis) and detected after each annealing step. The delta value calculated by subtracting the maximum FRET signal recorded during the PCR saturation period and the minimum FRET signal recorded at the beginning of the PCR cycles is 2.0 A.U. The PCR reaction system reaches saturation at cycle 20 and the exponential growth begins at cycle 5.

FIG. 11 shows a chart reporting detection of double mutation 216T and 216A from KRAS gene using FRET-chromophore-labeled primers with quantitative PCR (qPCR). The assay contains 8 uL of 10 uM forward and reverse primer concentration for 216A, 2 uL of 10 uM forward and reverse primer concentration for 216T, 20 uL of Taq 5× mastermix, 10 uL of 10 uM for each 216A and 216T mutant and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR replica experiments (y-axis) plotted as a function of PCR cycles (x-axis) with a standard deviation of 1σ. The FRET emission signal intensity is generated by Cy5 (y-axis) and detected after each annealing step. The delta value calculated by subtracting the maximum FRET signal recorded during the PCR saturation period and the minimum FRET signal recorded at the beginning of the PCR cycles is 2.0 A.U. The PCR reaction system shown in FIG. 11 reaches saturation at cycle 20 and the exponential growth begins at cycle 5

Figure 12:
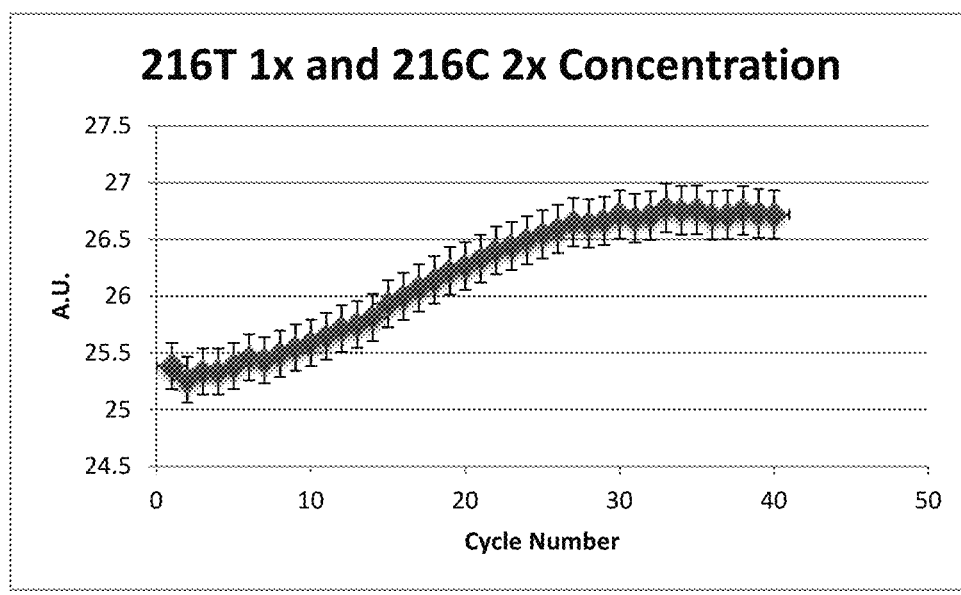
FIG. 12 shows a chart reporting detection of double mutation 216T and 216C from KRAS gene using FRET-chromophore-labeled primers with quantitative PCR (qPCR). The assay contains 4 uL of 10 uM forward and reverse primer concentration for 216C, 2 uL of 10 uM forward and reverse primer concentration for 216T, 20 uL of Taq 5× mastermix, 10 uL of 10 uM for each 216C and 216T mutant and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR replica experiments (y-axis) plotted as a function of PCR cycles (x-axis) with a standard deviation of 1σ. The FRET emission signal intensity is generated by Cy5 (y-axis) and detected after each annealing step. The delta value calculated by subtracting the maximum FRET signal recorded during the PCR saturation period and the minimum FRET signal recorded at the beginning of the PCR cycles is 1.6 A.U. The PCR reaction system reaches saturation at cycle 25 and the exponential growth begins at cycle 6.

FIG. 12 shows a chart reporting detection of double mutation 216T and 216C from KRAS gene using FRET-chromophore-labeled primers with quantitative PCR (qPCR). The assay contains 4 uL of 10 uM forward and reverse primer concentration for 216C, 2 uL of 10 uM forward and reverse primer concentration for 216T, 20 uL of Taq 5× mastermix, 10 uL of 10 uM for each 216C and 216T mutant and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR replica experiments (y-axis) plotted as a function of PCR cycles (x-axis) with a standard deviation of 1σ. The FRET emission signal intensity is generated by Cy5 (y-axis) and detected after each annealing step. The delta value calculated by subtracting the maximum FRET signal recorded during the PCR saturation period and the minimum FRET signal recorded at the beginning of the PCR cycles is 1.6 A.U. The PCR reaction system shown in FIG. 12 reaches saturation at cycle 25 and the exponential growth begins at cycle 6.

Figure 13:
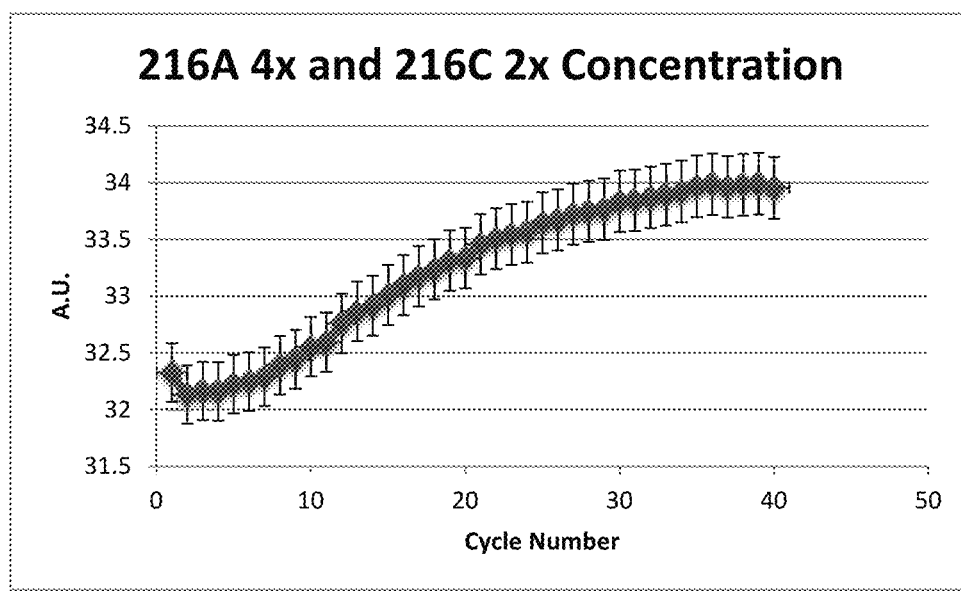
FIG. 13 shows a chart reporting detection of double mutation 216A and 216C from KRAS gene using FRET-chromophore-labeled primers with quantitative PCR (qPCR). The assay contains 4 uL of 10 uM forward and reverse primer concentration for 216C, 8 uL of 10 uM forward and reverse primer concentration for 216A, 20 uL of Taq 5× mastermix, 10 uL of 10 uM for each 216A and 216C mutant and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR replica experiments (y-axis) plotted as a function of PCR cycles (x-axis) with a standard deviation of 1σ. The FRET emission signal intensity is generated by Cy5 (y-axis) and detected after each annealing step. The delta value calculated by subtracting the maximum FRET signal recorded during the PCR saturation period and the minimum FRET signal recorded at the beginning of the PCR cycles is 1.9 A.U. The PCR reaction system reaches saturation at cycle 30 and the exponential growth begins at cycle 5.

FIG. 13 shows a chart reporting detection of double mutation 216A and 216C from KRAS gene using FRET-chromophore-labeled primers with quantitative PCR (qPCR). The assay contains 4 uL of 10 uM forward and reverse primer concentration for 216C, 8 uL of 10 uM forward and reverse primer concentration for 216A, 20 uL of Taq 5× mastermix, 10 uL of 10 uM for each 216A and 216C mutant and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR replica experiments (y-axis) plotted as a function of PCR cycles (x-axis) with a standard deviation of 1σ. The FRET emission signal intensity is generated by Cy5 (y-axis) and detected after each annealing step. The delta value calculated by subtracting the maximum FRET signal recorded during the PCR saturation period and the minimum FRET signal recorded at the beginning of the PCR cycles is 1.9 A.U. The PCR reaction system shown in FIG. 13 reaches saturation at cycle 30 and the exponential growth begins at cycle 5.

Figure 14:
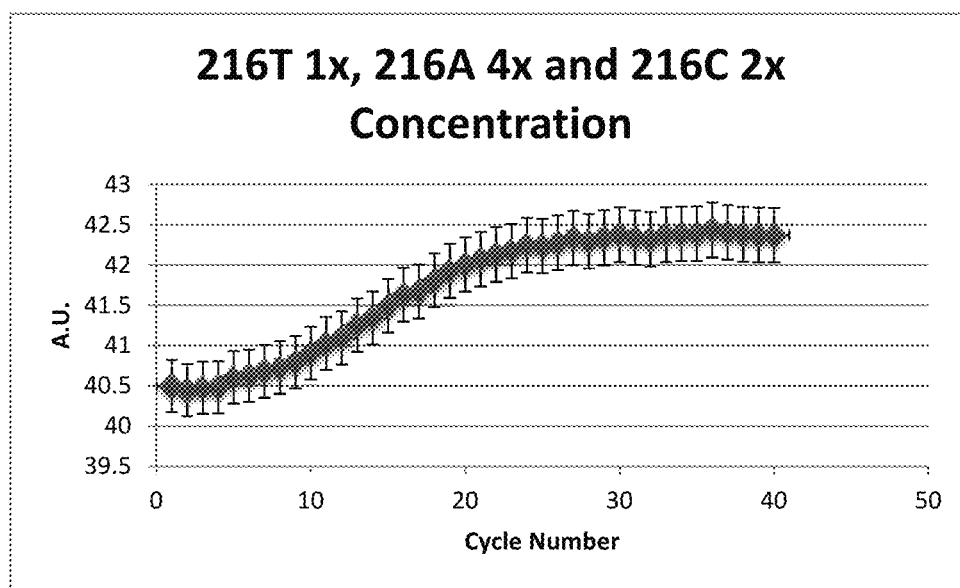
FIG. 14 shows a chart reporting detection of triple mutation 216A, 216T and 216C from KRAS gene using FRET-chromophore-labeled primers with quantitative PCR (qPCR). The assay contains 4 uL of 10 uM forward and reverse primer concentration for 216C, 8 uL of 10 uM forward and reverse primer concentration for 216A, 2 uL of 10 uM forward and reverse primer concentration for 216T, 20 uL of Taq 5× mastermix, 10 uL of 10 uM for each 216A, 216T and 216C mutant and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR replica experiments (y-axis) plotted as a function of PCR cycles (x-axis) with a standard deviation of 1σ. The FRET emission signal intensity is generated by Cy5 (y-axis) and detected after each annealing step. The delta value calculated by subtracting the maximum FRET signal recorded during the PCR saturation period and the minimum FRET signal recorded at the beginning of the PCR cycles is 2.2 A.U. The PCR reaction system reaches saturation at cycle 25 and the exponential growth begins at cycle 5.

FIG. 14 shows a chart reporting detection of triple mutation 216A, 216T and 216C from KRAS gene using FRET-chromophore-labeled primers with quantitative PCR (qPCR). The assay contains 4 uL of 10 uM forward and reverse primer concentration for 216C, 8 uL of 10 uM forward and reverse primer concentration for 216A, 2 uL of 10 uM forward and reverse primer concentration for 216T, 20 uL of Taq 5× mastermix, 10 uL of 10 uM for each 216A, 216T and 216C mutant and 10 uL of 100 uM wild type sequence. The forward primer is labeled with Cy3 as a FRET donor chromophore and the reverse primer is labeled with Cy5 as a FRET acceptor chromophore. The chart shows an averaged FRET emission signal intensity of 10 qPCR replica experiments (y-axis) plotted as a function of PCR cycles (x-axis) with a standard deviation of 1σ. The FRET emission signal intensity is generated by Cy5 (y-axis) and detected after each annealing step. The delta value calculated by subtracting the maximum FRET signal recorded during the PCR saturation period and the minimum FRET signal recorded at the beginning of the PCR cycles is 2.2 A.U. The PCR reaction system shown in FIG. 14 reaches saturation at cycle 25 and the exponential growth begins at cycle 5.

In FIG. 15, the relative FRET emission intensities (delta values at y-axis) obtained from FIGS. 8-14 are plotted as a function of the accumulated primer concentration ratio (x-axis) with a standard deviation of 1σ.

The x-axis of FIG. 15 is the accumulated intensity level calculated from summing up the primer concentration ratios in various mutations mixtures. For example, a multiplexed assay containing 216T at 1× primer concentration and 216C at 2× primer concentration results in an accumulated 3× primer concentration on the x-axis. A multiplexed assay containing 216T with 1× primer concentration, 216C at 2× primer concentration and 216A at 4× primer concentration results in an accumulated 7× primer concentration on the x-axis. The y-axis of FIG. 15 shows the relative FRET emission intensity (delta values) calculated from the qPCR curves shown in FIGS. 8-14.

FIG. 15 indicates that the intensity in A.U. shown on y-axis initially increases linearly with the level of accumulated primer concentration shown on the x-axis. As the level of accumulated primer concentration increases, the degree of multiplexing increases, the linearity is decreasing. Such effect is expected to be associated to a high level of sequence similarity between the variation to be detected (here are SNPs) In particular, it is expected that as the concentration of polynucleotide analyte in the solution increases with increased PCR reaction time, the probability of a primer finding a corresponding target sequence decreases. This issue is expected to have a lower impact in FRET detection were described where different variations to be detected have a higher lower level of sequence similarity as will be understood by a skilled person. Accuracy of the detection can be improved by detecting a FRET signals in signature profiles curve where detection of intensity is performed for a certain number of cycles to identify the deviation from the expected result due to the impact of sequence similarities or other experimental conditions and the deviation due to a lack of target sequence. The accuracy of the results can also be improved by adjusting the PCR reaction time, concentrations of the WT, mutants or primers or other PCR reaction factors.

Example 12: Detection of Multiple Mutations Based on Presence or Absence of Signal Using FRETplexing Alternatively, instead of detecting of multiple mutations based on emission intensity, the detection can also be carried out by determining the presence or absence of any mutation with a simple yes/no system, in which a given intensity indicates that a mutation is present. When no given intensity is detected, the mutation is absent.

Instead of attempting to detect a specific mutation from quantifying the signal intensity, the experiments were re-designed to determine whether a particular mutation is present or not. Table 17 list the components contained in such mutation detection experiments with the WT sequence at 10 uL of 100 uM volume/concentration. The primer pair contained in Table 17 is specific for the given mutation to be detected. Table 18 lists the components in control experiments in which mutant sequences are absent and the WT sequence has a 10 uL of 100 uM volume/concentration in one control experiment and 10 uL of 1000 uM volume/concentration in the other control experiment.

TABLE 17

Experiment cocktail for detection of any given mutation in a multiplexed assay

| Components | Concentration |
| --- | --- |
| Reagents | 20 uL of Taq 5x matermix |
| WT | 10 uL of 100 uM |
| 216T | 10 uL of 10 uM |
| 216A | 10 uL of 10 uM |
| 216C | 10 uL of 10 uM |
| 216T or 216A or 216C primer | 8 uL of 10 uM |

TABLE 18

Experiment cocktail for control experiments

| Components | Concentration |
| --- | --- |
| Reagents | 20 uL of Taq 5x matermix |
| WT | 10 uL of 100 uM or 10 uL of 1000 uM |
| 216T primer | 8 uL of 10 uM |
| 216A primer | 8 uL of 10 uM |
| 216C primer | 8 uL of 10 uM |

Figure 16:
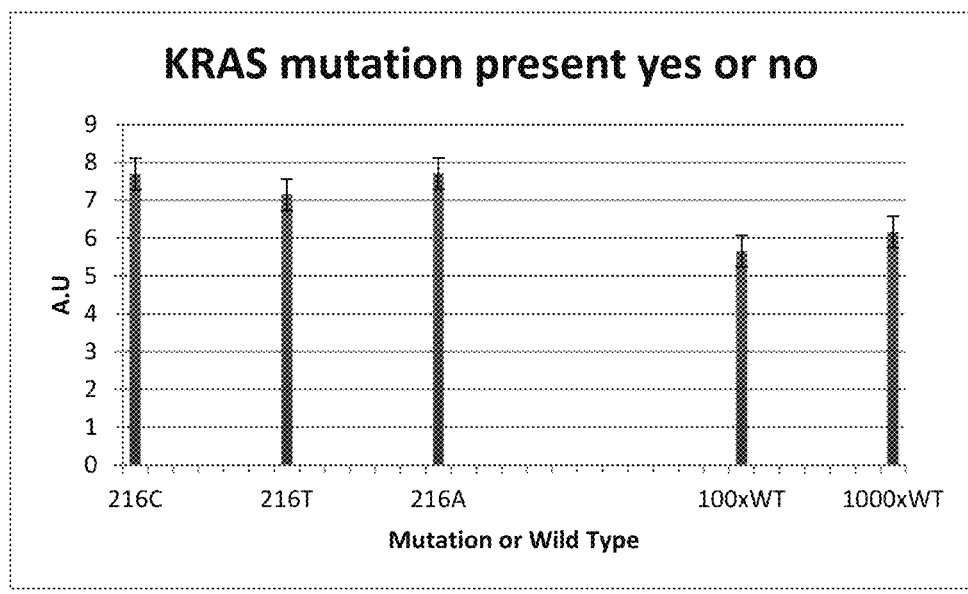
FIG. 16 shows a chart reporting the detection of the presence or absence of a KRAS mutation 216A, 216T and 216C using FRETplexing with qPCR. Each multiplexed assay contains 20 uL of Taq 5× mastermix, 10 uL of 10 uM for a given mutant sequence, 8 uL of 10 uM primer concentration for each of three primer pairs. The forward primer is labeled with Cy3 as a FRET donor chromophore and the reverse primer is labeled with Cy5 as a FRET acceptor chromophore. The chart shows averaged relative FRET emission intensities (delta values at y-axis) of 12 qPCR replica experiments plotted for each mutation also in comparison with wild type assay at two different concentrations.

FIG. 16 shows a chart reporting the detection of the presence or absence of a KRAS mutation 216A, 216T and 216C using FRETplexing with qPCR. Each multiplexed assay contains 20 uL of Taq 5x mastermix, 10 uL of 10 uM for a given mutant sequence, 8 uL of 10 uM primer concentration for each of three primer pairs. The forward primer is labeled with Cy3 as a FRET donor chromophore and the reverse primer is labeled with Cy5 as a FRET acceptor chromophore.

The chart shows averaged relative FRET emission intensities (delta values at y-axis) of 12 qPCR replica experiments plotted for each mutation also in comparison with wild type assay absence of mutants at two different concentrations: 10 uL of 100 uM wild type in one experiment and 10 uL of 1000 uM wild type in the other experiment. Note that the false intensity signal was observed in the wild-type samples, which may be caused by the mispriming of the amplification enzyme. An intensity difference when a mutant sequence is present or absent is also noted. The experiment reveals that even though there is a high concentration of wild type primers in the tested samples, the signal intensity is still greater for the mutant sequence at a much lower concentration compared to that of the wild type. In addition, the data also shows that the mutant primers are inhibited when the WT sequence concentration is increased to 100× and 1000× greater than the concentrations of the mutant sequences. Therefore, the data suggests that the FRETplex system can specifically amplify mutant sequences and can be used to determine the presence or absence of a mutant sequence when a response threshold is reached.

Example 13: PCR Amplification of Mutations 216C, 216T and 216A Using Quenchiplexing Described below are a number of PCR experiments of mutations 216C, 216T and 216A in different combinations according to the FRETplexing experiments described in Examples 10-11. For each PCR experiment, the concentration of the WT sequence is 10 times the concentration mutant WT sequence. The data are shown to provide a comparison with the above results obtained with FRETplex approach.

Similar to the FRETplexing described in the above Examples, the notation #× specifies a relative concentration of one primer pair with respect to another primer pair that forms a multiplexed assay. For each primer pair, the forward primer is designed to be specific to a given mutation and the reverse primer is a common primer. The two primers, forward and reverse primers, are labeled with a fluorophore and a quencher, respectively. Table 19 shows the forward and reverse primers used for the quenchiplexing experiments. The forward primer is labeled with Cy3 and the reverse primer is labeled with iABkFQ (Iowa black FQ). The components for each of the PCR experiments including reagents, WT, mutant and primers are tabulated in Tables 20-26. The fluorescence intensity was recorded at the end of each PCR cycle and the data are plotted into graphs shown in FIGS. 17-23.

TABLE 19

Exemplary forward and reverse primers designed for detecting KRAS mutations using quenchiplexing

| KRAS mutation | Forward Primer | SEQ ID NO | Reverse Primers | SEQ ID NO |
| --- | --- | --- | --- | --- |
| 216T | / 5Cy3/ GAATATAAACTTGT GGTAGTTGGAGCTGT | SEQ ID NO 10 | / 5iABkFQ/ GTCCACAAAATGA ATCTGAAT | SEQ ID NO: 20 |

TABLE 19-continued

Exemplary forward and reverse primers designed for detecting KRAS mutations using quenchiplexing

| KRAS mutation | Forward Primer | SEQ ID NO | Reverse Primers | SEQ ID NO |
|---|---|---|---|---|
| 216C | / 5Cy3/ GAATATAAACTTGT GGTAGTTGGAGCTG C | SEQ ID NO: 12 | / 5iABkFQ/ GTCCACAAAATG AATCTGAAT | SEQ ID NO; 20 |
| 219A | / 5Cy3/ GAATATAAACTTGT GGTAGTTGGAGCTG GTGA | SEQ ID NO 14 | / 5iABkFQ/ GTCCACAAAATG AATCTGAAT | SEQ ID NO: 20 |

TABLE 20

Experiment cocktail for detection of a single 216C mutation at a 1× primer concentration

| Components | Volume/Concentration |
|---|---|
| Reagents | 20 uL of 100 uM Taq 5x matermix |
| WT | 10 uL of 100 uM |
| 216C | 10 uL of 10 uM |
| 216C Primer | 0.5 uL of 10 uM |

TABLE 21

Experiment cocktail for detection of a single 216T mutation at a 2× primer concentration

| Components | Concentration |
|---|---|
| Reagents | 20 uL of 100 uM Taq 5x matermix |
| WT | 10 uL of 100 uM |
| 216T | 10 uL of 10 uM |
| 216T Primer | 1 uL of 10 uM |

TABLE 22

Experiment cocktail for detection of a single 216A mutation at a 4× primer concentration

| Components | Concentration |
|---|---|
| Reagents | 20 uL of 100 uM Taq 5x matermix |
| WT | 10 uL of 100 uM |
| 216A | 10 uL of 10 uM |
| 216A Primer | 2 uL of 10 uM |

TABLE 23

Experiment cocktail for detection of a double mutation 216C at 1× and 216T at 2× primer concentrations.

| Components | Concentration |
|---|---|
| Reagents | 20 uL of 100 uM Taq 5x matermix |
| WT | 10 uL of 100 uM |
| 216C | 10 uL of 10 uM |
| 216T | 10 uL of 10 uM |
| 216C Primer | 0.5 uL of 10 uM |
| 216T primer | 1 uL of 10 uM |

TABLE 24

Experiment cocktail for detection of a double mutation 216C at 1× and 216A at 4× primer concentrations.

| Components | Concentration |
|---|---|
| Reagents | 20 uL of 100 uM Taq 5x matermix |
| WT | 10 uL of 100 uM |
| 216C | 10 uL of 10 uM |
| 216A | 10 uL of 10 uM |
| 216C primer | 0.5 uL of 10 uM |
| 216A Primer | 2 uL of 10 uM |

TABLE 25

Experiment cocktail for detection of a double mutation 216T at 2× and 216A at 4× primer concentrations.

| Components | Concentration |
|---|---|
| Reagents | 20 uL of 100 uM Taq 5x matermix |
| WT | 10 uL of 100 uM |
| 216T | 10 uL of 10 uM |
| 216A | 10 uL of 10 uM |
| 216T primer | 1 uL of 10 uM |
| 216A Primer | 2 uL of 10 uM |

TABLE 26

Experiment cocktail for detection of a triple mutation 216C at 1× and 216T at 2× and 216A at 4× primer concentrations.

| Components | Concentration |
|---|---|
| Reagents | 20 uL of 100 uM Taq 5x matermix |
| WT | 10 uL of 100 uM |
| 216T | 10 uL of 10 uM |
| 216A | 10 uL of 10 uM |
| 216C | 10 uL of 10 uM |
| 216T primer | 1 uL of 10 uM |
| 216C primer | 0.5 uL of 10 uM |
| 216A Primer | 2 uL of 10 uM |

FIGS. 17-23 show the results from the above described qPCR amplification experiments using quenchiplexing.

FIG. 17 shows a chart reporting detection of 216C mutant sequence from KRAS gene using quenchiplexing with qPCR. The multiplexed assay contains 0.5 uL of 10 uM forward and reverse primer concentration, 20 uL of Taq 5× mastermix and 10 uL of 10 uM mutant 216C. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ.

FIG. 18 shows a chart reporting detection of 216T mutant sequence from KRAS gene using quenchiplexing with qPCR. The multiplexed assay contains 1 uL of 10 uM forward and reverse primer concentration, 20 uL of Taq 5× mastermix and 10 uL of 10 uM mutant 216T. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ. The amplification phase starts at cycle 8 and the saturation phase at cycle 20.

FIG. 19 shows a chart reporting detection of 216A mutant sequence from KRAS gene using quenchiplexing with qPCR. The multiplexed assay contains 2 uL of 10 uM forward and reverse primer concentration, 20 uL of Taq 5× mastermix and 10 uL of 10 uM mutant 216A. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ. The amplification phase starts at cycle 8 and the saturation phase at cycle 32.

FIG. 20 shows a chart reporting detection of 216C and 216T mutant sequence from K-RAS gene using quenchiplexing with qPCR. The multiplexed assay contains 0.5 uL of 10 uM forward and reverse primer concentration for 216C, 1 uL of 10 uM forward and reverse primer concentration for 216T, 20 uL of Taq 5× mastermix, 10 uL of 10 uM mutant 216C and 10 uL of 10 uM 216T. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ. The amplification phase starts at cycle 9 and the saturation phase at cycle 35.

FIG. 21 shows a chart reporting detection of 216C and 216A mutant sequence from K-RAS gene using quenchiplexing with qPCR. The multiplexed assay contains 0.5 uL of 10 uM forward and reverse primer concentration for 216A, 2 uL of 10 uM forward and reverse primer concentration for 216T, 20 uL of Taq 5× mastermix, 10 uL of 10 uM mutant 216C and 10 uL of 10 uM 216A. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ. The amplification phase starts at cycle 11 and the saturation phase at cycle 36.

FIG. 22 shows a chart reporting detection of 216T and 216A mutant sequence from K-RAS gene using quenchiplexing with qPCR. The multiplexed assay contains 1 uL of 10 uM forward and reverse primer concentration for 216T, 2 uL of 10 uM forward and reverse primer concentration for 216A, 20 uL of Taq 5× mastermix and 10 uL of 10 uM mutant 216T and 10 uL of 10 uM 216A. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ. The amplification phase starts at cycle 11 and the saturation phase at cycle 38.

FIG. 23 shows a chart reporting detection of 216C, 216T and 216A mutant sequence from KRAS gene using quenchiplexing with qPCR. The multiplexed assay contains 0.5 uL of 10 uM forward and reverse primer concentration for 216C, 1 uL of 10 uM forward and reverse primer concentration for 216T, 2 uL of 10 uM forward and reverse primer concentration for 216A, 20 uL of Taq 5× mastermix, and 10 uL of 10 uM for each mutant 216C, 216T and 216A. The forward primer is labeled with Cy3 as a fluorophore and the reverse primer is labeled with iABkFQ as a quencher. The chart shows averaged fluorescence emission signal of 12 qPCR replica experiments (at y-axis) plotted as a function of PCR cycles with a standard deviation of 1σ. The amplification phase starts at cycle 11 and the saturation phase at cycle 36.

In FIGS. 17-18, the amplification phase starts at cycle 8 and the saturation phase at cycle 18. The slight increase in fluorescence intensity observed after cycle 25 can be caused by the reduction of the quencher efficiency. In FIGS. 19-23, the amplification phase starts at cycle 8. However, the saturation phase is not observed in the reactions, which can be due to the fact that the PCR amplification appears to be linear instead of undergoing a traditional exponential amplification.

The fluorescence intensity in A.U. decreases as the PCR amplification progresses. Since in quenchiplexing the primers are labeled with fluorophore and quencher, respectively, the incorporation of fluorophore and quencher in the newly generated amplicon can lead to quenching of fluorescence intensity from the fluorophore. Therefore, with each iterative amplification or polymerization reaction, the fluorescence intensity is reduced gradually.

As the labeled forward and reverse primer concentrations are increased, the initial fluorescence intensity (i.e. the fluorescence intensity recorded at cycle 0) is increased and so is the delta fluorescence intensity (i.e. the fluorescence intensity difference between cycle 0 and the last cycle 40 shown in FIGS. 17-23). However, the change in delta values calculated from each of the above PCR experiments with respect to particular primer concentrations do not correspond well with the increase in the primer concentrations. Similar to the FRETplexing experimental results obtained in Example 11, the loss of linearity observed in the quenchiplexing experiments also indicates that as the concentration of mutant sequences in the solution increases with the progress of PCR reaction, the probability of a primer finding its correct target sequence becomes lower, which promotes mispriming and accumulation of nonspecific amplification products. Consequently, primer concentrations may be exhausted before the reaction is completed, resulting in lower yields of desired products, which is directly related to the lower than expected emission intensity.

In addition, the change in the slope of the graphs shown in FIGS. 17-23 is observed as the primer concentrations change. The slope of the graphs in FIGS. 17-23 becomes less steep as the total primer concentration increases. Such results also suggest that PCR reactions may be inhibited as higher primer concentrations may promote mispriming and accumulation of nonspecific products as the PCR reaction progresses.

In comparison with FRETplexing shown in Examples 1-12, the main difference between FRETplex and quenchiplex results from the fact that FRETplex produces positive signal for a positive outcome while quenchiplex produces a negative signal for a positive outcome. From perspective of metrology and statistics, the former is typically preferable. FRETplex also generally has a better signal to noise ratio compared with quenchiplex, since contrary to quenchplex FRET minimizes noise from scattering and autofluorescence. Due to increased signal sensitivity, FRETplex can preferably be applied to measurement of analytes where primers result in longer double-stranded amplicons.

Example 14. Quantification and Abundance Measurements

Methods and kits herein described can be used to perform quantification and abundance measurement of genetic variations such as SNPs. Accordingly methods and kits herein described can be used to investigate the effect of a mutation in quantitative terms. For example, in the field of oncology, if a mutation confers drug resistance, an issue to investigate is whether there a critical cutoff in its abundance in the population above which enough cancer cells survive therapy to repopulate and kill the patient. Such issue and similar require mutation abundance measurements on tumor samples of different outcomes or stages of development. To measure the abundance accurately, one must measure the total DNA present (mutant and WT) and the amount of mutant DNA. FRETplex can be used to quantify the mutant by using the FRETplex signal in a manner similar to real-time PCR, e.g. measuring threshold cycles and comparing them to a quantified control. This is an example of use of signatures of FRETplex signal, as the shape of the curve of signal vs cycle number reveals important properties of the sample.

Example 15. Multiplexed Detection

Multiplexed FRETplex assays are expected to allow several mutations to be tracked at the same time. The cumulative FRETplex signal in a same color can be considered essentially as a sum of the FRETplex real-time curves of each constituent assay. Then peculiarities of that curve, e.g. inflection points, step-wise saturations, threshold cycles, etc., can be used to decode the presence and characteristics of particular analytes. For example, if the curve experiences a Ct, then saturates, then shows another Ct then saturates at an even higher level, the decoding analysis will identify that a mutation that was amplitude-coded by the magnitude of the first plateau was present at a starting concentration consistent with the first Ct, while a mutation that was amplitude-coded by a magnitude that is the difference between the heights of the two plateau was present at a starting concentration consistent with the second Ct.

Example 16. Coding by FRET Distance

An additional application of methods and kits herein described is to perform coding by FRET distance. One can build a Multiplexed FRETplex assay e.g. for two analytes using the FRET distance as a means to code signal amplitude. For example, the first assay can be coded by a primer pair that will result in amplicons with FRET distance of say 10 nm (~30 bp), while the second analyte is coded by primers using a FRET distance of say 15 nm (~45 bp). If both assays are included in the multiplexed assay at the same primer concentration, and the resulting multiplexed assay is run to completion, there will be four possible levels of output signal: signal close to background means neither analyte was present; low signal above background means the second analyte was present alone; medium signal above background.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the text file P1647-US-Seq-List-ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

The invention claimed is:

1. A kit to detect at least one polynucleotide analyte in a sample, the kit comprising:
at least one primer pair formed by a forward primer attaching a first FRET chromophore and a reverse primer attaching a second FRET chromophore;
wherein the first FRET chromophore and the second FRET chromophore are selected to provide an energy transfer from one to another when located at a Forster distance one with respect to the another thus forming a FRET donor-acceptor chromophore pair;
the forward primer has a sequence specific for a first single strand target polynucleotide within the at least one polynucleotide analyte;
the reverse primer has a sequence specific for a second single strand target polynucleotide within the at least one polynucleotide analyte;
the first single strand target polynucleotide and the second single strand target polynucleotide are located within the at least one polynucleotide analyte so that upon specific binding of the forward primer with the first target polynucleotide and specific binding of the reverse primer with the second target polynucleotide, the first FRET chromophore and the second FRET chromophore are located at a distance up to four times the Forster distance one with respect to the other; and
wherein at least one or both the first FRET chromophore and the second FRET chromophore is attached within 10 bases of a 5' end of at least one or both the forward primer and the reverse primer and the forward primer is not complementary to the reverse primer.

2. The kit of claim 1, wherein each of the first single strand target polynucleotide and the second single strand target polynucleotide encompass a recognition sequence for the polynucleotide analyte or for a variation thereof.

3. The kit of claim 2, wherein the forward primer comprises a recognition region at a 3' end of the forward primer, the recognition region of the forward primer complementary and capable of specifically binding the recognition sequence on the first single strand target polynucleotide; and
the reverse primer comprises a recognition region at a 3' end of the reverse primer, the recognition region of the reverse primer complementary and capable of specifically binding the recognition sequence on the second single strand target polynucleotide.

4. The kit of claim 3, wherein at least a portion of the recognition sequence on the first single strand target polynucleotide is complementary to a corresponding portion of the recognition sequence of the second single strand target polynucleotide.

5. The kit of claim 4, wherein each of the at least a portion the recognition sequence on the first single strand target polynucleotide, and the corresponding portion of the recognition sequence of the second single strand target polynucleotide is equal to or less than 20 bases and each of the recognition region of the forward primer and reverse primer is within 20 bases from the respective 3' terminus.

6. The kit of claim 4, wherein the at least a portion of the recognition sequence on the first single strand target polynucleotide is 1 base, and each of the recognition region of the forward primer and reverse primer is within 1 to 3 bases from the respective 3' terminus.

7. The kit of claim 5, wherein the recognition sequence is for a genetic variation selected from a substitution, an addition, a deletion or a translocation.

8. The kit of claim 6, wherein the recognition sequence is for a genetic variation selected from a substitution, an addition, a deletion or a translocation.

9. The kit of claim 8, wherein the genetic variation is a single-nucleotide polymorphism (SNP).

10. The kit of claim 1, wherein the forward primer and the reverse primer have a length of approximately 25-30 bases each.

11. The kit of claim 10, wherein the first target sequence and the second target sequence comprise a 1 base recognition sequence for a single-nucleotide polymorphism (SNP);
the forward primer comprises a 1 base recognition region located on a 3' terminus of the forward primer or within 3 bases therefrom, the recognition region of the forward primer complementary and capable of specifically binding the recognition sequence on the first single strand target polynucleotide; and
the reverse primer comprises a 1 base recognition region located on a 3' terminus of the reverse primer or within 3 bases therefrom, the recognition region of the reverse primer complementary and capable of specifically binding the recognition sequence on the second single strand target polynucleotide.

12. The kit of claim 1, wherein at least one or both the forward primer and the reverse primer attach the first FRET chromophore at a 5' terminus of the primer.

13. A method of detecting at least one polynucleotide analyte in a sample, the method comprising:
combining the sample with the at least one primer pair formed by the forward primer attaching the first FRET chromophore and the reverse primer attaching the second FRET chromophore of the kit according to claim 1;
performing at least one polynucleotide amplification reaction with the forward primer and the reverse primer of the at least one primer pair the at least one polynucleotide amplification reaction comprising annealing of the forward primer and the reverse primer; and
measuring at least one FRET signal generated by the first FRET chromophore and/or second FRET chromophores to detect the at least one polynucleotide analyte in the sample following the annealing.

14. The method of claim 13, wherein the at least one FRET signal measured following the annealing is a FRET acceptor signal, the FRET acceptor signal measured alone or in combination with a FRET donor signal.

15. The method of claim 13, wherein the performing is carried out by performing a plurality of polynucleotide amplification reactions with the forward primer and the reverse primer of the at least one primer pair, and the measuring is performed following the annealing of each the plurality of polynucleotide amplification reactions.

16. The method of claim 15, further comprising providing a signature profile based on the FRET signal measured following the annealing of each of the plurality of the polynucleotide amplification reactions.

17. The method of claim 13, wherein the performing is performed by polymerase chain reaction or an isothermal reaction.

18. A kit to detect at least one polynucleotide analyte in a sample, the kit comprising:
a plurality of primer pairs attaching a plurality of FRET chromophores;
wherein
each primer pair is formed by a forward primer and a reverse primer each attaching a FRET chromophore;
the FRET chromophore attached to the forward primer and the FRET chromophore attached to the reverse primer of each primer pair are capable of providing an energy transfer from one to another when located at a Forster distance one with respect to the another, thus forming a FRET donor-acceptor chromophore pair;
the forward primer of each primer pair has a sequence specific for a corresponding single stranded target polynucleotide specific for the forward primer within the at least one polynucleotide analyte to be detected;
the reverse primer of each primer pair has a sequence specific for a corresponding single stranded target polynucleotide specific for the reverse primer within the at least one polynucleotide analyte to be detected;
the target polynucleotide specific for the forward primer and the target polynucleotide specific for the reverse primer are located within the at least one polynucleotide analyte to be detected so that upon specific binding of the forward primer with the single stranded target polynucleotide specific for the forward primer and specific binding of the reverser primer with the single stranded target polynucleotide specific for the reverse primer, the FRET chromophore attached to the forward primer and the FRET chromophore attached to the reverse primer are located up to four times the Forster distance one with respect to the other; and
wherein at least one or both FRET chromophore is attached at a 5' end of at least one or both the forward primer and the reverse primer and the forward primer is not complementary to the reverse primer.

19. The kit of claim 18, wherein the single strand target polynucleotide specific for the forward primer of each primer pair and the single strand target polynucleotide specific for the reverse primer of each primer pair encompass a recognition sequence for the polynucleotide analyte or for a variation thereof.

20. The kit of claim 19, wherein the forward primer of each primer pair comprises a recognition region at a 3' end of the forward primer;
the recognition region of the forward primer complementary and capable of specifically binding the recognition sequence on the corresponding single strand target polynucleotide specific for the forward primer; and
the reverse primer of each primer pair comprises a recognition region at a 3' end of the reverse primer, the recognition region of the reverse primer complementary and capable of specifically binding the recognition sequence on the corresponding single strand target polynucleotide specific for the reverse primer.

21. The kit of claim 20, wherein at least a portion of the recognition sequence on the single strand target polynucleotide specific for the forward primer of each primer pair is complementary to a corresponding portion on the recognition sequence of the single strand target polynucleotide specific for the reverse primer of each primer pair.

22. The kit of claim 21, wherein each of the at least a portion of the recognition sequence on the single strand target polynucleotide specific for the forward primer, and the corresponding portion of the recognition sequence of the single strand target polynucleotide specific for the reverse primer is equal to or less than 20 bases and each of the recognition regions of the forward primer and reverse primer is within 20 bases from the respective 3' terminus.

23. The kit of claim 21, wherein each of the at least a portion of the recognition sequence on the single strand target polynucleotide specific for the forward primer, and the corresponding portion of the recognition sequence of the single strand target polynucleotide specific for the reverse primer is 1 base, and each of the recognition regions of the forward primer and reverse primer is within 1 to 3 bases from the respective 3' terminus.

24. The kit of claim 22, the recognition sequence of the single strand target polynucleotide specific for the forward primer of each primer pair and the recognition sequence of the single strand target polynucleotide specific for the reverse primer of each primer pair, are for a same genetic variation selected from a substitution, an addition, a deletion or a translocation, each primer pair of the plurality of primer pairs specific for a different genetic variation with respect to another primer pair of the plurality of primer pairs.

25. The kit of claim 23, the recognition sequence of the single strand target polynucleotide specific for the forward primer of each primer pair and the recognition sequence of the single strand target polynucleotide specific for the reverse primer of each primer pair, are for a same genetic variation selected from a substitution, an addition, a deletion or a translocation, each primer pair of the plurality of primer pairs specific for a different genetic variation with respect to another primer pair of the plurality of primer pairs.

26. The kit of claim 25, wherein the genetic variation is a single-nucleotide polymorphism (SNP).

27. The kit of claim 26, wherein the single-nucleotide polymorphism is in a KRAS gene.

28. The kit of claim 19, wherein the forward primer and the reverse primer have a length of approximately 25-30 bases each.

29. The kit of claim 28, wherein the target sequence specific for the forward primer and the target sequence specific for the reverse primer of each primer pair comprise a recognition sequence for a single-nucleotide polymorphism (SNP);
the forward primer comprises a 1 base recognition region located on a 3' terminus of the forward primer or within 3 bases therefrom, the recognition region of the forward primer complementary and capable of specifically binding the recognition sequence on the first single strand target polynucleotide; and
the reverse primer comprises a 1 base recognition region located on a 3' terminus of the reverse primer or within 3 bases therefrom, the recognition region of the reverse primer complementary and capable of specifically binding the recognition sequence on the second single strand target polynucleotide.

30. A method of detecting at least one polynucleotide analyte in a sample, the method comprising:
combining the sample with the plurality of primer pairs of the kit according to claim 18;
performing at least one polynucleotide amplification reaction with the plurality of primer pairs the at least one polynucleotide amplification reaction comprising annealing of the forward primer and the reverse primer of each of the plurality of primer pairs; and
measuring at least one FRET signal generated by a FRET chromophore of the plurality of the FRET chromophores attached to the plurality of primer pairs to detect the at least one polynucleotide analyte in the sample following the annealing of each of the forward primer and the reverse primer of the plurality of primer pairs.

31. The method of claim 30, wherein each primer pair of the plurality of primer pairs is specific for a different variation of the at least one polynucleotide analyte, with respect to another primer pair of the plurality of primer pairs.

32. The method of claim 31, wherein the at least one FRET signal measured following the annealing is a plurality of FRET acceptor signals each from a FRET acceptor chromophore of each from a primer pair of the plurality of primer pairs, the plurality of FRET acceptor signals measured alone or in combination with a plurality of FRET donor signals each from a FRET donor chromophore corresponding to the FRET acceptor chromophore of each primer pair of the plurality of primer pairs.

33. The method of claim 32, wherein the performing is carried out by performing a plurality of polynucleotide amplification reactions with the forward primer and the reverse primer of the plurality of primer pairs, and the measuring is performed following the annealing of each the plurality of polynucleotide amplification reactions.

34. The method of claim 33, wherein the forward primer and the reverse primer of each primer pair of the plurality of primer pairs attaches a same FRET donor acceptor chromophore pair; and
combining the sample with the plurality of primer pairs is performed by providing each primer pair of the plurality of primer pairs at different concentrations.

35. The method of claim 34, further comprising providing a signature profile for the at least one polynucleotide and/or one or more variation thereof based on the FRET signals measured following the annealing of each of the plurality of the polynucleotide amplification reactions.

36. The method of claim 33, wherein the forward primer and the reverse primer of each primer pair of the plurality of primer pairs attaches a different FRET donor-acceptor chromophore pair from another primer pair of the plurality of primer pairs; and
combining the sample with the plurality of primer pairs is performed by providing each primer pair of the plurality of primer pairs at a same or different concentration.

37. The method of claim 36, further comprising providing a signature profile for the at least one polynucleotide and/or one or more variation thereof based on the FRET signals measured following the annealing of each of the plurality of the polynucleotide amplification reactions.

38. The kit of claim 1, wherein the first FRET chromophore and the second FRET chromophore are separated by 30-1000 bp along the target polynucleotides.

* * * * *